US012780893B2

(12) United States Patent
Weiss et al.

(10) Patent No.: US 12,780,893 B2
(45) Date of Patent: Nov. 3, 2026

(54) CONFORMATIONALLY CONSTRAINED GLUCAGON ANALOGUES AND THEIR USE IN GLUCAGON-SINGLE CHAIN INSULIN FUSION PROTEINS

(71) Applicant: THE TRUSTEES OF INDIANA UNIVERSITY, Bloomington, IN (US)

(72) Inventors: Michael A. Weiss, Indianapolis, IN (US); Mark A. Jarosinski, Fishers, IN (US); Balamurugan Dhayalan, Carmel, IN (US); Nicolas Mauricio Jeset Varas-Molina, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 585 days.

(21) Appl. No.: 18/264,660

(22) PCT Filed: Feb. 9, 2022

(86) PCT No.: PCT/US2022/015788
§ 371 (c)(1),
(2) Date: Aug. 8, 2023

(87) PCT Pub. No.: WO2022/173807
PCT Pub. Date: Aug. 18, 2022

(65) Prior Publication Data

US 2024/0116999 A1 Apr. 11, 2024

Related U.S. Application Data

(60) Provisional application No. 63/147,611, filed on Feb. 9, 2021.

(51) Int. Cl.

| | |
|---|---|
| ***C07K 14/605*** | (2006.01) |
| ***A61P 3/10*** | (2006.01) |
| ***C07K 14/62*** | (2006.01) |

(52) U.S. Cl.
CPC .............. *C07K 14/605* (2013.01); *A61P 3/10* (2018.01); *C07K 14/62* (2013.01); *C07K 2319/00* (2013.01)

(58) Field of Classification Search
None
See application file for complete search history.

(56) References Cited

U.S. PATENT DOCUMENTS

2019/0218268 A1 7/2019 DiMarchi et al.

FOREIGN PATENT DOCUMENTS

WO WO-2014158900 A1 * 10/2014 ................ A61P 3/10
WO 2019101035 A1 5/2019

OTHER PUBLICATIONS

PCT International Search Report and Written Opinion completed by the ISA/US on Jul. 15, 2020 and issued in connection with PCT/US2022/015788.
Balamurugan, "Engineering an Insulin/Glucagon Fusion Protein—Diabetes Research Connection", Aug. 27, 2021 (Aug. 27, 2021), XP093251304, Retrieved from the Internet: https://diabetesresearchconnection.org/projects/fusion-protein/ [retrieved on Feb. 18, 2025]; -& Nn: "Engineering an Insulin/Glucagon Fusion Protein—Verification of publication date", Google, Aug. 27, 2021 (Aug. 27, 2021), XP093251492, Retrieved from the Internet: URL:www.google.com [retrieved on Feb. 18, 2025].
Extended European Seach Report for application No. EP22753250.4, dated Jun. 26, 2025.

* cited by examiner

*Primary Examiner* — Christina Bradley
(74) *Attorney, Agent, or Firm* — Barnes & Thornburg LLP

(57) ABSTRACT

A glucagon analogue containing a lactam bridge between a Lysine introduced at position 13 and a Glutamic Acid introduced at position 17, optionally including C-terminal extensions and optionally including a second side-chain/side-chain staple beginning at or C-terminal to residue 20. The second staple may also be an (i, i+4) lactam bridge, an (i, i+3) disulfide bridge between D-Cysteine and L-Cysteine or an (i, i+7) disulfide bridge between L-Cysteine and L-Cysteine. A fusion protein containing an N-terminal lactam-stabilized glucagon analogue as above and a C-terminal single-chain insulin (SCI) analogue wherein the C domain of the SCI contains 4-11 residues is also disclosed herein. A method of treating a patient with diabetes mellitus comprises the subcutaneous, intraperitoneal, or oral administration of a physiologically effective amount of the glucagon analogue or glucagon-SCI fusion protein is also provided.

8 Claims, 20 Drawing Sheets

Specification includes a Sequence Listing.

| Molecule | $EC_{50}$ |
|---|---|
| Glucagon | 2.175 nM |
| Dasiglucagon | 1.042 nM |
| Glucagon-EEK | 93.54 nM |
| K13-E17-Lactam-EEK | 125.7 nM |
| K13-E17-Linear-EEK | 1.185 μM |

| Molecule | EC50 |
|---|---|
| Active SCI/Active Glucagon | 151.2 nM |
| Active SCI/Inactive Glucagon | 791.6 nM |
| Inactive SCI/Active Glucagon | 180.4 nM |
| Inactive SCI/Inactive Glucagon | 764.8 nM |

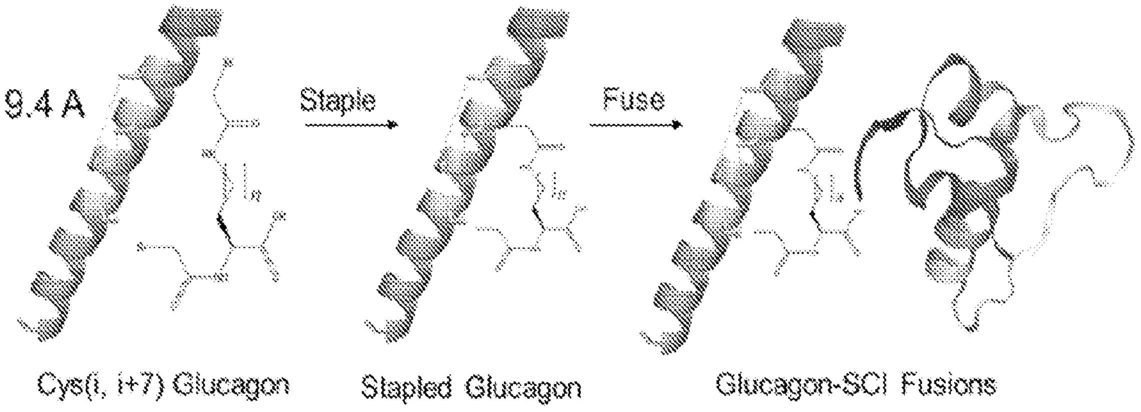

| Aaa | n | Linkers |
|---|---|---|
| Orn | 2 | 10 atom |
| Lys | 3 | 11 atom |
| Dab | 1 | 9 atom |

Fig. 20

Glucagon C-terminal (LMNT) shares similarity with Sortase-recognizing sequences (LXXTG)

Glucagon as Sortase donors

Glucagon(1-24)-WLXXTGGG

HSQGTFTSDYSKYLDSRRAQDFVQWLMNT

HSQGTFTSDYSKYLDSRRAQDFVQWLXXTG$_n$

HSQGTFTSDYSKKLDSERAQDFVQWLXXTG$_n$

HSQGTFTSDYSKKLDSERA[dC]DFCWLXXTG$_n$

SCIs as Sortase acceptors

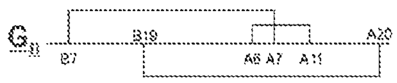

Glucagon – SCI Fusion Protein

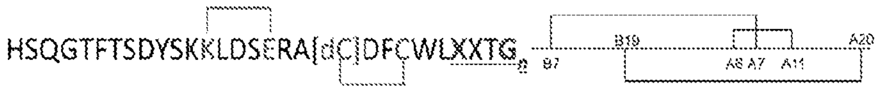

Fig. 21

CONFORMATIONALLY CONSTRAINED GLUCAGON ANALOGUES AND THEIR USE IN GLUCAGON-SINGLE CHAIN INSULIN FUSION PROTEINS

CROSS-REFERENCE TO RELATED APPLICATIONS

This application is a U.S. national counterpart application of international application serial No. PCT/US2022/015788 filed Feb. 9, 2022, which claims priority to U.S. Provisional Patent Application No. 63/147,611, filed Feb. 9, 2021, the contents of which are expressly incorporated by reference in their entireties into the present application.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 89 kilobytes ACII (text) file named "352723_ST25.txt," created on Feb. 7, 2022.

BACKGROUND

The engineering of non-standard proteins, including therapeutic agents and vaccines, may have broad medical and societal benefits. Naturally occurring peptides and proteins—as encoded in the genomes of human beings, other mammals, vertebrate organisms, invertebrate organisms, or eukaryotic cells in general—may have evolved to function optimally within a cellular context but may be suboptimal for therapeutic applications. Analogues of such peptides and proteins may exhibit improved biophysical, biochemical, or biological properties. A benefit of protein analogues would be to achieve enhanced activity (such as metabolic regulation of metabolism leading to reduction in blood-glucose concentration under conditions of hyperglycemia) with decreased unfavorable effects (such as induction of hypoglycemia or its exacerbation). Examples of therapeutic peptides and proteins are respectively provided by glucagon and insulin. The endogenous hormones bind to cognate receptors to regulate vertebrate metabolism, including in humans. An example of a medical benefit would be the design of hormone analogues more resistant to fibrillation (a major route of physical degradation of pharmaceutical formulations) than the respective wild-type hormones. Another example of a medical benefit would be a stabilized glucagon-insulin fusion protein that retains the hormonal activity of each component and whose integrated biological action would depend on the concentration of glucose in the bloodstream.

The glucagon molecule contains 29 residues and binds to a G-protein-coupled receptor (GPCR). Crystal structures of complexes between glucagon or glucagon analogues and the glucagon receptor have defined the hormone's mode of binding and key hormone-receptor contacts. Specific residues are indicated by the amino-acid type (typically in standard three-letter (or one letter) code; e.g., Lys (K) and Ala (A) indicate Lysine and Alanine) followed by the residue number. For example, Histidine at position 1, which is critically required for activity, is designated His1 (or H1). The insulin molecule contains two chains, an A chain, containing 21 residues, and a B chain containing 30 residues. The mature hormone is derived from a longer single-chain precursor, designated proinsulin. Specific residues in the insulin molecule are indicated by the amino-acid type (typically also in standard three-letter code) and in superscript the chain (A or B) and position in that chain. For example, Alanine at position 14 of the B chain of human insulin is indicated by AlaB14; and likewise, Lysine at position B28 of insulin lispro (the active component of Humalog; Eli Lilly and Co.) is indicated by LysB28. Insulin binds to a disulfide-linked dimeric receptor tyrosine kinase with chains $(\alpha\beta)_2$, where the $\alpha$ and $\beta$ chains are processed from a single biosynthetic precursor. The $\alpha$ subunit is extracellular and contains the insulin-binding sites, whereas the $\beta$ subunit is transmembrane; the latter both contributes the extracellular "legs" of the receptor and contains the intracellular tyrosine-kinase domain (one per $\beta$ subunit).

The administration of insulin has long been established as a treatment for diabetes mellitus. A major goal of conventional insulin replacement therapy in patients with diabetes mellitus is tight control of the blood-glucose concentration to prevent its excursion above or below the normal range characteristic of healthy human subjects. Excursions above the normal range are associated with an increased long-term risk of microvascular disease, including retinopathy, blindness, and renal failure. Hypoglycemia in patients with diabetes mellitus is a frequent complication of insulin replacement therapy and, when severe, can lead to significant morbidity (including altered mental status, loss of consciousness, seizures, and death). Indeed, fear of such complications poses a major barrier to efforts by patients (and physicians) to obtain rigorous control of blood-glucose concentrations (i.e., excursions within or just above the normal range), and in patients with long-established Type 2 diabetes mellitus, such efforts ("tight control") may lead to increased mortality. In addition to the above consequences of severe hypoglycemia (designated neuroglycopenic effects), mild hypoglycemia may activate counter-regulatory mechanisms, including over-activation of the sympathetic nervous system leading to turn to anxiety and tremulousness (symptoms designated adrenergic). Patients with diabetes mellitus may not exhibit such warning signs, however, defining a condition known as hypoglycemic unawareness. The absence of symptoms of mild hypoglycemia increases the risk of major hypoglycemia and its associated morbidities and mortality. Multiple and recurrent episodes of hypoglycemia are also associated with chronic cognitive decline, a proposed mechanism underlying the increased prevalence of dementia in patients with long-standing diabetes mellitus. There is therefore, an urgent need for new diabetes treatment technologies that would treat or reduce the risk of hypoglycemia while preventing upward excursions in blood-glucose concentration above the normal range.

Diverse technologies have been developed in an effort to treat or mitigate the threat of hypoglycemia in patients treated with insulin. Foundational to all such efforts is education of the patient (and also members of his or her family) regarding the symptoms of hypoglycemia and, following the recognition of such symptoms, the urgency of the need to ingest food or liquid that is rich in glucose, sucrose, or another rapidly digested form of carbohydrate; an example is provided by orange juice supplemented with sucrose (cane sugar). This baseline approach has been extended by the development of specific diabetes-oriented products, such as squeezable tubes containing an emulsion containing glucose in a form that can be rapidly absorbed through the mucous membranes of the mouth, throat, stomach, and small intestine. "Rescue" preparations of the counter-regulatory hormone glucagon, provided as a powder, have likewise been developed in a form amenable to rapid dissolution and subcutaneous injection as an emergency treatment of severe hypoglycemia. Glucagon rescue kits typically contain the hormone as a powder because aqueous solutions of wild-type glucagon exhibit exquisite susceptibility to fibrillation, which inactivates the hormone. Stabilized forms of glucagon, including glucagon analogues containing multiple amino-acid substitutions (including unnatural substitutions), have long been sought to enable the development of rescue pens containing an aqueous pharmaceutical formulation for immediate treatment of severe hypoglycemia. In the last decade, stabilized forms of glucagon have been explored as dual Glucagon/GLP-1 receptor agonists, as a treatment for obesity, motivating also design of glucagon-only agonists for co-administration with GLP-1.

The risk of hypoglycemia has motivated innovations in technologies for continuous glucose monitoring (CGM) and in the control algorithms that connect such monitors to insulin pumps. Such an algorithm may halt subcutaneous injection of insulin and trigger an audible alarm when hypoglycemic readings of the interstitial glucose concentration are encountered. Such a device-based approach has led to the recent FDA approval of closed-loop systems in which the pump and monitor are combined with a computer-based algorithm as an "artificial pancreas." A key metric for closed-loop performance is time in range (TiR), the fractional time in euglycemia and not in hypoglycemia or hyperglycemia. Efforts to optimize TiR have led to development of bihormonal pumps with control algorithms that coordinate subcutaneous injection of either insulin or glucagon. This technology has, in turn, motivated interest in glucagon analogue formulations sufficiently stable to maintain activity and fluid-flow properties for 3-7 days in the reservoir of a bihormonal pump at ambient temperatures. In such devices automated injection of a bolus of glucagon, in essence, provides a routine "rescue" from actual or predicted hypoglycemia.

The same concern for the acute and chronic complications of hypoglycemia has motivated interest in "smart" insulin delivery technologies based on glucose-responsive materials or insulin analogues. For more than three decades, there has been interest in the development of glucose-responsive macromolecular complexes, polymers and hydrogens for co-administration with an insulin analogue or modified insulin molecule, such that the rate of release of the hormone from the subcutaneous depot depends on interstitial glucose concentration. Such systems in general contain a glucose-responsive polymer, gel or other encapsulation material; they may also require a derivative of insulin, such that the modification enables binding of the hormone to the above material. An increase in the ambient concentration of glucose in the interstitial fluid at the site of subcutaneous injection may displace the bound insulin or insulin derivative either by competitive displacement of the hormone or by physical-chemical changes in the properties of the polymer, gel or other encapsulation material. The goal of such systems is to provide an intrinsic autoregulation feature to the encapsulated or gel-coated subcutaneous depot such that the risk of hypoglycemia is mitigated through delayed release of insulin when the ambient concentration of glucose is within or below the normal range. To date, no such glucose-responsive systems are in clinical use.

A recent technology exploits the structure of a modified insulin molecule, optionally in conjunction with a carrier molecule such that the complex between the modified insulin molecule and the carrier is soluble and may enter into the bloodstream (Zion et al., 2013; U.S. Pat. No. 8,569,231). This concept differs from glucose-responsive depots in which the polymer, gel or other encapsulation material remains in the subcutaneous depot as the free hormone enters into the bloodstream. An embodiment of this approach is known in the art wherein the A chain is modified at or near its N Terminus (utilizing the α-amino group of residue A1 or via the ε-amino group of a Lysine substituted at positions A2, A3, A4 or A5) to contain an "affinity ligand" (defined as a saccharide moiety) and wherein the B chain is modified at its or near N Terminus (utilizing the α-amino group of residue B1 or via the ε-amino group of a Lysine substituted at positions B2, B3, B4 or B5) to contain a "monovalent glucose-binding agent." In this description, the large size of the exemplified or envisaged glucose-binding agents (monomeric lectin domains, DNA aptamers, or peptide aptamers) restricted their placement to the N-terminal segment of the B chain as defined above. In the absence of exogenous glucose or another exogenous saccharide, intramolecular interactions between the A1-linked affinity ligand and B1-linked glucose-binding agent was envisaged to "close" the structure of the hormone and thereby impair its activity. Only modest glucose-responsive properties of this class of molecular designs were reported (Zion et al., 2013). Partial glucose-dependent biological activity has been described in rodent studies based on the binding and clearance of a saccharide-modified insulin analogue by the mannose receptor (Kaarsholm, 2018, *Diabetes* 67(2):299-308). The mechanism exploits glucose-dependent clearance of the modified insulin and not a glucose-regulated conformational change in the hormone itself. This mechanism is unrelated to the class of insulin analogues pertaining to the present disclosure, which may nonetheless contain a monosaccharide- or saccharide modification as part of a glucose-regulated conformational switch in insulin itself (FIG. 2, left).

A fundamentally different class of macromolecular designs is made possible by respective independent disclosures of fibrillation-resistance glucagon analogues and fibrillation-resistant single-chain insulin (SCI) (or modified two-chain insulin) analogues: stapled glucagon-SCI fusion proteins containing (i) an N-terminal glucagon-like moiety that retains at least a portion of its ability to bind to and trigger the glucagon receptor and (ii) a C-terminal SCI that retains at least a portion of its ability to bind to and trigger the insulin receptor (FIG. 4). The intrinsic fibrillation resistance of SCIs is known in the art and has been used to create stable insulin analogues as prandial or basal insulin analogue formulations (Weiss, U.S. Pat. Nos. 8,501,440 and 9,975,940, US published applications US 2019-0375814 and US 2020-0140517). Although this ultra-stability makes SCIs ideal to use in fusion proteins with a fibrillation-resistance glucagon, the fusion proteins disclosed herein may also contain two-chain insulin analogues also known in the art to delay (but not prevent entirely) the onset of fibrillation.

The fusion proteins of the present disclosure exploit a physiologic switch in the liver's relative hormone responsiveness (between glucagon and insulin) as a function of glycemia (FIG. 3). Under hyperglycemic conditions, insulin signaling predominates, whereas under hypoglycemic conditions, glucagon predominates. The proof of concept, demonstrating hypoglycemia protection when exogenous insulin and glucagon are co-administered, has been disclosed (Cherrington et al., 2020, US 2020-0230211). Unfortunately, this approach is confounded in practice by the intrinsic instabilities of the native hormones, thereby creating an opportunity for innovation based on novel stabilized analogues. The stabled glucagon-SCI fusion proteins of the present disclosure will therefore provide a therapeutic molecular entity that is (a) robust to pharmaceutical formulation in aqueous solution (i.e., have improved stability) and (b) efficacious in the treatment of hyperglycemia with reduced risk of hypoglycemic complications relative to wild-type insulin or insulin analogues in current clinical use due to the glucagon component being designed to have a lowered activity at the glucagon receptor and fused as a single molecular entity to the insulin component. The lower activity of the conjugated glucagon component—as enabled herein in conjunction with enhanced stability—is essential to counteract the higher relative potency of wild-type glucagon for its receptor compared to the potency of wild-type insulin, fibrillation-resistant two-chain insulin analogues or SCIs.

The present two classes of peptides (stapled glucagon analogues) or proteins (stabled glucagon-SCI fusion proteins) thus provide complementary technologies to enhance the treatment of diabetes mellitus, respectively by enabling the practicality of bihormonal pumps or by providing a bihormonal fusion protein intrinsically "buffered" against induction of hypoglycemia by a physiological switch in the liver.

SUMMARY

The present disclosure is directed toward (a) intra-chain-stapled glucagon analogues that provides aqueous hormone solutions as pharmaceutical formulations sufficiently stable to be used in the reservoir of a pump at ambient temperature for 3-7 days; and (b) fusion proteins containing an N-terminal glucagon analogue and C-terminal single-chain insulin (SCI) or modified and fibrillation-resistant two-chain insulin domain, such that the resulting protein retains at least a portion of the respective biological activities of glucagon and insulin. It is within the scope of the present disclosure that the glucagon moiety and insulin moiety are connected by a peptide bond between the C-terminal residue of the glucagon moiety and the N-terminal residue of the SCI or N Terminus of B chain on a two-chain insulin. In yet another embodiment, these elements are joined by a peptide spacer element or non-peptide linker. The fusion proteins are intended for the treatment of diabetes mellitus such that the risk of hypoglycemia is mitigated by the tethered glucagon moiety and the risk of hyperglycemia is mitigated by the tethered insulin analogue or SCI moiety.

Because the relative signaling strengths of these two hormones in the liver depend on the level of glycemia, the latter fusion proteins are envisioned to function as a glucose-responsive insulin analogue wherein insulin signaling predominates at high blood-glucose concentrations (>180 mg/dL) whereas glucagon signaling predominates at low blood-glucose concentrations (>70 mg/dL). The ratio of such relative signaling strengths can be adjusted or fine-tuned through introduction of mutations or modifications in either moiety that enhance or impair respective receptor interactions in the isolated hormones. It is one aspect of this disclosure to reduce glucagon in vitro and in vivo activities (i.e., potency) to allow for essentially unopposed action of insulin under hyperglycemic conditions, but being able to activate glucose production under hypoglycemic conditions.

BRIEF DESCRIPTION OF THE DRAWINGS

FIG. 2A) to a fusion protein of the present disclosure (FIG. 2B). Whereas the former insulin analogue exploits a structural switch in the insulin molecule on binding to the insulin receptor, the latter exploits an endogenous switch in the hormonal regulation of the liver. The glucagon-insulin fusion proteins of the present disclosure (FIG. 2B) thus do not require design of artificial glucose sensors. The ribbon model in FIG. 2B depicts such a fusion protein containing an N-terminal side-chain/side-chain stapled glucagon analogue (single α-helical ribbon on left side) and C-terminal single-chain insulin (SCI) analogue (three α-helical ribbons) as shown in expanded form in FIG. 3.

FIG. 16A shows the results from a cAMP production assay wherein the signal at 665 nm is inversely proportional to amount of cAMP produced. FIG. 16B presents the calculated $EC_{50}$ for each of the fusion proteins tested. The protein molecules carrying the active glucagon [Lys13, Glu17]-glucagon-EEK (SEQ ID NO: 23) had an $EC_{50}$ similar to the analogue alone (FIG. 8).

FIG. 20. General synthetic scheme for preparation of Cys(i, i+7) side-chain cross-linked (stapled) glucagon-SCI fusion protein (dual agonist). Panel at left shows an example of reduced (linear) glucagon peptide where Cys residues are replaced in an (i, i+7) arrangement to accommodate two turns of an α-helix (i.e., with 9.4 Å separation); middle panel, stapled glucagon intermediate derived from various bis-bromoacetyl-Lys, Orn, or Dap as the free carboxylate linker (handle), which is activated (OSnu ester) prior to attachment to the N-terminal SCI or stabilized two-chain insulin analogue. In the panel at right is shown a stapled-glucagon-SCI fusion product.

FIG. 21 Illustration showing the similarity between the C-terminal amino-acid residues of glucagon (LMNT; SEQ ID NO: 124) with the Sortase A (SrtA)-recognition sequence (LA/PXTG; SEQ ID NO: 125) required for SORTASE binding and successful SORTASE-mediated ligation reaction. Left panel shows three examples of glucagon-stapled analogues modified at the C-terminal Ala/Pro27, Gly30-32 in wild-type glucagon (SEQ ID NO: 1) and Lys13-Glu17 lactam-stapled glucagon (SEQ ID NO: 10) and double-stapled Lys13-Glu17 (lactam), D-Cys20/L-Cys23 (disulfide) glucagon (SEQ ID NO: 64). Sequences are as follows:

SEQ ID NO: 130
HSQGTFTSDYSKYLDSRRAQDFVQWLXXTGGG;;

SEQ ID NO: 1
HSQGTFTSDYSKYLDSRRAQDFVQWLMNT;;

SEQ ID NO: 131
HSQGTFTSDYSKYLDSRRAQDFVQWLXXTGGG;;

SEQ ID NO: 132
HSQGTFTSDYS<u>K</u>YLD<u>E</u>RRAQDFVQWLXXTG;;
and

SEQ ID NO: 133
HSQGTFTSDYSO<u>K</u>LDS<u>E</u>OA[D-Cys]DFCQWLXXTGGG;.

Figure 22:
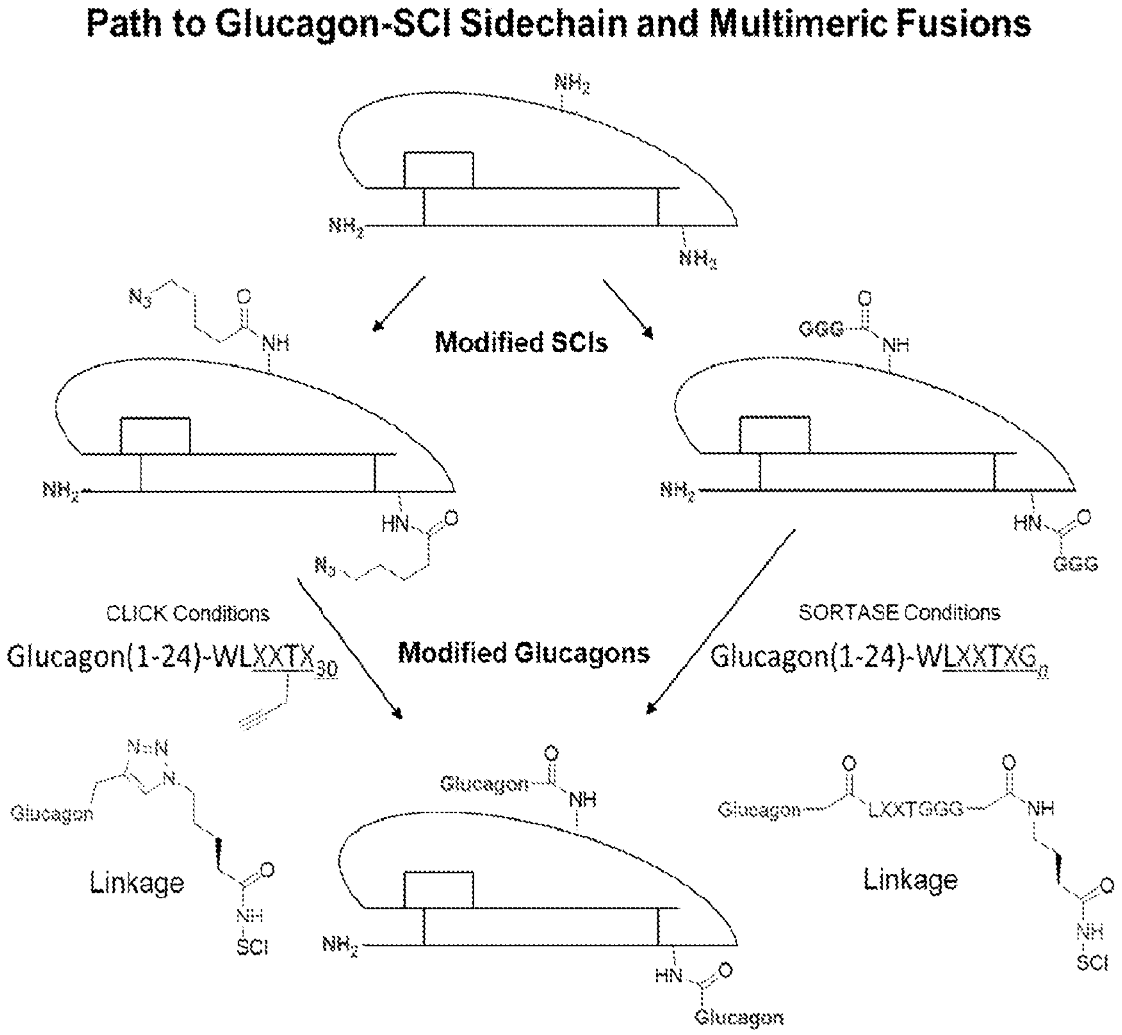

FIG. 22 General synthetic scheme for preparation of side-chain/side-chain-linked glucagon-SCI or glucagon-stabilized two-chain insulin analogue (in either case intended as dual agonist) as chemically engineered single- or multimeric fusion proteins. In this scheme the glucagon component and SCI (or insulin analogue) component each carry bio-orthogonal handles at respective sites of conjugation. The SCI- or insulin-analogue conjugation precursor contains one or multiple free side-chain amino groups (i.e., Lys, Orn, Dab, or Dap) at a position or positions to be modified by the stapled glucagon analogue. These positions can be selectively acylated without modifying the N-terminal amino group to install the bio-orthogonal handles 6-azidohexanoic acid (for click chemistry, left panel) and Gly-Gly-Gly tripeptide (for SortaseA ligation, right panel); various azide moieties could be used as well as a Gly-Gly-dipeptide. A side-chain cross-linked multimeric product is illustrated at the bottom from either click- or Sortase mediated reactions. The detailed chemical bonding of the stapled glucagon-SCI (or stapled glucagon-insulin analogue) fusions are labelled "Linkage" at bottom left and right.

DETAILED DESCRIPTION

Definitions

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. For the purposes of the present disclosure designation of an amino acid (e.g., by reference to the amino acid single-letter code) without specifying its stereochemistry is intended to encompass either the L or D form of the amino acid, or a racemic mixture. However, in the instance where an amino acid is designated by its three-letter code and includes a residue number, the D form of the amino acid is specified by inclusion of a lower case d before the three-letter code and residue number (e.g., dLys1), wherein the designation lacking the lower case d (e.g., Lys1) is intended to specify the native L form of the amino acid. In this nomenclature, the inclusion of the residue number designates the position of the amino acid in the sequence of the peptide, wherein amino acids that are located within this sequence are designated by positive residue numbers numbered consecutively from the N Terminus. Additional amino acids linked to an analogue of a native peptide either at the N Terminus or through a side chain are numbered starting with 0 and increasing in negative integer value as they are further removed from the native peptide sequence. Additional amino acids linked to the C-terminal residues of an insulin A- or B chain are numbered as consecutive residues; for example, the C-terminal Arg-Arg extension of the 32-residue B chain in insulin glargine is designed ArgB31-ArgB32.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "bioactive polypeptide" refers to polypeptides that are capable of exerting a biological effect in vitro and/or in vivo.

As used herein a general reference to a peptide/polypeptide is intended to encompass peptides/polypeptides that have modified amino- and/or carboxy termini. For example, an amino-acid sequence designating the standard amino acids is intended to encompass standard amino acids at the N- and C Terminus as well as modified amino acids, such as a corresponding C-terminal amino acid modified to comprise an amide group in place of the terminal carboxylic acid.

As used herein an "acylated" amino acid is an amino acid comprising an acyl group that is non-native to a naturally-occurring amino acid, regardless by the means by which it is produced. Exemplary methods of producing acylated amino acids and acylated peptides are known in the art; these include acylating an amino acid before inclusion in the peptide or chemical acylation of the peptide following its complete synthesis. In some embodiments the acyl group causes the peptide to have one or more of (i) a prolonged half-life in circulation, (ii) a delayed onset of action, (iii) an extended duration of action, (iv) an improved resistance to proteases and (v) increased or decreased potency at insulin receptor isoforms.

As used herein, an "alkylated" amino acid is an amino acid containing an alkyl group that is non-native to a naturally-occurring amino acid, regardless of the means by which it is produced. Exemplary methods of producing alkylated amino acids and alkylated peptides are known in the art; these include alkylating an amino acid before inclusion in the peptide or chemical alkylation of the peptide following its synthesis. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases and increased or decreased potency.

As used herein, the term "pharmaceutically acceptable carrier" includes any of the standard pharmaceutical carriers, such as a phosphate-buffered saline (PBS) solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" encompasses salts of compounds that retain the biological activity of the parent compound and that are not biologically or otherwise undesirable. Many of the compounds disclosed herein are capable of forming acid and/or base salts by virtue of the presence of amino and/or carboxyl groups or groups similar thereto.

As used herein, the term "hydrophilic moiety" encompasses any compound that is readily water-soluble or readily absorbs water, and that are tolerated in vivo by mammalian species without toxic effects (i.e., are biocompatible). Examples of hydrophilic moieties include polyethylene glycol (PEG), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein, the term "treating" includes alleviation of the symptoms associated with a specific disorder or condition and/or preventing or eliminating said symptoms. For example, as used herein the term "treating diabetes" (or "treating DM") will refer in general to maintaining blood-glucose concentrations near normal levels and may include increasing or decreasing blood-glucose concentrations depending on a given situation.

As used herein, an "effective" amount or a "therapeutically effective amount" of an insulin analogue refers to a nontoxic but sufficient amount of an insulin analogue to provide the desired effect. For example, one desired effect would be the prevention or treatment of hyperglycemia. The amount that is "effective" will vary from subject to subject, depending on the age and general condition of the individual, mode of administration, nutritional status and the like. Thus, it is not always possible to specify an exact "effective amount." However, an appropriate "effective" amount in any individual case may be determined by one of ordinary skill in the art using routine experimentation.

The term "parenteral" means not through the alimentary canal but by some other route such as intranasal, inhalation, subcutaneous (SQ), intramuscular, intraspinal, or intravenous (IV).

Throughout this application, all references to a particular amino acid position by letter and number (e.g., position A5) refer to the amino acid at that position of either the A chain (e.g., position A5 with respect to SEQ ID NO: 60) or the B chain (e.g., position B5 with respect to SEQ ID NO: 61) or the corresponding amino acid position in any insulin analogues thereof. For example, a reference herein to "position B28" absent any further elaboration could mean residue $Pro^{B28}$ in WT insulin or the corresponding position 27 of a variant B chain in an insulin analogue in which the first amino acid of SEQ ID NO: 61 has been deleted (des-B1). Similarly, amino acids added to the N Terminus of the native B chain are numbered starting with B0, followed by numbers of increasing negative value (e.g., B-1, B-2 . . . ) as amino acids are added to the N Terminus.

As used herein, the term "native human insulin" or "wild-type insulin" is intended to designate the 51 amino-acid heteroduplex comprising the A chain of SEQ ID NO: 60 and the B chain of SEQ ID NO: 61, as well as single-chain insulin (SCI) analogues that comprise SEQ ID NOS: 60 and 62 (i.e., as an A domain and a B domain). The term "insulin polypeptide" or "insulin peptide" as used herein, absent further descriptive language is intended to encompass the 51 amino-acid heteroduplex comprising the A chain of SEQ ID NO: 60 and the B chain of SEQ ID NO: 61; single-chain insulin analogues containing the native C domain of proinsulin, foreshortened C domains, novel connecting peptides, or non-peptidic linkers between the C terminus of the B chain and N-termini of the A chain are herein collectively designated SCIs (including, for example, those disclosed in published international application WO96/34882 and U.S. Pat. No. 6,630,348, the disclosures of which are incorporated herein by reference). The class of SCIs thus contains homologous peptide hormones (e.g., IGF1 and IGF2) and their variants that have activity at one or both of the insulin receptor isoforms. Such modified analogues include amino-acid modifications at one or more amino acid positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. Insulin polypeptides as defined herein can also be analogues derived from a naturally occurring insulin by insertion or substitution of a non-peptide moiety, e.g., a retroinverse fragment, or incorporation of non-peptide bonds such as an azapeptide bond (CO substituted by NH), pseudo-peptide bond (e.g., NH substituted with $CH_2$) or an ester bond (e.g., a depsipeptide, wherein one or more of the amide (—CONHR—) bonds are replaced by ester (COOR) bonds).

As used herein, the term "insulin A chain," absent further descriptive language is intended to encompass the 21 amino-acid sequence of SEQ ID NO: 60 as well as functional analogues and derivatives thereof known to those skilled in the art, including modification of the sequence of SEQ ID NO: 61 by one or more amino acid substitutions at positions selected from A4, A5, A8, A9, A10, A12, A14, A15, A17, A18, A21.

As used herein, the term "insulin B chain," absent further descriptive language is intended to encompass the 30 amino-acid sequence of SEQ ID NO: 61, as well as modified functional analogues of the native B chain, including one or more amino-acid substitutions at positions selected from B1, B2, B3, B4, B5, B9, B10, B13, B14, B17, B20, B21, B22, B23, B25, B26, B27, B28, B29 and B30 or deletions of any or all of positions B1-4 and B26-30.

As used herein, the term "derivative" is intended to encompass chemical modification to a compound (e.g., an amino acid), including chemical modification in vitro, e.g., by introducing a group in a side chain in one or more positions of a polypeptide, e.g., a nitro group in a tyrosine residue or iodine in a tyrosine residue, or by conversion of a free carboxylic group to an ester group or to an amide group, or by converting an amino group to an amide by acylation, or by acylating a hydroxy group rendering an ester, or by alkylation of a primary amine rendering a secondary amine or linkage of a hydrophilic moiety to an amino-acid side chain. Other derivatives are obtained by oxidation or reduction of the side chains of the amino-acid residues in the polypeptide.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino-acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410), are available for determining percent sequence identity.

As used herein, an amino-acid "modification" refers to a substitution of an amino acid, or the derivation of an amino acid by the addition and/or removal of chemical groups to/from the amino acid, and includes substitution with any of the 20 amino acids commonly found in human proteins, as well as atypical or non-naturally occurring amino acids. Commercial sources of atypical amino acids include Sigma-Aldrich (Milwaukee, WI), ChemPep Inc. (Miami, FL), and Genzyme Pharmaceuticals (Cambridge, MA). Atypical amino acids may be purchased from commercial suppliers, synthesized de novo, or chemically modified or derivatized from naturally occurring amino acids.

As used herein, an amino acid "substitution" refers to the replacement of one amino-acid residue by a different amino-acid residue.

As used herein, the term "conservative amino-acid substitution" is defined herein as exchanges within one of the following five groups:

- I. Small aliphatic, nonpolar or slightly polar residues:
  - Ala, Ser, Thr, Pro, Gly;
- II. Polar, negatively charged residues and their amides:
  - Asp, Asn, Glu, Gln, cysteic acid and homocysteic acid;
- III. Polar, positively charged residues:
  - His, Arg, Lys; Ornithine (Orn)
- IV. Large, aliphatic, nonpolar residues:
  - Met, Leu, Ile, Val, Cys, Norleucine (Nle), homocysteine
- V. Large, aromatic residues:
  - Phe, Tyr, Trp, acetyl phenylalanine As used herein, the general term "polyethylene-glycol chain" (or "PEG chain") encompasses mixtures of condensation polymers of ethylene oxide and water, in a branched or straight chain, represented by the general formula $H(OCH_2CH_2)_nOH$, wherein n is at least 2. "Polyethylene-glycol chain" (or "PEG chain") is used in combination with a numeric suffix to indicate the approximate average molecular weight thereof. For example, PEG-5,000 refers to polyethylene-glycol chain having a total molecular weight average of about 5,000 Daltons.

As used herein, the term "pegylated" and like terms include any compound that has been modified from its native state by linking a polyethylene-glycol chain to the compound. A "pegylated polypeptide" is a polypeptide that has a PEG chain covalently bound to the polypeptide.

As used herein, a "linker" is a bond, molecule or group of molecules that binds two separate entities to one another Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, an "insulin dimer" is a complex comprising two insulin molecules (each containing an A and B chain) bound to each other through reversible non-covalent interactions, such as van der Waal interactions, electrostatic interactions and hydrogen bonds. Solutions of insulin in the absence of zinc ions at neutral pH and at protein concentrations greater than 1 μM typically exhibit an equilibrium distribution of monomeric insulin molecules, insulin dimers and higher-order oligomers. The term insulin dimer, when used absent any qualifying language, encompasses both insulin homodimers and insulin heterodimers. An insulin homodimer comprises two identical insulin polypeptides, whereas an insulin heterodimer comprises two insulin polypeptides that differ; an example of an insulin heterodimer would be provided by the association of a human insulin molecule with a bovine insulin molecule. As used herein, the term "covalent insulin dimer" designates two insulin molecules connected to each other by one or more a non-native covalent bonds; an example of such a bond would be an intermolecular disulfide bridge. Formation of covalent insulin dimers is known in the art as a mechanism of chemical degradation.

As used herein, the term "patient" without further designation is intended to encompass any warm-blooded vertebrate domesticated animal (including for example, but not limited to livestock, horses, cats, dogs and other pets) and humans.

The term "isolated" as used herein means having been removed from its natural environment. In some embodiments the analogue is made through recombinant methods wherein the analogue is isolated from the host cell, which typically may be a bacterial cell, yeast cell, inset cell or mammalian cell.

The term "purified" as used herein encompasses the isolation of a molecule or compound in a form that is substantially free of contaminants normally associated with the molecule or compound in a native or natural environment; in practice this means having been increased in purity as a result of being separated from other components of the original composition. The term "purified polypeptide" is used herein to describe a polypeptide which has been separated from other compounds including, but not limited to nucleic-acid molecules, lipids and carbohydrates.

Abbreviations

Insulin analogues will be abbreviated as follows:

The insulin A- and B chains will be designated by a capital A for the A chain and a capital B for the B chain wherein the following number (e.g., A0 or B0) will designate the base sequence is an insulin sequence (A chain: SEQ ID NO: 60, B chain SEQ ID NO: 61). Modifications that deviate from the native insulin are indicated in parenthesis following the designation of the A or B chain (e.g., [B(A5, D10,E16,V17):A(H8,Q18,G21)]) with the single-letter amino-acid abbreviation indicating the substitution and the number indicating the position of the substitution in the respective A or B chain, using native insulin numbering. A colon between the A and B chain indicates a two-chain insulin.

Embodiments

Figure 1:
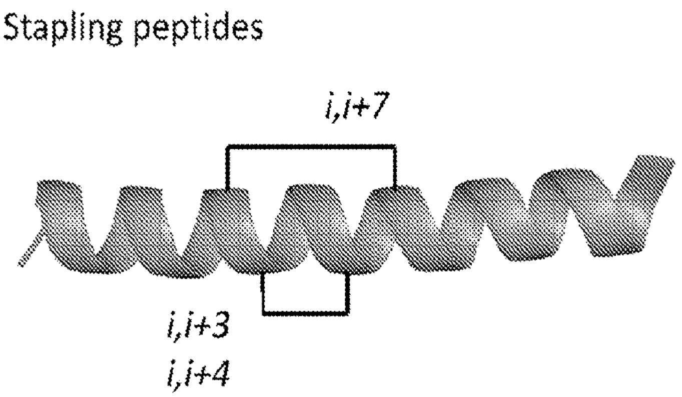
FIG. 1 is a schematic drawing of an α-helical ribbon and side-chain/side-chain "staples" exploiting (i, i+3), (i, i+4) or (i, i+7) structural relationships to constrain and so stabilize a segmental helical conformation.
Figure 2A:
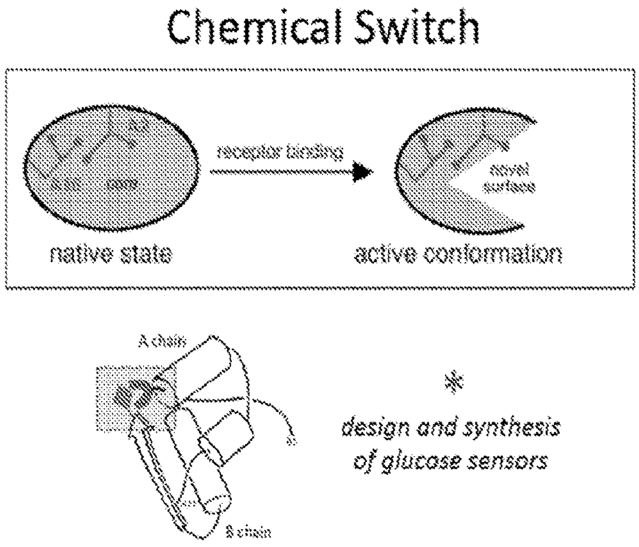
FIGS. 2A & 2B contrasts an intrinsic (or unimolecular) glucose-responsive insulin (GRI.
Figure 2B:
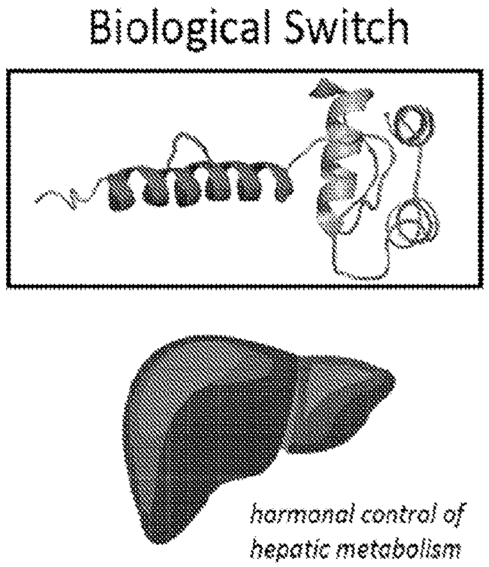

One embodiment of the present disclosure is directed to a class of glucagon analogues containing side-chain/side-chain tethers (or "staples"; FIG. 1) such that bioactivity is reduced or preserved whereas the peptide hormone's susceptibility to fibrillation is reduced. In another embodiment the stabilized glucagon analogues disclosed herein are used to form stapled N-terminal glucagon-insulin fusion proteins wherein the insulin moiety consists of an insulin analogue engineered to exhibit enhanced stability and shelf life, optionally wherein the fusion proteins are provided as a bioactive single polypeptide chain (FIG. 2, right). Because the latter single-chain insulin (SCI) analogues also exhibit markedly reduced susceptibility to fibrillation, the resulting fusion proteins exhibit dual protection from fibrillation via their N-terminal glucagon-like peptide moiety and their C-terminal SCI moiety. An essential feature of the fusion proteins is that its hormonal activity at the glucagon receptor is reduced relative to wild-type glucagon such that the respective glucagon-like and insulin-like activities of the fusion proteins recapitulate co-infusion of wild-type glucagon and wild-type insulin at molar ratios between 5:1 and 50:1.

In another embodiment, the stapled glucagon analogue is fused to a modified fibrillation-resistant two-chain insulin analogue, wherein said modifications include one or more of the following modifications: (a) removing residues at B-chain N Terminus (e.g., des-B1, des-B1,B2 or des-B1-B3, optionally including amino-acid substitutions at or adjoining the new N Terminus); (b) removing residues at the C Terminus of the B Chain, as exemplified by analogues known the art, such as "DesDi" (deletion of residues B29 and B30 with substitution LysB28) or des-B30 analogues; and (c) stabilizing substitutions positions B28, B29, A8, or A14 as known in the art; and (d) substitutions at A21 to avoid deamination of the native AsnA21 as known in the art.

Figure 3:
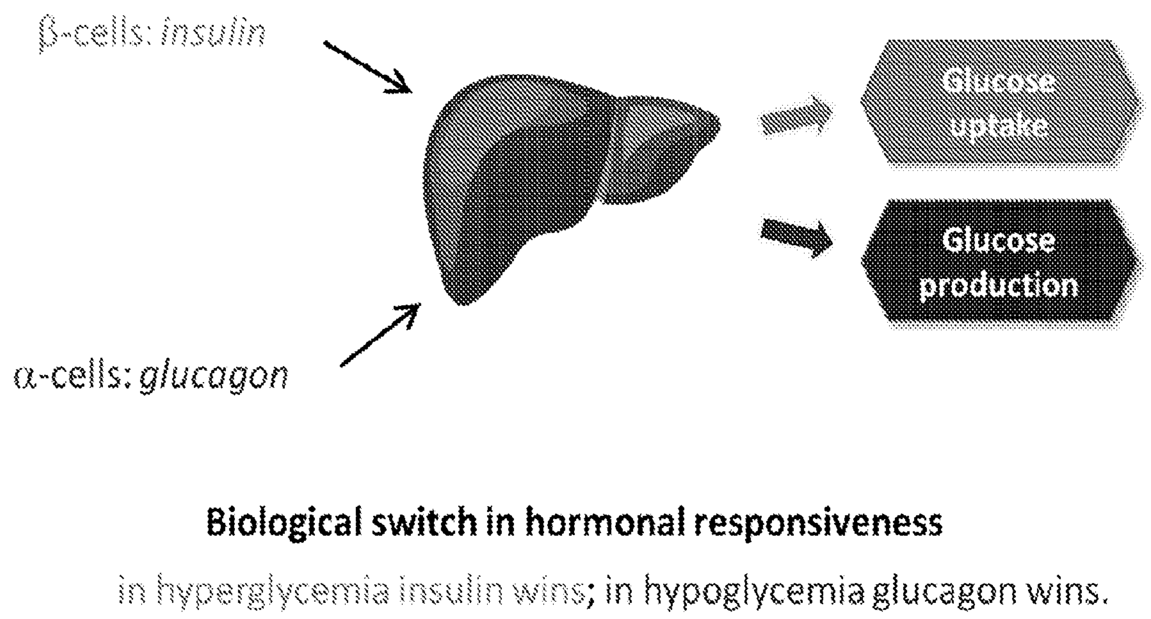
FIG. 3 is a schematic drawing of a physiological switch in the hormonal regulation of mammalian hepatic metabolism. Under hyperglycemic conditions, the liver is more responsive to insulin (the product of pancreatic β-cells) than to glucagon (the product of pancreatic α-cells); under hypoglycemic conditions, the pattern of hormonal responsiveness is the reverse.
Figure 4:
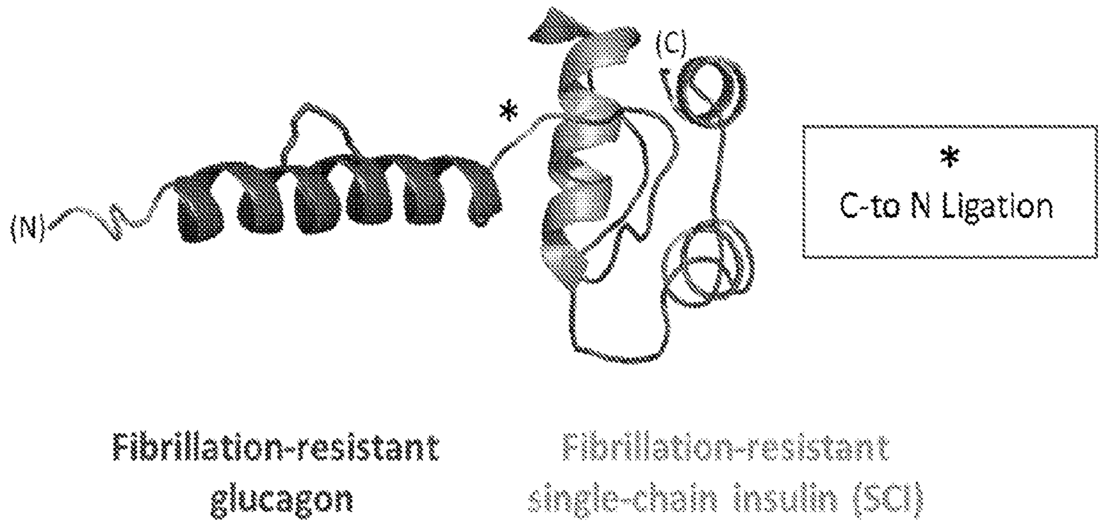
FIG. 4 is a schematic ribbon model of a glucagon-insulin fusion protein containing an N-terminal 13-17 side-chain/side-chain stapled glucagon analogue (α-helical ribbon; left side of molecule) and C-terminal single-chain insulin (SCI) analogue (three α-helical ribbons on right side of molecule). The glucagon analogue conforms to SEQ ID NO: 23. Asterisks indicate peptide bond between the C-terminal Lysine of an extended glucagon analogue and the N-terminal α-amino group of PheB1 in the SCI (57 residues with 6-residue C domain). Both glucagon and SCI can be prepared by chemical synthesis.
Figure 5:
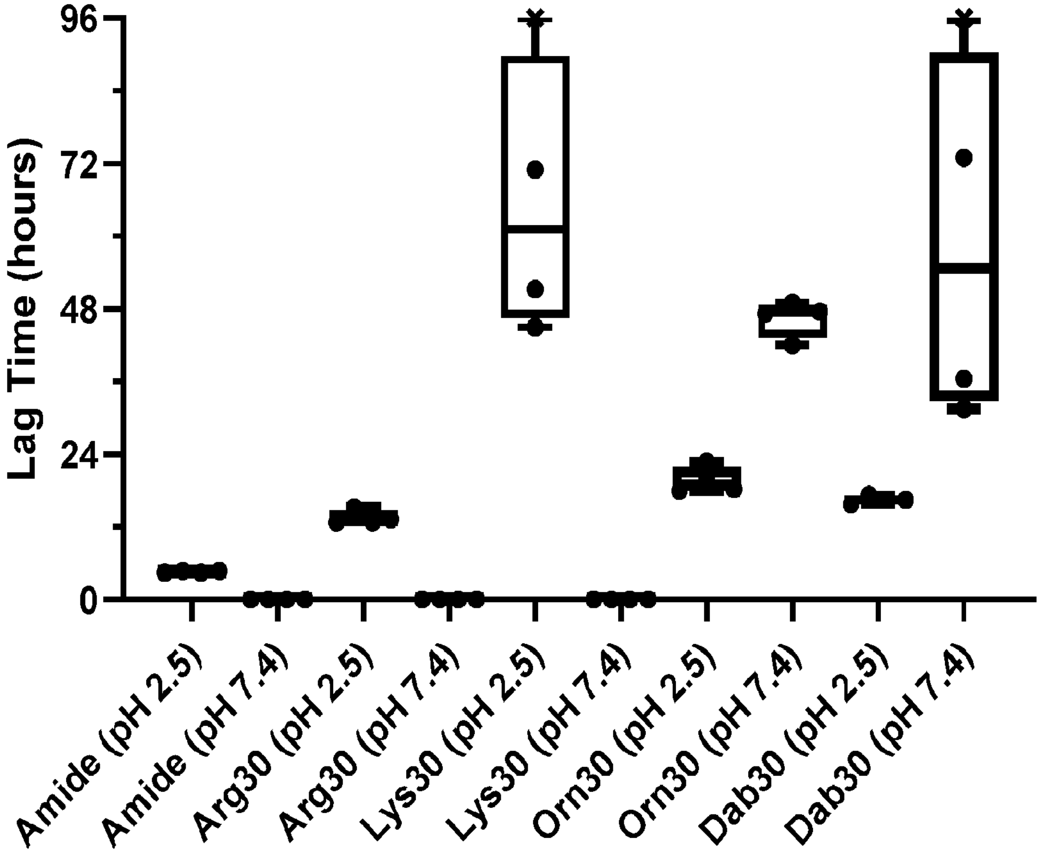
FIG. 5 provides the result of a fibrillation assay to a series of glucagon analogues containing a C-terminal basic residue relative to the C-terminal amide group of native glucagon. Basic residues Arg, Lys, Ornithine (Orn) or Di-aminobutyric Acid (Dab) were thus placed at position 30 and assayed at pH 2.5 and 7.4. A C-terminal positive charge was observed to delay fibril formation at pH 2.5; Orn and Dab also did likewise at pH 7.4. Fibrillation assays were performed at 37° C. and constant agitation on a 96-well plate automated reader. "X" represents a well that did not exhibit fibrillation within the duration of the experiment.
Figure 6:
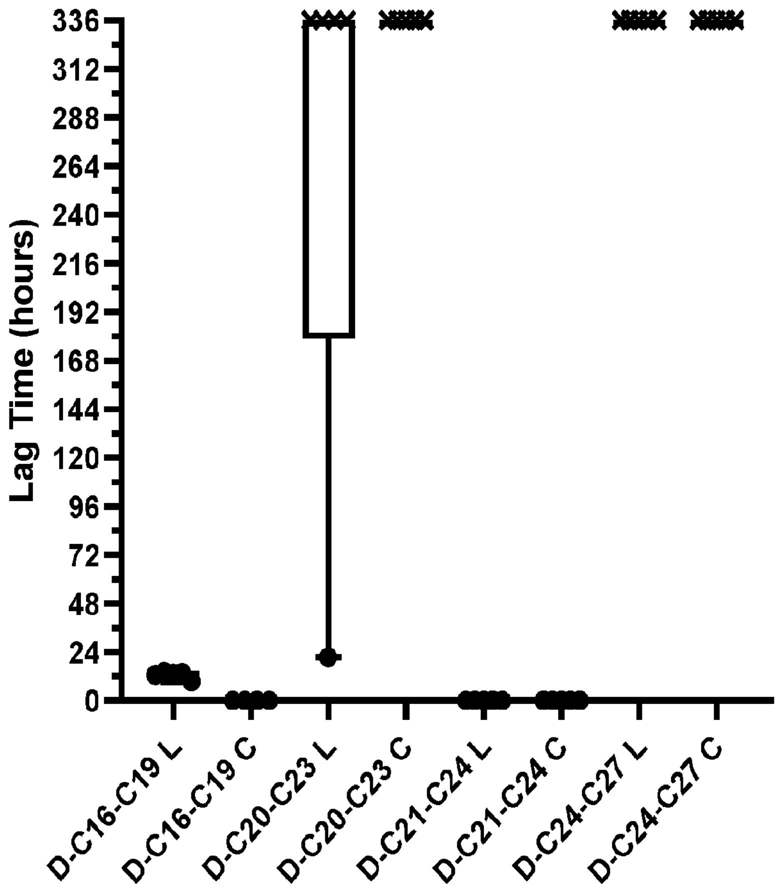
FIG. 6 illustrates a fibrillation assay done to a series of glucagon analogues containing pairwise a D-Cys at position i and an L-Cys at position i+3. These analogues also contained the modifications of Glucagon-EEK, enabling lag times to be compared to the results shown in FIG. 6. The analogues were dissolved in phosphate-buffered saline (pH 7.4) at a final peptide concentration of 100 μM. "L" analogues correspond to the linear form (i.e., without a disulfide bridge), whereas "C" analogues correspond to the oxidized peptide (containing a single disulfide bridge). Both L and C analogues [D-Cys20-Cys23] and [D-Cys24-Cys27] exhibited protection from forming fibrils that lasted for at least 2 weeks, except for one well on the linear [D-Cys20, Cys23] analogue. Fibrillation assay was done at 37° C. and constant agitation in a 96-well plate automated fluorescent plate reader; "X" represents a well that did not form fibrillation within the duration of the experiment.
Figure 7:
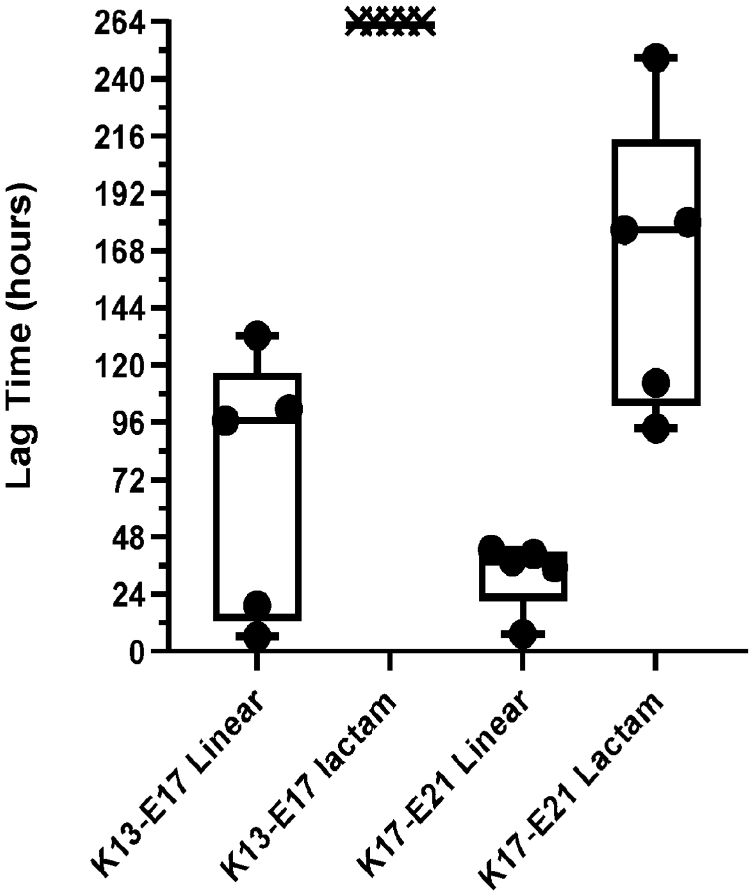
FIG. 7 provides the result of a fibrillation assay done to glucagon analogues containing the substitutions required to make a single side-chain to side-chain lactam bond between residues 13-17 or 17-21. The analogues were dissolved in phosphate-buffered saline (pH 7.4) at a final peptide concentration of 100 μM. These analogues contain the modifications of glucagon-EEK. The "Linear" analogues include the respective substitutions, namely [Lys13-Glu17] or [Lys17-Glu21], but not the side-chain lactam bond. "Lactam" analogues were constrained by side-chain/side-chain cyclization. The [Lys13-Glu17] lactam-constrained analogue (SEQ ID NO: 23) exhibited marked fibrillation resistance: no fibril formation was observed after 11 days. Fibrillation assays were done at 37° C. with constant agitation on a 96-well plate automated fluorescent reader; "X" represents a well that did not form fibrillation within the duration of the experiment.
Figures 8A, 8B:
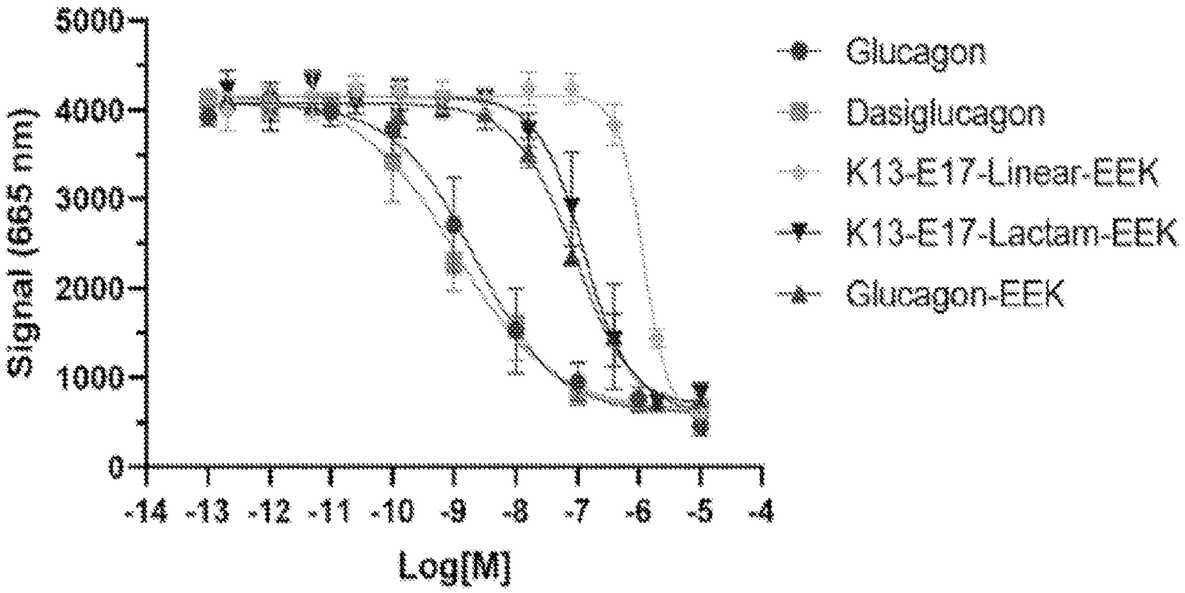
FIGS. 8A & 8B present the results obtained from a cell-based cyclic AMP (cAMP) activity assay performed using four glucagon analogues in relation to wild-type glucagon. HEK-293 cells overexpressing glucagon receptor were used. As shown in the cAMP production assay results presented in FIG. 8A, the signal at 665 nm is inversely proportional to amount of cAMP produced. Calculated $EC_{50}$ for the analogues tested are shown in FIG. 8B. Glucagon and dasiglucagon exhibited similar potencies (EC50 of 2.175 nM and 1.042 nM, respectively). The glucagon-EEK analogue (SEQ ID NO: 21), which carries Ornithine at positions 12, 17, and 18 and a C-terminal Glu-Glu-Lys extension, showed similar potency to an analogue carrying a [Lys13, Glu17] side-chain to side-chain lactam bond (SEQ ID NO: 23) (EC50 of 93.54 nM and 125.7 nM, respectively). The linear version of the [Lys13, Glu17] analogue exhibited markedly diminished potency, suggesting that the lactam bond was able to rescue the effect of these amino-acid substitutions on activity.
Figure 9:
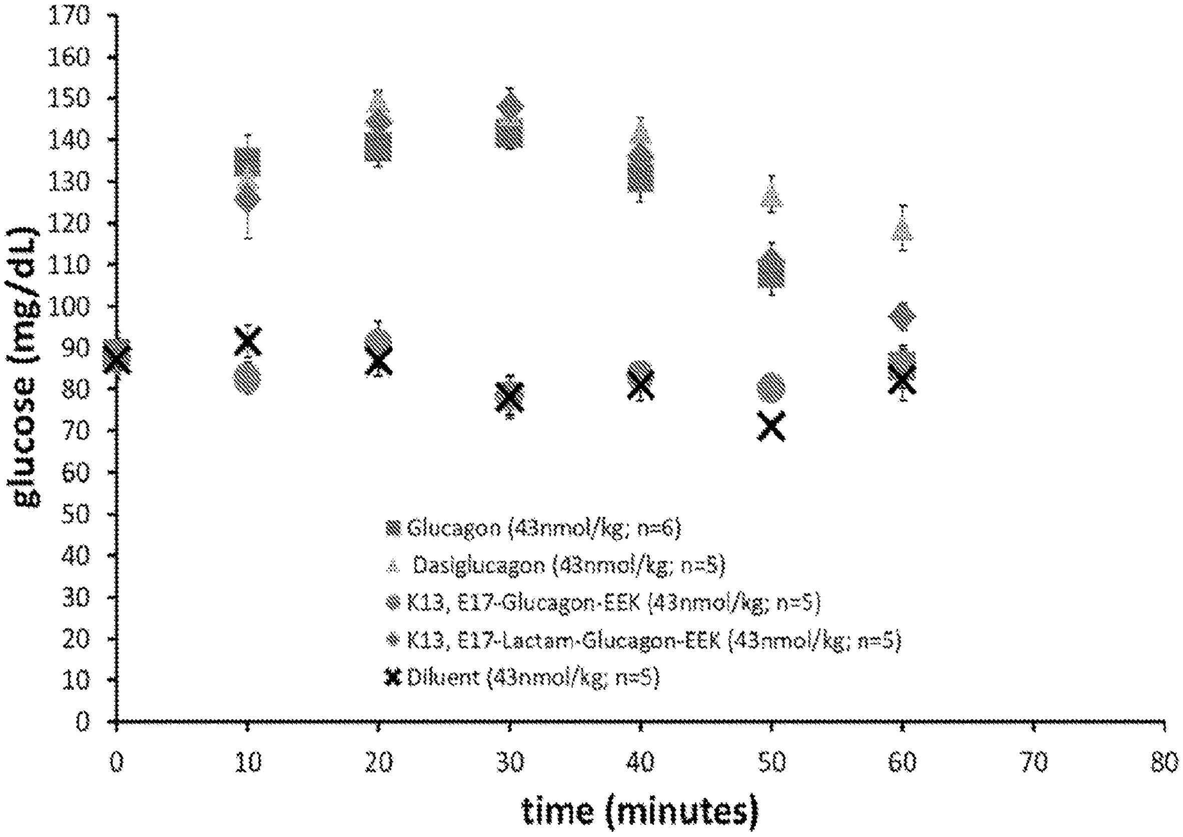
FIG. 9 shows an in vivo glucagon activity study done in normal rats. Four analogues were tested: wild-type glucagon, [Lys13, Glu17]-glucagon-EEK linear, [Lys13, Glu17-glucagon-EEK lactam (where "EEK" indicates C-terminal extension Glu-Glu-Lys) and dasiglucagon (Zealand Pharma). The data demonstrate that the linear analogue [Lys13, Glu17]-glucagon-EEK is inactive in rats. The 13-17 lactam bond rescued biological activity in vivo whereas the lactam-stabilized analogue (SEQ ID NO: 23) exhibited maximal activity, similar to that of glucagon or dasiglucagon.
Figure 10:
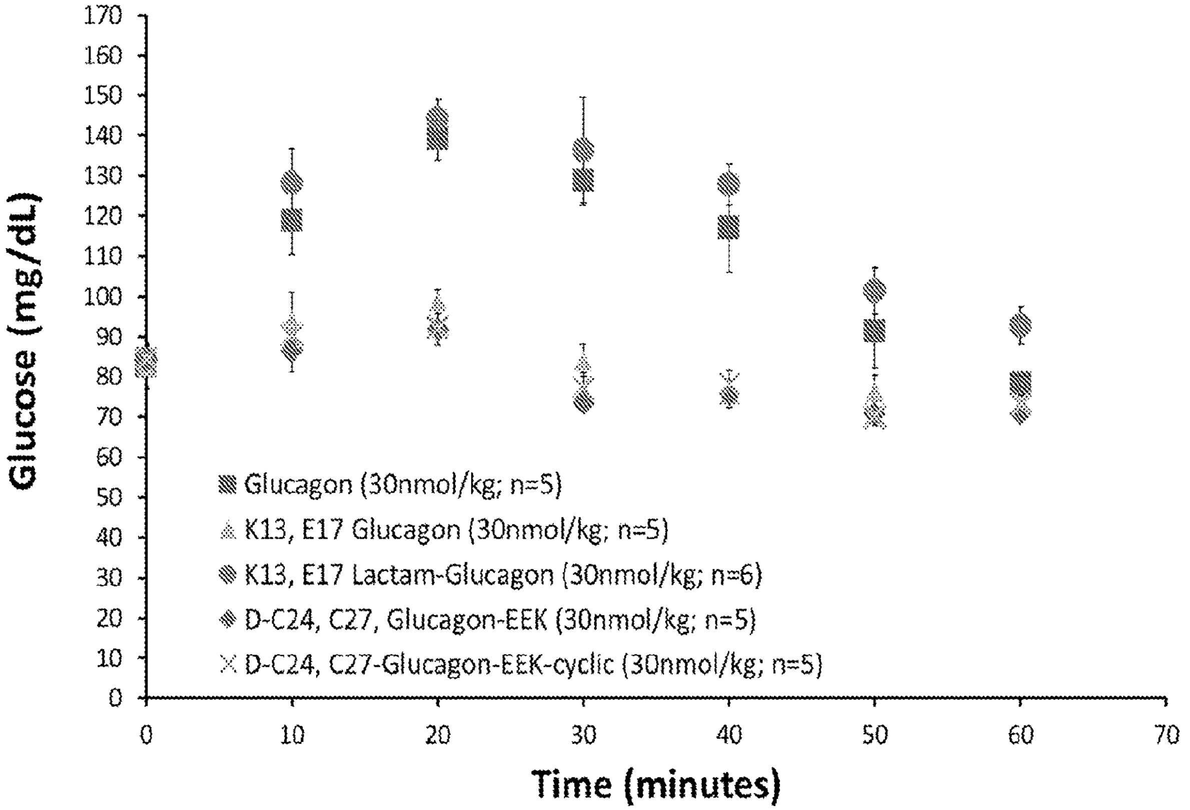
FIG. 10 presents an in vivo glucagon activity study performed in normal rats. Five analogues were tested: native glucagon, [D-Cys24, Cys27]-glucagon-EEK reduced (linear), -[Cys24, Cys27]-glucagon-EEK oxidized (cyclic) where "EEK" indicates C-terminal extension Glu-Glu-Lys, [Lys13, Glu17]-Glucagon linear, [Lys13, Glu17-glucagon lactam (SEQ ID NO: 10). These latter two analogues differ from those in FIG. 12 in that they do not contain Orn substitutions or C-terminal "EEK" extension. The data demonstrate that the only analogue that is active, other than wild-type glucagon, was the [Lys13, Glu17]-glucagon lactam, confirming that the lactam bond is required for the biological activity of this analogue and that its multiple modifications do not have a major impact on activity relative to wild-type glucagon.
Figure 11A:
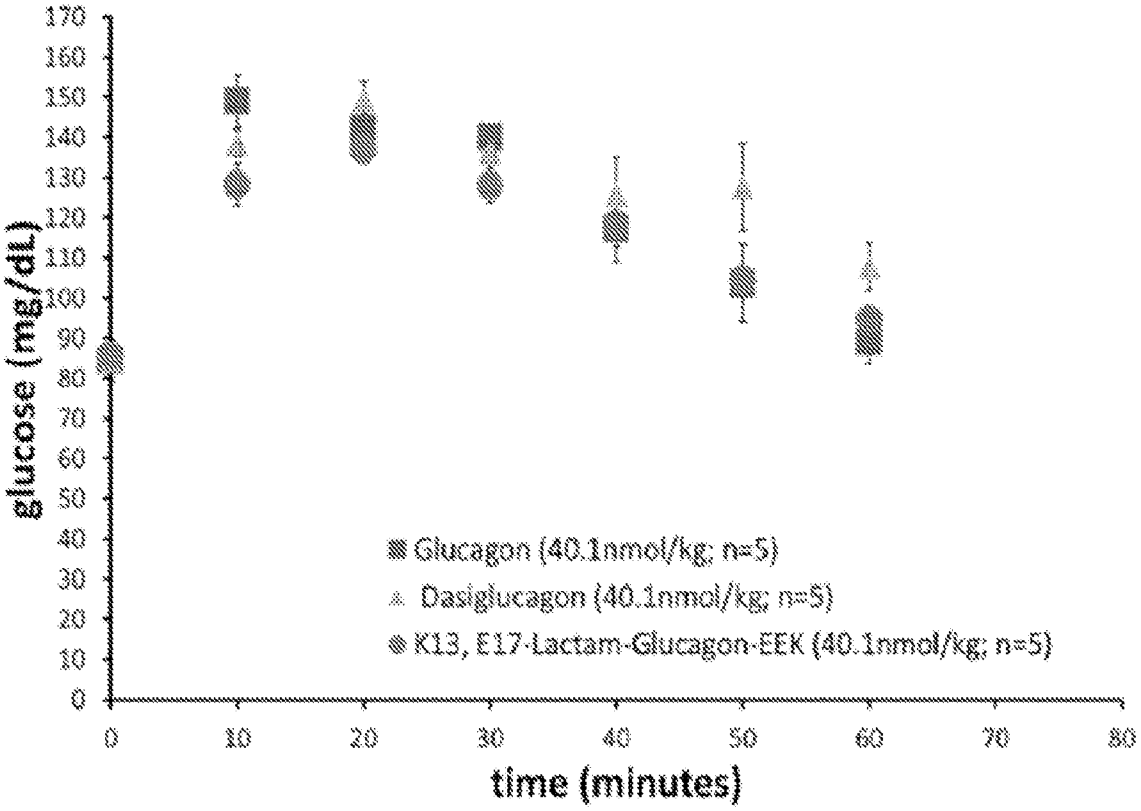
FIGS. 11A-11C illustrates results of stability assay comparing wild-type glucagon, dasiglucagon (Zealand Pharma) and the [Lys13, Glu17]-glucagon-EEK lactam analogue, where "EEK" indicates C-terminal extension Glu-Glu-Lys. In this assay the samples (made 150 μg/ml in 50 mM Tris buffer [pH 8.0]) were incubated at 37° C. with mild agitation and rotation for 14 days. Activities were then tested at three time points: t=0 (FIG. 11A), day 3 (FIG. 11B) and day 7 (FIG. 14C). Whereas native glucagon progressively lost activity, the [Lys13, Glu17]-glucagon-EEK lactam analogue of the present disclosure and dasiglucagon maintained full biological activity. Dasiglucagon is a fibrillation-resistant analogue in development by Zealand Pharma.
Figure 11B:
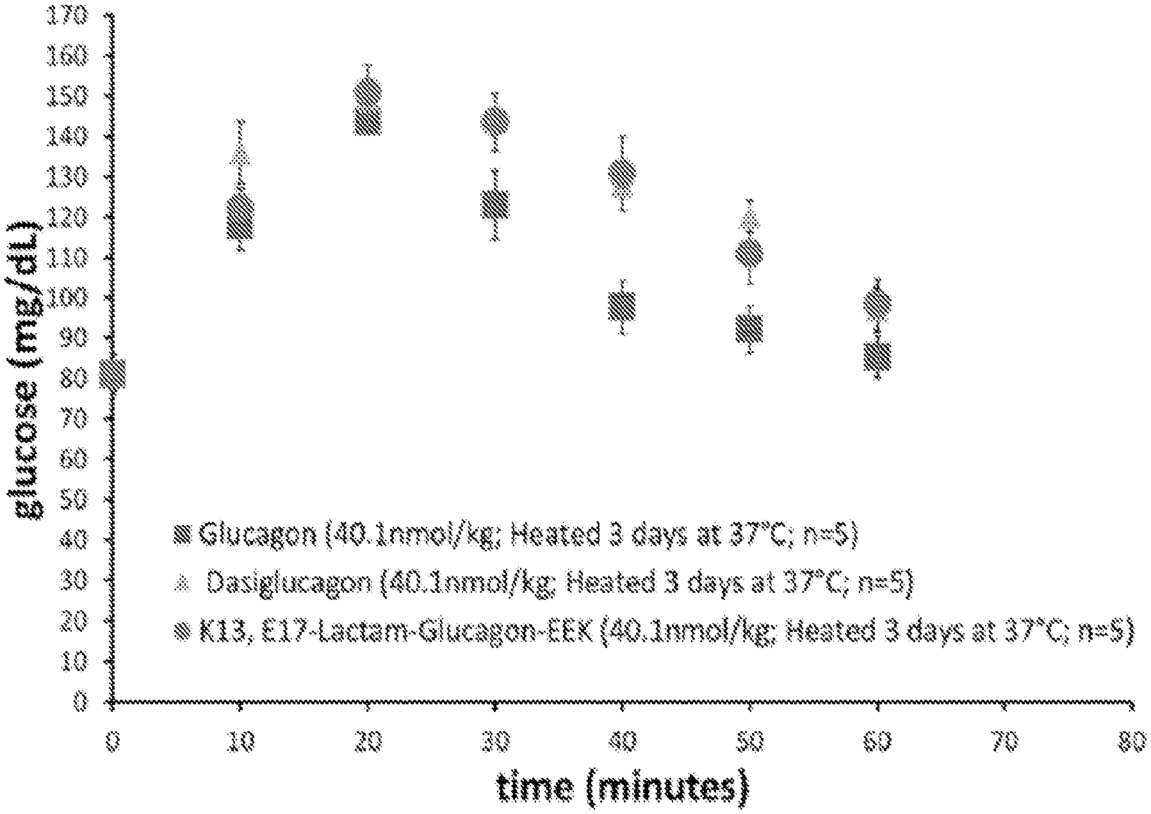
Figure 11C:
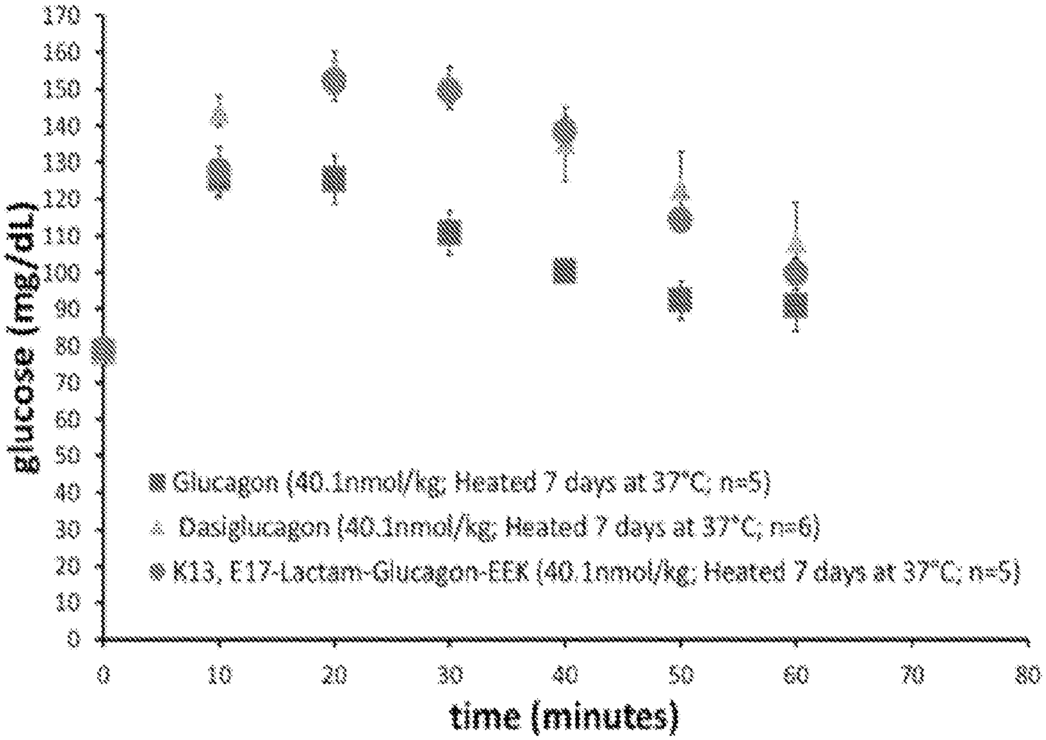
Figure 12A:
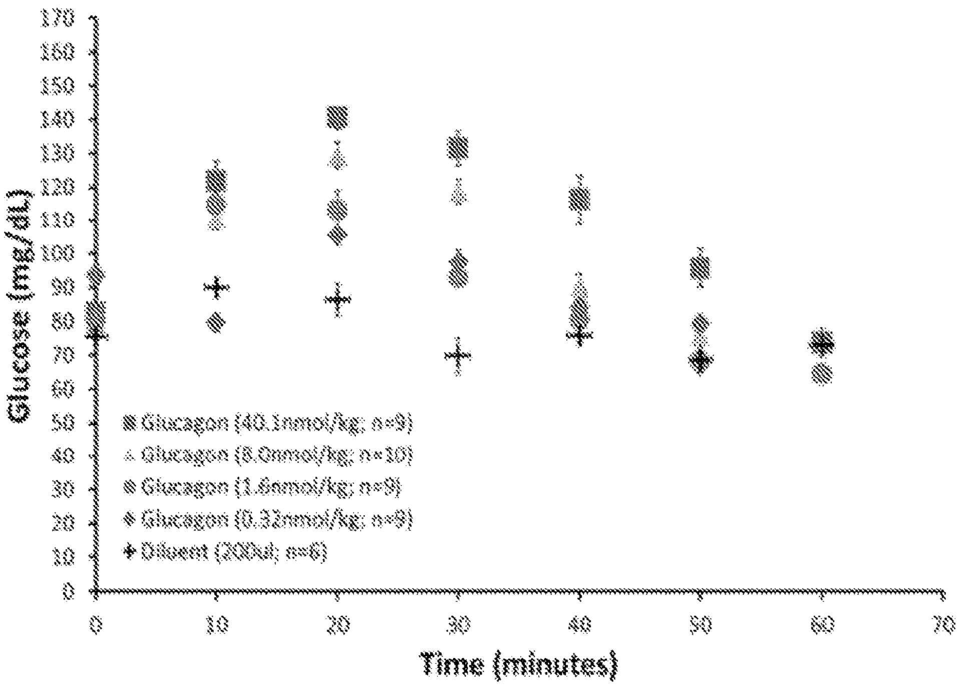
FIGS. 12A & 12B illustrate a dose-response study in normal rats using wild-type glucagon (SEQ ID NO: 1) (FIG. 12A) and [Lys13, Glu17]-Lactam-glucagon-EEK (SEQ ID NO: 23) (FIG. 12B) with four doses tested: 0.32, 1.6, 8 and 40 nmol/kg rat. Wild-type glucagon raised blood glucose levels in all four doses, whereas [Lys13, Glu17]-Lactam-glucagon-EEK did so only at the maximum dose (40 nmol/kg rat) with a minor raise at the 8 nmol/kg rat dose. This result, demonstrating a difference in potency, confirms the results shown in FIG. 8.
Figure 12B:
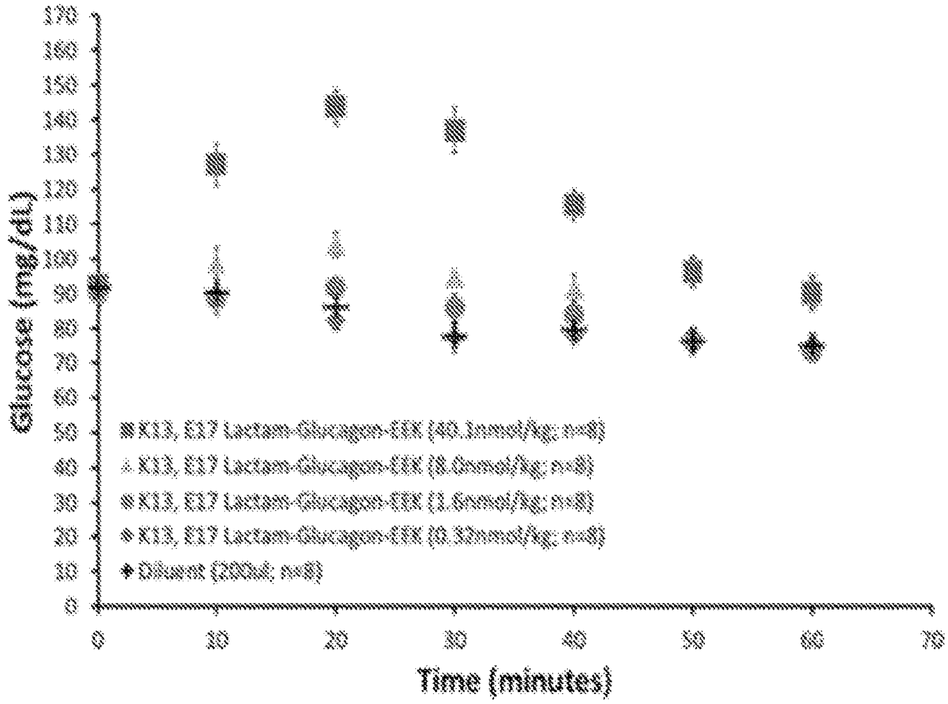
Figure 13:
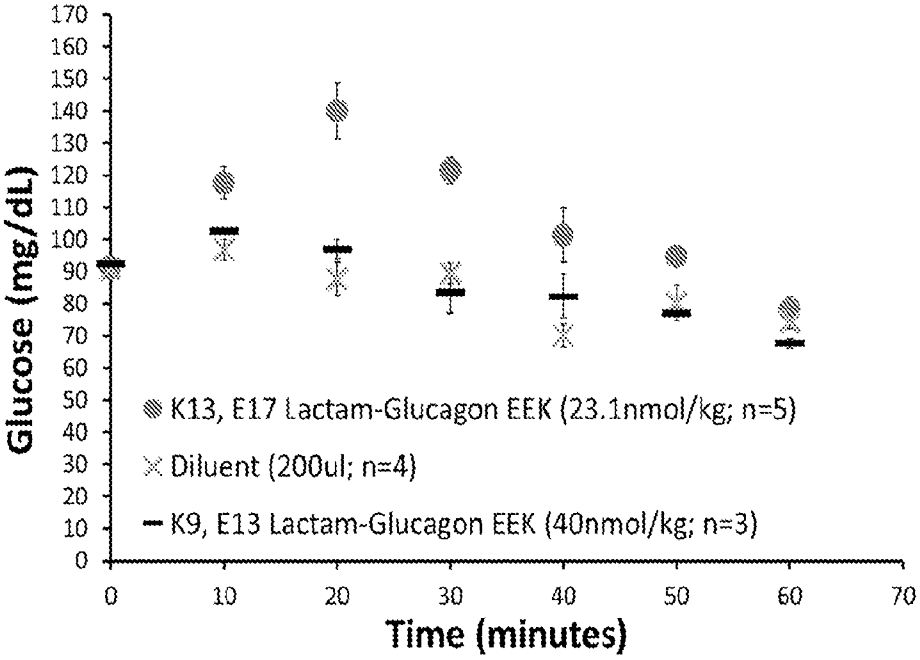
FIG. 13 shows an in vivo assay on normal rats through subcutaneous injection of the [Lys13, Glu17]-glucagon-EEK lactam analogue and the [Lys9, Glu13]-glucagon-EEK lactam analogue. These analogues exemplify active and inactive glucagon analogues, respectively, for subsequent use in ligation reactions to SCI or stabilized two-chain insulin analogues. The two analogues gave the expected responses.
Figure 14:
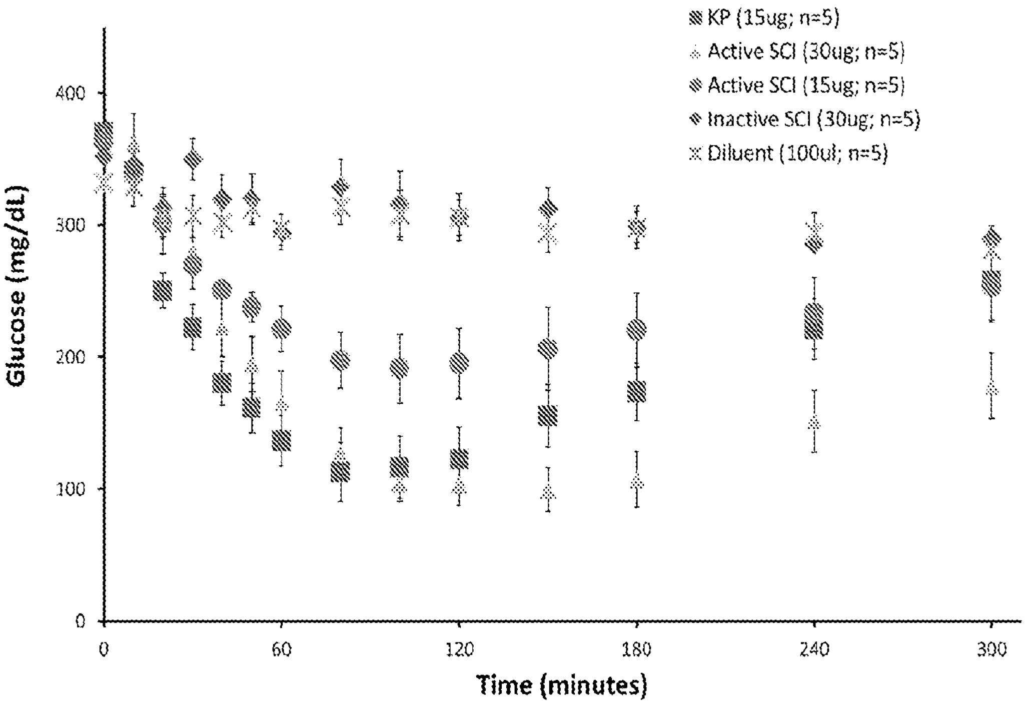
FIG. 14 shows the respective biological activities of an active SCI analogue (SEQ ID NO: 71) and an inactive SCI analogue ((SEQ ID NO: 72) relative to insulin Lispro (KP-insulin). The proteins were subcutaneously injected in STZ (diabetic) rats. A 30-μg dose of SCI had slightly higher activity than a 15-μg dose of KP-insulin.
Figure 15:
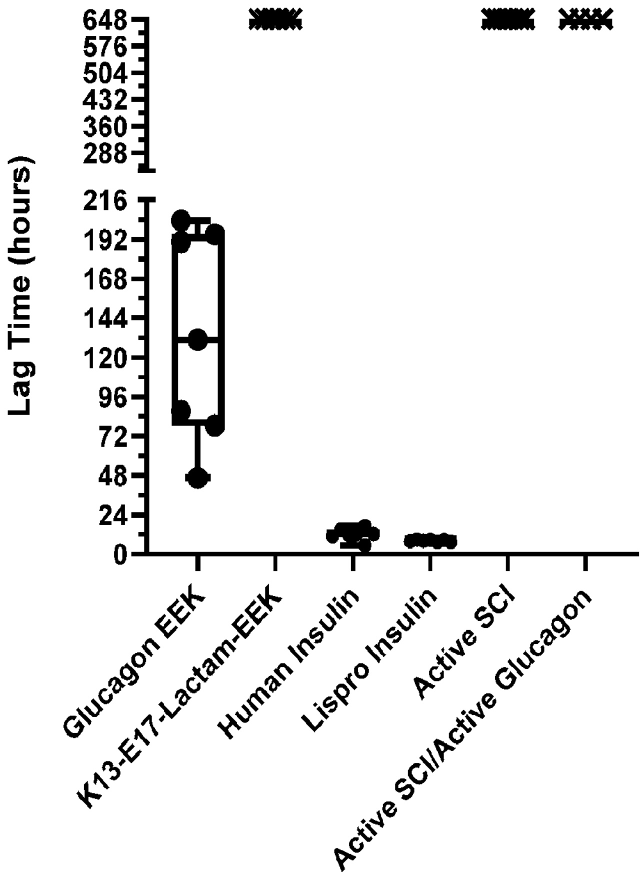
FIG. 15 presents a month-long fibrillation assay at 100 μM, pH 7.4 and 37° C. Glucagon-EEK (SEQ ID NO: 21), human insulin and insulin Lispro were used as controls; each formed amyloid-like fibrils. In contrast, [Lys13, Glu17]-Lactam-EEK (SEQ ID NO: 23), the active SCI (SEQ ID NO: 71) and their fusion protein (SEQ ID NO: 73) did not form amyloid-like fibrils within the duration of the experiment.
Figures 16A, 16B:
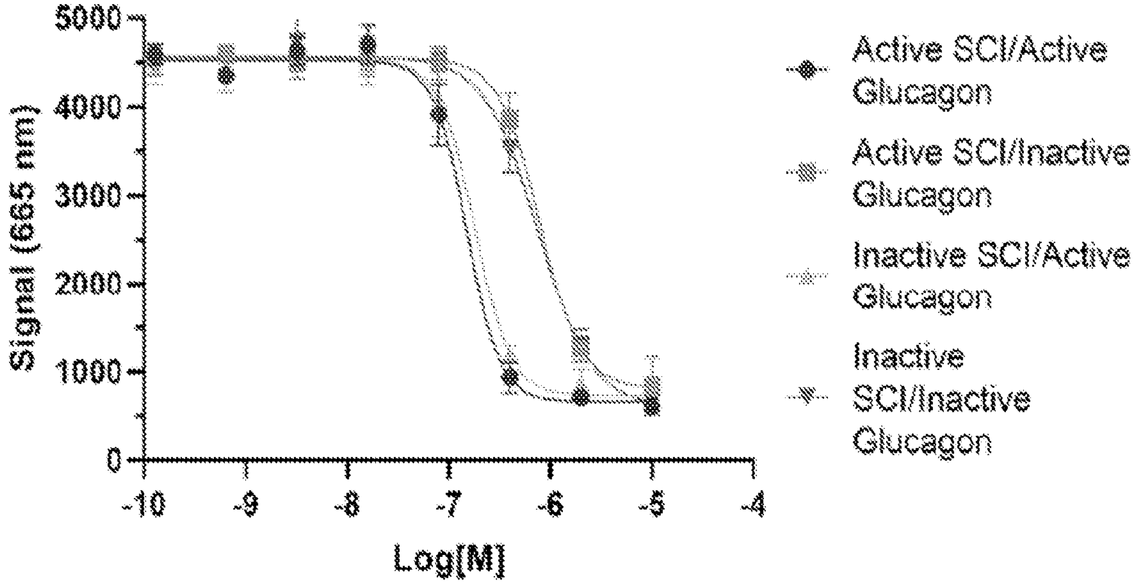
FIGS. 16A & 16B present data from a cell-based cAMP activity assay performed using four fusion proteins: two carrying an active glucagon analogue (SEQ ID NO: 73 and SEQ ID NO: 74)] and two carrying an inactive glucagon analogue (SEQ ID NO: 75 and 76.)
Figure 17:
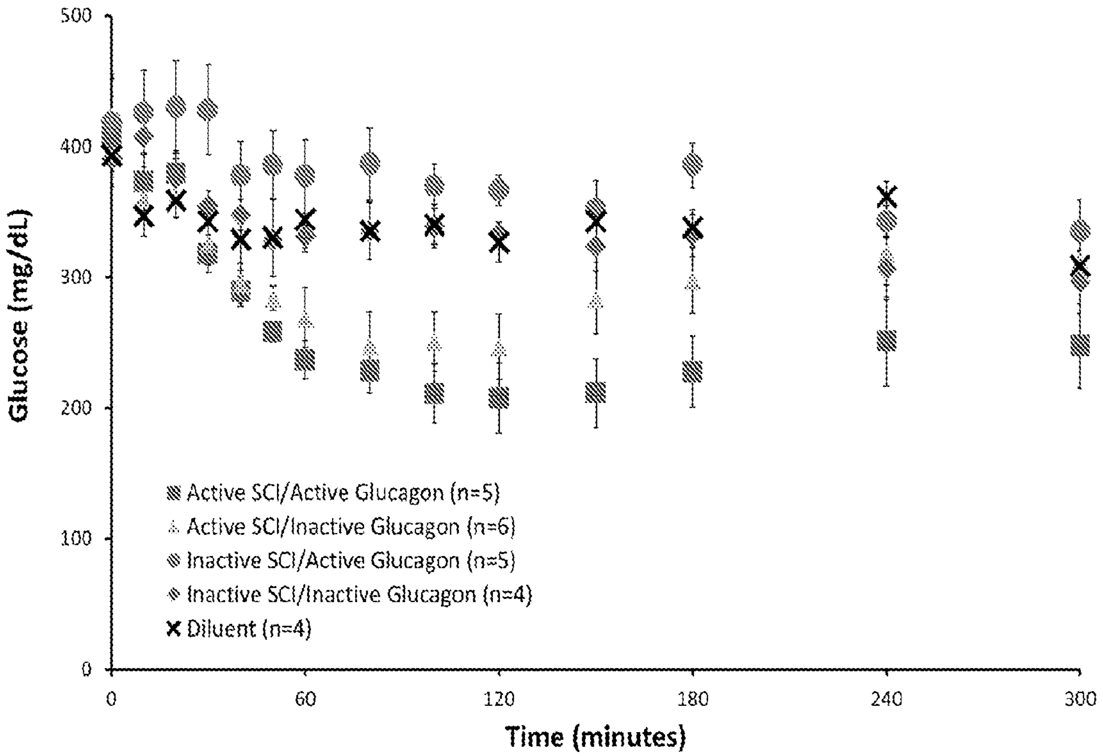
FIG. 17 presents an in vivo assay done in STZ rats. Four fusion proteins (active SCI/active Glucagon ■ (SEQ ID NO: 73), active SCI/inactive Glucagon ▲ (SEQ ID NO: 75), inactive SCI/active Glucagon ●(SEQ ID NO: 74), and inactive SCI/inactive Glucagon ◇ (SEQ ID NO: 76)) were subcutaneously injected at a dose of 12 nmol/kg per rat. As expected, the fusion protein carrying an inactive SCI and active glucagon gave rise to a slight rise in blood glucose levels. The analogue carrying both active versions exhibited a higher activity than the corresponding analogue containing an active SCI and inactive glucagon.

The glucagon analogues disclosed herein would, on their own, be useful in glucagon rescue kits (as a treatment for acute, severe hyperglycemia) and in one reservoir of a bihormonal pump designed to deliver glucagon and insulin in a closed-loop system for the automated treatment of diabetes mellitus. The stabilized glucagon-SCI (or glucagon-insulin analogue) fusion proteins are designed to regulate metabolism in diabetes mellitus such that the fusion proteins are effective to treat hyperglycemia whereas the glucagon-like moiety would mitigate risk of hypoglycemia. This dual mechanism of action exploits an endogenous biological switch in relative hormone responsiveness in the respective target organs of glucagon and insulin, principally in the liver (see FIG. 3). The disclosed glucagon analogues and glucagon-insulin fusion proteins thus each meet medical needs not optimally addressed by current technologies.

It is, therefore, an aspect of the present disclosure to provide glucagon analogues that contain at least one intra-chain staple exemplified by a lactam bridge between position 13 and position 17. Such a bridge requires pairwise substitution of the two native residues at these positions (respectively Tyr13 and Arg17; highlighted in bold in the sequence of wild-type human glucagon HSQGTFTSDYSKYLDSRRAQDFVQWLMNT; SEQ ID NO: 1). It is another aspect of the present invention to envision a 13-17 lactam bridge between an amino-acid component (such as Lys, Ornithine, 2,4-diaminobutyric acid, or 2,3-diaminopropionic acid) and a carboxcylic-acid component (such asAsp, Glu or α-aminoadipic acid) in any possible combination. It is yet another aspect of the present disclosure to combine the above 13-17 lactam bridge with other modifications either disclosed here or known in the art to forestall the fibrillation of glucagon. These include C-terminal basic amino-acid extensions of the glucagon sequence or introduction of a second side-chain/side-chain bridge at or near the C-terminal end of glucagon to initiate or further stabilize a segmental α-helical conformation. This bridge may be a salt bridge or a covalent linkage, such as a lactam or a variety of other covalent linkages, including but not limited to one of the following: disulfide bridge between D-Cysteine at position i and L-Cysteine or L-homocysteine at position (i, i+3), the corresponding diselenide bridge between D-Seleno-Cysteine at position i and an L-Seleno-Cysteine at position (i, i+3), or a stapled linkage between L-Cysteine at position i, and L-Cysteine at position i+7 via use of bifuctional bromoacetyl linkers cross linked by thiol alkylation using standard conditions to produce (FIGS. 19 and 20).

We engineered and embodied herein (i, i+3) Cys substitutions into glucagon (Seq IDs 14-20, 49-63, and 87-89), a design scheme that stems from recognition that disulfide cyclization between D-Cys (i) to Cys (i+3) was found to initiate α-helix formation in truncated parathyroid hormone-related protein (Pellegrini, 1997 *The Journal of Peptide Research,* 49(5), 404-414) and likewise as inhibitors of nuclear-receptor co-activator interactions (Galande 2005 *ChemBioChem,* 6(11), 1991-1998). It is yet another aspect of the present disclosure to stabilize a segmental α-helical conformation by modifying the above D-Cys/Cys (i, i+3) disulfide with an (i, i+3) spaced thioether-bridged amino acid, cystathionine, as a helix initiator wherein the i position is of D configuration and i+3 position is L configuration. Cystathionine is an unusual amino acid in which one sulfur atom with a methylene unit; this element is therefore non-symmetrical around the sulfur atom. Cystathionine has been introduced via base-assisted desulfurization as a redox-stable isostre of the cystine disulfide bridge for constraining short peptides in a helical conformation (Galande, 2004, *The Journal of Peptide Research,* 63(3), 297-302).

Figure 19:
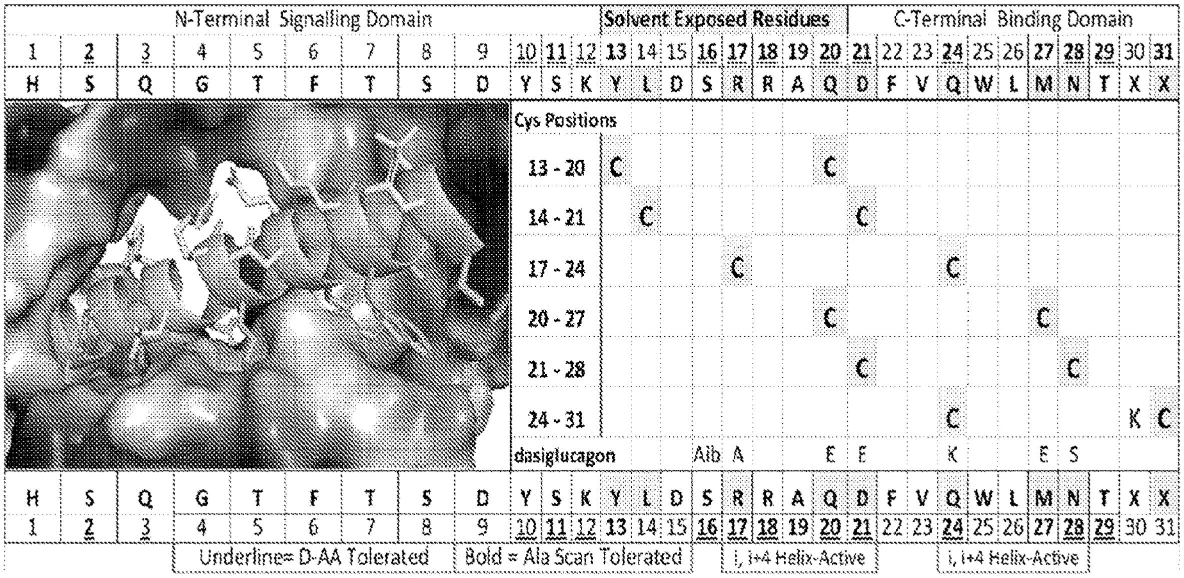
FIG. 19 illustrates the rationale for design and placement of Cys(i, i+7) substitutions for side-chain cross-linked (as thioether staples). An electrostatic map of glucagon/Gl-R complex (left panel) highlights the conformation of the bound hormone as an α-helix with solvent-exposed residues and buried residues. The numbering schemes denote previously reported structure-activity relationships wherein D-amino-acid substitutions and Alanine scanning demonstrated substitution tolerance and and sites conferring enhanced resistance to fibril formation. Also indicated are two areas where (i, i+4) lactam bridges [R17K-D21E] and [Q24K-N28E] stabilized bioactive structures (Ahn, et al., 2001, Blackwell et al., 2019). The right-hand panel shows positions in glucagon where Cys residues are replaced in an (i, i+7) arrangement to accommodate two turns of an α-helix (i.e., positions 13-20, 14-21, 17-24, 20-27, 21-28 and 24-31). These glucagon analogues where prepared by solid-phase peptide synthesis (SPPS) and purified as the reduced (linear) precursors (SEQ ID NO: 33-38).

The focus of this aspect of our design is to engineer Cys substitutions into an α-helix-specific (i, i+7) side-chain tether that allows placement of cross-linking (staples) into glucagon via use of bifuctional bromoacetyl linkers (FIG. 19 and FIG. 20). The (i, i+7) residues in an α-helical peptide are proximal in space but separated by two turns of the helix. Other examples to support our rationale for using linker-based Cys bridging include recent work wherein covalent Cys staples significantly improved the pharmacokinetic profile of Exendin-4 (Yang, 2016) and a strategy that allowed access to long-acting GLP-2 analogues that incorporated a serum protein binding motif (Yang, 2018, *J. Med. Chem.* 61(7):3218-3223). Other less attractive approaches are the synthetic olefin ring-closing metathesis-stapling strategy and the side-chain cyclic lactam (i,i+4) and (i,i+7) formation as applied to Class B GPCR ligands, including glucagon (Ahn, 2001, J. Med. Chem. 44 (19):3109-3116). We disclose herein six Cys(i, i+7) incorporations in the C-terminal half of glucagon. In accordance with previous studies of structure-activity-relationship (SAR) of Ala-scanning, D-amino-acid incorporations and (i, i+4) lactam-bridging, we anticipate that these analogues will demonstrate binding affinity and extend fibrillation lag times. We note that analogues c[C13-20] and c[Cys14-21 span the Aib16 site, which is an unnatural modification that significantly inhibits fibrillation; analogues, c[Cys17-24], c[Cys20-27], and c[Cyc21-28] substitute for native residues Q20, Q24, M27, and N28 that are known for their chemical instability. Finally, c[Cyc24-31] analogue extends the C-terminal by 2 residues K30, C31 to install a bridge at the C-terminal and thereby provides a K30 replacement that shown herein to inhibit fibrillation. These six analogues, thus prepared by solid-phase peptide synthesis (SPPS) and purified in their reduced (linear) forms, are amenable to cross-linking by thiol alkylation using standard conditions with bifunctional bromacetyl Orn (10 atom) linkers.

It is yet another aspect of the present disclosure to modify the non-bridged positions of the glucagon sequence to enhance local α-helical propensity, such as by substituting one or more β-branched amino acids by non-β-branched amino acids (excluding Cysteine, Glycine and Proline). In another facet of the present disclosure, the non-bridged positions of the glucagon sequence may be modified to enhance solubility and chemical physical stability, for instance, by replacing amino acids prone to chemical degradation (such as Asparagine, Glutamine, Methionine, Aspartic acid) or by replacing residues surrounding Aspartic acid by basic or acidic amino acids (such as Glutamic acid, Lysine, Arginine, Ornithine, Diamino-Butyric Acid or Diamino-Propionic Acid). In particular, modifications may be made at positions Gln3, Asp15, Ser16, Gln20, Asp21, Gln24, Met27, or Asn28 individually of in combination. The glucagon analogue may be further modified such that it contains a C-terminal Lysine but lacks any other Lysine or Arginine residue, such that the peptide lacks a tryptic cleavage site; this can be accomplished by replacing each internal Lysine or Arginine (excepting Lysines engaged in lactam-bridge formation) by Ornithine, Diamino-Butyric Acid or Diamino-Propionic Acid—basic residues not recognized by the active site of trypsin. The latter class of glucagon analogues may provide substrates for trypsin-catalyzed linkage of the unique C-terminal Lysine to the α-amino group at the N terminus of a single-chain or two-chain insulin analogue also modified to be without an internal tryptic site (below). It is an additional aspect of the present disclosure to modify in vitro affinities or in vivo activities of the 13-17 intra-chain-stapled glucagon analogues for glucagon receptor be in the range 1-200% relative to wild-type glucagon, with distinct applications pertaining to high-potency isolated glucagon analogs for use in rescue kits or pumps (relative glucagon activity 10-200%) versus pertaining to fusion proteins; in the latter the glucagon analogue motiety would exhibit reduced activity (1-20%) to allow unopposed action of the insulin moiety during hyperglycemia, but enough activity to prevent or mitigate hypoglycemia. This could be achieved by any of the previous modifications, including the intra-chain bridge, or by C-terminal extensions of the sequence that reduce potency.

It is another embodiment of the present disclosure to fuse stapled glucagon analogues containing the above 13-17 intra-chain bridge (and optionally other stabilizing substitutions or modifications) to an insulin analogue, a single-chain insulin (SCI) analogue with foreshortened C domain comprising 4-11 amino acids (Tables 1 and 2), or a modified fibrillation-resistant two-chain insulin analogue. The stapled glucagon-insulin fusion protein may contain a peptide bond between the C-terminal residue of the glucagon analogue and the N-terminal residue of the insulin conjugated using trypsin-mediated ligation or Sortase A ligation; or the peptide and protein may be connected by an unnatural linkage such as enabled by click chemistry. Although the preferred molecular embodiment of the insulin moiety in the fusion protein is an SCI owing to the extreme fibrillation resistance of this class of insulin analogues, the scope of the present disclosure includes fusion proteins wherein the N-terminal glucagon moiety is fused to residue B1, B2, B3 or B4 of an insulin B chain (or des-B1, des-[B1, B2], des-[B1-B3] B chain, optionally with amino-acid substitutions at or adjoining the new N Terminus) as part of a two-chain insulin analogue, preferably with stabilizing amino-acid substitutions at positions B29, A8 and/or A14 as are known in the art and with substitution of the chemically labile Asn at position A21 as known in the art. The latter two-chain insulin analogue may also have one- or two-residue C-terminal extensions of the A or B chains to modify the isoelectric point of the fusion protein via additional acidic- or basic residues.

The fusion proteins of the present disclosure may exhibit an isoelectric point (pI) in the range 4.0-6.0 and thereby be amenable to pharmaceutical formulation in the pH range 6.8-7.8; alternatively, the fusion proteins of the present disclosure may exhibit an isoelectric point in the range 6.8-7.8 and thereby be amenable to pharmaceutical formulation in the pH range 4.0-4.2. The latter conditions may lead to isoelectric precipitation in the subcutaneous depot as a mechanism of protracted action. Protracted action may also be affected by acylation of the SCI to mediate binding to albumin wherein the strength of albumin binding may be modulated, as is known in the art in the context of insulin analogues, by the length of the acyl group, the nature of the spacer element between acyl group and the attachment points on the SCI, and further by the use of a dicarboxylic acid as the acyl moiety.

In another aspect of the present disclosure the use of alternative strategies to the trypsin-mediated ligation method to make glucagon—SCI fusions is provided. These methods are novel in this context and allow fusion of the glucagon and SCI derivatives that are susceptible to detrimental trypsin cleavage and its ligation limitations. The first method claims use of Sortase A (Tsukiji and Nagamune, 2009) in a (SrtA)-mediated ligation to produce C→N-Terminal glucagon-SCI fusions, like trypsin, while providing novel access to fusion of glucagon C-terminal onto Lys sidechain position(s) in the SCI construct either in a 1:1, 2:1 or other multimeric ratios. Specifically, novel to this claim is that we recognize the C-terminal residues (LMNT; SEQ ID NO: 124) of glucagon share high similarity with the SrtA-recognizing sequence (LXXTG; SEQ ID NO: 125). This approach may also exploit engineered Sortases as developed to recognize different target sequences as exemplified by LAXTG (SEQ ID NO: 126) and LPXTG (SEQ ID NO: 127), LPXAG (SEQ ID NO: 128); these options provide flexibility to modify the glucagon sequence accordingly (Freund, C., & Schwarzer, D., 2021). We also recognize the functional group tolerance in glucagon C-terminal region for biological activity includes extensions and modifications of Met27. Therefore, one single M27P or M27A substitution added to a C-terminal triple Glycine extension on any of modified glucagon analogues can function as a SrtA ligation acceptors with $H_2N$-$G_n$-SCI analogues, to produce P27-glucagon-$G_n$-SCI fusions where "G" indicates one or more Glycine residues as determined by n=1, 2, 3, or 4 Gly residues (FIGS. 21 and 22). The second method follows the goal of biorthogonal conjugation of glucagon agonists to folded SCI derivatives. We envision using a strategy of inserting a covalent bridge between specific sites in the SCI, most notably LysB29 or other positions in the C Terminus of the insulin B-chain and/or also in the C-chain (e.g., B1, B2, B3, B28, B29, A14, or C1-6; the latter denotes the foreshorted connecting peptide between B- and A domains); this would be an intramolecular side-chain:side-chain crosslinking using (A) click chemistry by incorporation of a choice of propargylglycine, homopropargylglycine, beta-homopropargylglycine or propargyl linker groups along with Nγ-azido-L-2,4-diaminobutyric acid; 2-amino-5-azido-pentanoic acid, Nδ-azido-L-ornithine, Nε-azide-L-Lysine or azido linker group at paired sites in the glucagon or insulin components; or (B) Sortase-A ligation approaches by incorporation of a Sortase recognition sequence (LXXTG; SEQ ID NO: 125) on glucagon C-terminal and a Sortase acceptor sequence $(Gly)_n$ at B-chain N-terminal or linked at specific sidechain amino groups of (B1, B2, B3, B28, B29, A14, or C1-6). Click chemistry relies on a CuI-catalyzed Huisgen 1,3-dipolar cycloaddition reaction of azides and alkynes that leads to the formation of 1,4-disubstituted 1,2,3-triazoles, (Vsevolod, 2002; Tornoe, 2002). Click chemistry has been widely used in organic, medicinal and, especially, peptide chemistry because 1,2,3-triazoles present a motif with structural and electronic characteristics similar to those of the peptide bond.

It is an additional aspect of the present disclosure that absolute in vitro affinity or in vivo activity of the fusion protein for glucagon receptor be in the range 1-200% relative to wild-type glucagon and that the in vitro affinity or in vivo activity of the fusion protein for the insulin receptor (isoforms IR-A and IR-B) be in the range 1-200% relative to wild-type human insulin; the optimal activity of the glucagon analogue or moiety relative to wild-type glucagon depends on useage as above (i.e., whether as a stand-alone hormone or as part of a fusion protein). It is yet an additional aspect of the present disclosure that absolute in vitro affinities of the fusion protein for the Type 1 insulin-like growth factor receptor (IGF-1R) are in the range 5-200% relative to wild-type human insulin and that absolute in vitro affinities of the fusion protein for the glucagon-like peptide 1 (GLP-1) are in the range 1-200% relative to WT human glucagon.

It is yet another aspect of the present disclosure that favorable or unfavorable substitutions may be respectively introduced (a) into the lactam-stapled glucagon moiety and (b) into the SCI moiety to adjust the ratio of glucagon signaling activity to insulin signaling activity so as to coordinately co-optimize protection from hypoglycemia and treatment of hyperglycemia. In the case of the lactam-stapled glucagon moiety, the modifications may be a single substitution or a combination of replacements in residues known in the literature to decrease glucagon biological activity if changed, exemplified by alanine substitutions at residues 2, 16, 18, 20, 21, 24, 27, 28, 29 (Chabenne et al. 2014). On the other hand, the optimization for the SCI moiety may require substitutions in the A domain or B domain of the SCI known to attenuate insulin action as respectively exemplified by single amino-acid substitutions AlaA1, ThrA3, AlaA14, GlnA17, GlyA21, ThrB12, GlnB13, GluB16, LeuB24, HisB25 or LeuB26. The lactam-stapled glucagon moieties or the SCI moieties of the present disclosure may also contain a variety of other basic- or acidic amino-acid substitutions introduced to "tune" the overall isoelectric point of the lactam-stabilized glucagon-SCI fusion protein to be less than 5.5 or in the range 6.8-7.8; the lactam-stabilized glucagon may contain basic or acid substitutions in residues 3, 16, 18, 20, 21, 24, 27 and/or 28, while the SCI moiety may be modified in the A- or B domains or optionally basic- or acidic amino-acid substitutions in the foreshortened C domain. The SCI moiety may be further modified to contain a fourth disulfide bridge (such as between residues B4 and A10) to further forestall protein fibrillation.

Figure 18:
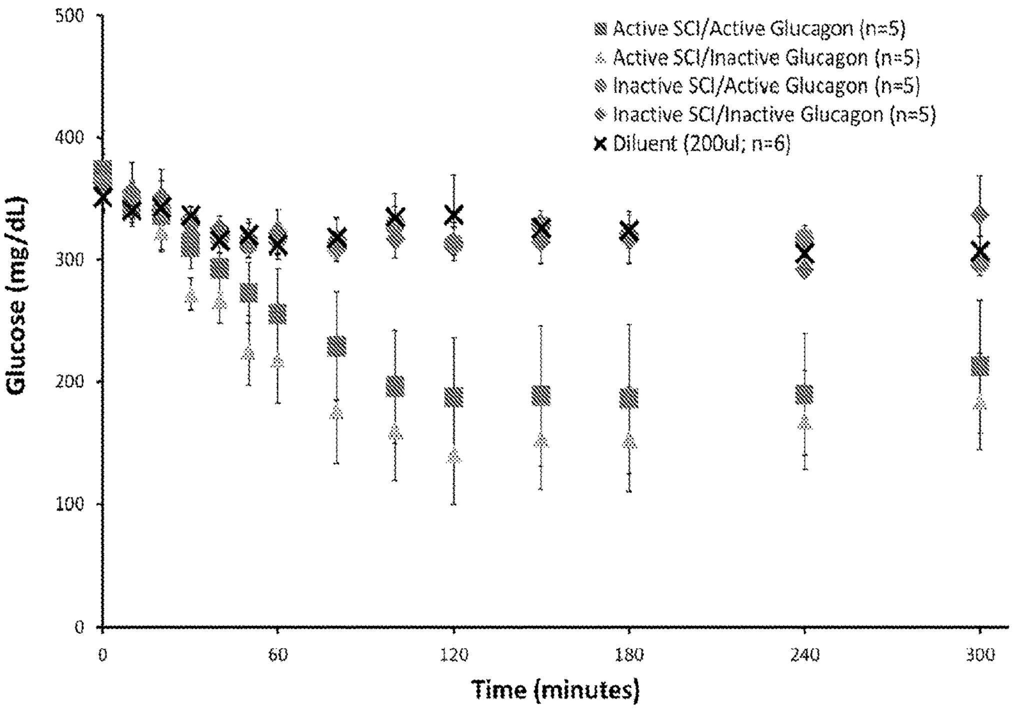
FIG. 18 presents another in vivo assay done in STZ rats. The four fusion proteins used in FIG. 17 were subcutaneously injected at doses of 23.8 nmol/kg per rat. The fusion protein carrying an inactive SCI and active glucagon didn't cause an increase in blood-glucose concentrations. In this study both fusion proteins carrying an active SCI analogue had similar activities. However, relative to the 12-nmol/kg rat doses (FIG. 17), one observes that the fusion protein carrying an inactive glucagon exhibited increased activity at the increased dose, whereas the version carrying an active glucagon stayed in a similar range. This result suggests a buffering capacity conferred by glucagon agonist activity under hypoglycemic conditions.

It is an additional aspect of the present disclosure that preparing glucagon-SCI fusions where the glucagon C-terminal is linked to sidechain Lys residues (either native or modified) in the SCI in a 1:1, 2:1 or other higher multimers to affects dual hormonal activities of the fusion. To disclose an alternative approach, and achieve the goal of biorthoganol conjugation of glucagon agonists to folded SCI derivatives, we envision using a strategy of inserting a covalent bridge between specific sites in the SCI, most notably LysB29 or other positions in the C Terminus of the insulin B chain and/or also in the C-chain an intramolecular side-chain:side-chain crosslinking using click chemistry or Sortase-A ligation approaches (FIG. 18). Click chemistry relies on a CuI-catalyzed Huisgen 1,3-dipolar cycloaddition reaction of azides and alkynes (Rostovtsev, 2002; Tornoe, 2002) and leads to the formation of 1,4-disubstituted 1,2,3-triazoles (Meldal, 2008) which has been widely used in organic, medicinal and, especially, peptide chemistry, because 1,2,3-triazoles present a motif with structural and electronic characteristics similar to those of the peptide bond.

Exemplary Embodiments

In accordance with embodiment 1, a stabilized glucagon analogue having a lower potency at the glucagon receptor than native glucagon is provided, wherein said glucagon analogue comprises an intrachain bridge between the side chains of amino acids located at position i and i+4, wherein i is an integer selected from the range of 13 to 34; and further modifications to the native glucagon sequence that decrease the potency of the glucagon analogue at the glucagon receptor, said modifications selected from i) 1-4 amino acid substitutions;

ii) a C-terminal extension of 1-7 amino acids, wherein said extension amino acids are selected from the group consisting of aspartic acid, glutamic acid, arginine, lysine, omithine, Diamino-Butyric Acid, Diamino-Proprionic Acid, histidine, asparagine, glutamine, serine, threonine and tyrosine; or iii) a combination of i) and ii).

In accordance with embodiment 2 a glucagon analogue of embodiment 1 is provided wherein the analogue comprises 1 or 2 Ornithine substitutions at positions 12 and/or 18.

In accordance with embodiment 3 a glucagon analogue of embodiment 1 or 2 is provided wherein the glucagon peptide comprises a C-terminal extension of 1-3 amino acids, wherein said extension amino acids are selected from the group consisting of aspartic acid, glutamic acid, arginine, lysine, histidine, asparagine, glutamine, serine, cysteine, threonine and tyrosine, glycine, proline and alanine, as well as unnatural amino acids omithine, 2,4-diaminobutyric acid, propargylglycine, homopropargylglycine, beta-homopropargylglycine, Nγ-Azido-L-2,4-diaminobutyric acid; 2-amino-5-azido-pentanoic acid, Nδ-azido-L-ornithine, Nε-azide-L-Lysine, optionally the extension amino acids are selected from the group consisting of aspartic acid, glutamic acid, arginine, lysine, ornithine, Diamino-Butyric Acid, and Diamino-Proprionic Acid.

In accordance with embodiment 4 a glucagon analogue of any one of embodiments 1-3 is provided wherein the glucagon peptide comprises i) 1-2 Orn amino acid substitutions at positions 12 and, 18; or ii) a C-terminal extension of 3 amino acids, Xaa1, Xaa2, Xaa3, wherein Xaa1 is an amino acid selected from the group consisting of Ala, Gly, Glu, Arg, Lys, Orn, Diamino-Butyric Acid and Diamino-Proprionic Acid;

Xaa2 is an amino acid selected from the group consisting of Gly, Ala, Ser, Gln and Glu;

Xaa3 is an amino acid selected from the group consisting of Arg, Lys, Orn, Diamino-Butyric Acid and Diamino-Proprionic Acid, optionally wherein Xaa3 is Lys or Arg; or iii) a combination of i) and ii).

In accordance with embodiment 5 a glucagon analogue of any one of embodiments 1-4 is provided wherein the intrachain bridge is a lactam, however in alternative embodiments, this covalent bond joining the two amino acid side chains is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

In accordance with embodiment 6 a glucagon analogue of any one of embodiments 1-4 is provided wherein the intrachain bridge is a lactam formed between the side chains of a first amino acid selected from Lys, Ornithine, 2,4-diaminobutyric acid, and 2,3-diaminopropionic acid, and a second amino acid selected from Asp, Glu, α-aminoadipic acid, optionally wherein the first amino acid is lysine and the second amino acid is glutamic acid.

In accordance with embodiment 7 a glucagon analogue of any one of embodiments 1-6 is provided wherein the glucagon peptide further comprises a second intrachain bridge between the side chains of amino acids located at position i and i+4, wherein i is an integer selected from the range of 20 to 26.

In accordance with embodiment 8 a glucagon analogue of any one of embodiments 1-6 is provided wherein the glucagon peptide further comprises a second intrachain bridge between the side chains of amino acids located at position i and i+7 wherein i is an integer selected from the range of 21 to 24.

In accordance with embodiment 9 a glucagon analogue of embodiment 7 is provided wherein the first and second intrachain bridges are both lactam bridges, formed between the side chains of a first amino acid selected from Lys, Ornithine, 2,4-diaminobutyric acid, and 2,3-diaminopropionic acid, and a second amino acid selected from Asp, Glu, α-aminoadipic acid, optionally wherein the first amino acid is lysine and the second amino acid is glutamic acid.

In accordance with embodiment 10 a glucagon analogue of embodiment 7 is provided wherein the first intrachain bridge is a lactam bridge, optionally formed between a lysine and glutamic acid and the second intrachain bridge is a disulfide bridge, optionally formed between a D-Cys and an L-Cys.

In accordance with embodiment 11 a glucagon analogue of embodiment 8 is provided wherein the first intrachain bridge is a lactam bridge, optionally formed between a lysine and glutamic acid and the second intrachain bridge is a disulfide bridge, optionally formed between two cysteine amino acids, optionally via a bifunctional linker.

In accordance with embodiment 12 a glucagon analogue of any one of embodiments 1-11 is provided wherein the first lactam bridge is a lactam formed between amino acids at positions 13 and 17.

In accordance with embodiment 13 a glucagon analogue of any one of embodiments 1-12 is provided wherein said glucagon analogue comprise a side-chain/side-chain lactam bridge between a lysine introduced at position 13 and a glutamic acid introduced at position 17.

In accordance with embodiment 14 a glucagon analogue of any one of embodiments 1-13 is provided wherein said glucagon analogue comprises a C-terminal extension of 1-3 basic amino acids.

In accordance with embodiment 15 a glucagon analogue is provided comprising the sequence of any one of the peptides of SEQ ID NOs: 2-59, 67-70 and 78-114.

In accordance with embodiment 16 a glucagon analogue of any one of embodiments 1-15 is provided wherein the glucagon analogue is further modified to contain up to 3 residue modifications at non-bridged positions 3, 16, 20, 21, 24, 27 or 28 where the native residue is replaced by Glu, Lys, Arg, Orn, Diamino-Butyric Acid or Diamino-Proprionic Acid.

In accordance with embodiment 17 a fusion protein comprising an N-terminal glucagon analogue of any one of embodiments 1-16 and a C-terminal insulin analogue, preferably a single-chain insulin (SCI) analogue is provided, wherein a peptide bond or non-peptide spacer element connects the C-terminal residue of the glucagon analogue to the N-terminal residue of the SCI and wherein the C domain of the SCI (linking the B chain to the A chain) contains 4-11 amino acids.

In accordance with embodiment 18 a fusion peptide is provided, comprising a stabilized glucagon analogue having a lower potency at the glucagon receptor than native glucagon, wherein said glucagon analogue comprises an intrachain bridge between the side chains of amino acids located at position i and i+4, wherein i is an integer selected from the range of 13 to 28; and further modifications to the native glucagon sequence that decrease the potency of the glucagon analogue at the glucagon receptor, said modifications selected from i) 1-4 amino acid substitutions;

ii) a C-terminal extension of 1-7 amino acids, wherein said extension amino acids are selected from the group consisting of aspartic acid, glutamic acid, arginine, lysine, histidine, asparagine, glutamine, serine, cysteine, threonine and tyrosine, glycine, proline and alanine, as well as unnatural amino acids ornithine, 2,4-diaminobutyric acid, propargylglycine, homopropargylglycine, beta-homopropargylglycine, Nγ-Azido-L-2,4-diaminobutyric acid; 2-amino-5-azido-pentanoic acid, Nδ-azido-L-ornithine, Nε-azide-L-Lysine, optionally wherein said extension amino acids are selected from the group consisting of aspartic acid, glutamic acid, arginine, lysine, ornithine, Diamino-Butyric Acid, Diamino-Proprionic Acid, histidine, asparagine, glutamine, serine, threonine and tyrosine; or iii) a combination of i) and ii); and an insulin peptide comprising an A chain and a B chain, wherein said glucagon analogue is covalently linked to said insulin peptide, optionally via a linker.

In accordance with embodiment 19, a fusion peptide of embodiment 18 is provided wherein said insulin peptide is a single-chain insulin analogue comprising an A chain, a B chain and a single-chain linking peptide wherein the C Terminus of the B chain is covalently linked to the N Terminus of the A chain via the linking peptide.

In accordance with embodiment 20, a fusion peptide of embodiment 18 or 19 is provided wherein the C Terminus of the glucagon analogue is covalently linked to the N-terminal alpha amine of said insulin peptide or to the side chain of an amino acid of insulin at position B1, B2, B3 or any amino acid of the single-chain linking peptide of a single-chain insulin analogue.

In accordance with embodiment 21, a fusion peptide of any one of embodiments 18-20 is provided wherein the intrachain bridge is a di-sulfide bridge formed between a thiol bearing D-amino acid at position i, and a thiol bearing L-amino acid at position i+3, optionally wherein the D-amino acid is dCys and the thiol bearing L-amino acid is Cys, wherein i is an integer selected from the range of 13 to 30.

In accordance with embodiment 22, a fusion peptide of any one of embodiments 18-21 is provided wherein the intrachain bridge is a lactam bridge formed between the side chains of two amino acids, optionally the lactam is formed between the side chains of a Lys and a Glu amino acid.

In accordance with embodiment 23, a fusion peptide of any one of embodiments 18-22 is provided wherein the intrachain bridge is a lactam bridge formed between the side chains of a Lys at position 13 and a Glu at position 17.

In accordance with embodiment 24, a fusion peptide of any one of embodiments 18-23 is provided wherein the intrachain bridge is a lactam bridge formed between the side chains of a first amino acid located at position 13 and selected from the group consisting of Lys, Ornithine, 2,4-diaminobutyric acid, and 2,3-diaminopropionic acid and a second amino acid located at position 17 and selected from the group consisting of Asp, Glu and α-aminoadipic acid.

In accordance with embodiment 25, a fusion peptide of any one of embodiments 18-24 is provided wherein the intrachain bridge is a lactam bridge, formed between the side chains of a first amino acid located at position 17 and selected from the group consisting of Lys, Ornithine, 2,4-diaminobutyric acid, and 2,3-diaminopropionic acid and a second amino acid located at position 13 and selected from the group consisting of Asp, Glu and α-aminoadipic acid In accordance with embodiment 26, a fusion peptide of any one of embodiments 18-25 is provided wherein the modifications to the native glucagon sequence that decrease the potency of the glucagon analogue are selected from i) 1-2 Orn amino acid substitutions at positions 12 and, 18;

ii) a C-terminal extension of 1-3 amino acids, wherein said extension amino acids are selected from the group consisting of aspartic acid, glutamic acid, arginine, lysine, histidine, asparagine, glutamine, serine, cysteine, threonine and tyrosine, glycine, proline and alanine, as well as unnatural amino acids ornithine, 2,4-diaminobutyric acid, propargylglycine, homopropargylglycine, beta-homopropargylglycine, Nγ-Azido-L-2,4-diaminobutyric acid; 2-amino-5-azido-pentanoic acid, Nδ-azido-L-ornithine, Nε-azide-L-Lysine, optionally the extension amino acids are selected from the group consisting of aspartic acid, glutamic acid, arginine, lysine, ornithine, Diamino-Butyric Acid, and Diamino-Proprionic Acid, optionally the extension amino acids are selected from aspartic acid, glutamic acid, arginine, lysine and ornithine, optionally the extension amino acids are selected from aspartic acid, glutamic acid, lysine and ornithine.

In accordance with embodiment 27, a fusion peptide of any one of embodiments 18-26 is provided wherein the modifications to the native glucagon sequence that decrease the potency of the glucagon analogue are selected from i) 1-2 Orn amino acid substitutions at positions 12 and, 18;

ii) a C-terminal extension of 3 amino acids, Xaa1, Xaa2, Xaa3, wherein

Xaa1 is an amino acid selected from the group consisting of Ala, Gly, Glu, Arg, Lys, Orn, Diamino-Butyric Acid and Diamino-Proprionic Acid;

Xaa2 is an amino acid selected from the group consisting of Gly, Ala, Ser, Gln and Glu;

Xaa3 is an amino acid selected from the group consisting of Arg, Lys, Orn, Diamino-Butyric Acid and Diamino-Proprionic Acid, optionally wherein Xaa3 is Lys or Arg; or iii) a combination of i) and ii).

In accordance with embodiment 28, a fusion peptide of any one of embodiments 18-27 is provided wherein the carboxyl terminal amino acid is covalently linked to the N-terminus of the insulin B chain via a peptide bond, optionally via a fusion peptide linker.

In accordance with embodiment 29, a fusion peptide of any one of embodiments 18-28 is provided wherein the stabilized glucagon analogue has lower potency than native glucagon at the glucagon receptor, wherein said glucagon analogue comprises an amino acid sequence of HSQGTFTSDYS$X_{12}$$X_{13}$LDS$X_{17}$$X_{18}$AQDFVQWL$X_{27}$NT-$R_{30}$ (SEQ ID NO: 118);

wherein $X_{12}$ is Tyr or Orn;

$X_{13}$ and $X_{17}$ are amino acids whose side chains are covalently linked to form an intrachain bridge $X_{18}$ is Arg or Orn;

$X_{27}$ is Met or Pro; and $R_{30}$ is a C-terminal extension of 1-7 amino acids, wherein said extension amino acids are selected from the group consisting of aspartic acid, glutamic acid, arginine, lysine, histidine, asparagine, glutamine, serine, threonine and tyrosine; and a single-chain insulin analogue comprising an A chain, a B chain and a single-chain linking peptide wherein the C terminus of the B chain is covalently linked to the N Terminus of the A chain via the single-chain linking peptide, wherein said glucagon analogue is covalently linked to said single-chain insulin analogue.

In accordance with embodiment 30, a fusion peptide of any one of embodiments 18-29 is provided wherein the insulin peptide comprises an A chain sequence of GIVEQCCTSICSLYQLENYCN (SEQ ID NO: 60); and a B chain sequence selected from the group consisting of

```
                                    (SEQ ID NO: 61)
FVNQHLCGSHLVEALYLVCGERGFFYTPKT

                                   (SEQ ID NO: 119)
FVNQHLCGSHLVEALYLVCGERGFFYTKPT

                                   (SEQ ID NO: 120)
FVNQHLCGSHLVEALYLVCGERGFFYTDKT

                                   (SEQ ID NO: 122)
FVKQHLCGSHLVEALYLVCGERGFFYTPET
and

                                   (SEQ ID NO: 121)
FVKQHLCGSHLVEALYLVCGERGFFYTEKT.
```

In accordance with embodiment 31, a fusion peptide of any one of embodiments 18-30 is provided wherein the C-terminal amino acid of the glucagon analogue is covalently linked to the insulin peptide, optionally via a fusion peptide linker, at the N-terminal alpha-amine of the B chain.

In accordance with embodiment 32, a fusion peptide of any one of embodiments 18-30 is provided wherein the C-terminal amino acid of the glucagon analogue is covalently linked to the insulin peptide, optionally via a fusion peptide linker, at the side chain of an amino acid at position B28 or B29, optionally wherein the amino acid at position B28 or B29 is Lys.

In accordance with embodiment 33, a fusion peptide of any one of embodiments 18-32 is provided wherein said insulin peptide is a single-chain insulin analogue comprising a single-chain linking peptide covalently linking the insulin B chain to the insulin A chain, and the C-terminal amino acid of the glucagon analogue is covalently linked to the insulin peptide, at a side chain of an amino acid of said single-chain linking peptide.

In accordance with embodiment 34, a fusion peptide of any one of embodiments 18-33 is provided wherein the intrachain bridge formed between the amino acids at positions $X_{13}$ and $X_{17}$ is a lactam bridge.

In accordance with embodiment 35, a fusion peptide of any one of embodiments 18-34 is provided wherein $X_{13}$ is Lys; and $X_{17}$ is Glu.

In accordance with embodiment 36, a fusion peptide of any one of embodiments 18-35 is provided wherein said glucagon analogue further comprises a second intrachain bridge formed between the amino acids at positions i and i+4, wherein i is an integer selected from 18 to 28.

In accordance with embodiment 37, a fusion peptide of any one of embodiments 18-35 is provided wherein said glucagon analogue further comprises a second intrachain bridge formed between the amino acids at positions i and i+7, wherein i is an integer selected from 18 to 24. i and i+7 Cys SH groups react with bifuctional bromoacetyled Lys, ornithine or 2,4-diaminobutyric acid linkers that allow placement of side-chain cross-linking (thioether staples) into glucagon.

In accordance with embodiment 38, a fusion peptide of any one of embodiments 18-36 is provided wherein the first and optional second intrachain bridge is a lactam.

In accordance with embodiment 39, a fusion peptide of any one of embodiments 18-36 is provided wherein the interchain bridge is formed between the side chains of an amino acid pair comprising a first amino acid selected from Lys, Ornithine, 2,4-diaminobutyric acid, and 2,3-diaminopropionic acid; and a second amino acid selected from Asp, Glu and α-aminoadipic acid.

In accordance with embodiment 40, a fusion peptide of any one of embodiments 18-39 is provided wherein said glucagon analogue comprises a C-terminal extension of the tripeptide sequence EEK.

In accordance with embodiment 41, a fusion peptide of any one of embodiments 18-40 is provided wherein said glucagon analogue comprises up to 3 residue modifications at non-bridged positions 3, 16, 20, 21, 24, 27 or 28 where the native residue is replaced by Glu, Lys, Arg, Orn, Diamino-Butyric Acid or Diamino-Proprionic Acid.

In accordance with embodiment 42, a fusion peptide of any one of embodiments 18-41 is provided wherein said insulin peptide further comprises an albumin-binding element, optionally wherein said albumin-binding element is an acyl group containing 8-22 carbon atoms attached to a side chain, optionally with a spacer element of less than 25 atoms.

In accordance with embodiment 43, a fusion peptide of any one of embodiments 18-42 is provided wherein the insulin peptide is modified by the deletion of residues B1, B1-B2 or B1-B3.

In accordance with embodiment 44, a fusion peptide of any one of embodiments 18-43 is provided wherein the insulin peptide is modified by substitution of Asn at position A21 by Gly, Ala, Ser or Thr.

In accordance with embodiment 45, a fusion peptide of any one of embodiments 18-44 is provided wherein the insulin peptide is modified by at least one of the following: a substitution of a substitution of Asn at B3 by Lys or Glu; a substitution of Ser at B9 by Asp; a substitution of Val at B12 by Thr; a substitution of Glu at B13 by Gln; a substitution of Tyr at B16 by Ala or Glu; a substitution of Phe at B24 by Leu or Met; a substitution of Phe at B25 by His; a substitution of Tyr at B26 by Glu, Ile, Leu or Val; a substitution of Pro at B28 by Lys or Glu; a substitution of Lys at B29 by Pro, Glu, or Arg; a substitution of Gly at A1 by Ala; a substitution of Val at A3 by Thr; a substitution of Thr at A8 by His, Gln or Glu; a substitution of Tyr at A14 by Ala, Lys or Glu; a substitution of Glu at A17 by Gln; or a substitution of Asn at A21 by Gly.

In accordance with embodiment 46, a pharmaceutical composition is provided, comprising a fusion protein of any one of embodiments 18-45 and a pharmaceutically acceptable carrier.

In accordance with embodiment 47, a method of treating a patient afflicted with hypoglycemia is provided, said method comprising the step of administering a physiologically effective amount of the composition of embodiment 46.

In accordance with embodiment 48, a method of treating a patient with diabetes mellitus is provided, said method comprising the step of administering a physiologically effective amount of the composition of embodiment 46.

EXAMPLES

Chemical Synthesis of Glucagon Analogues. We employed solid-phase peptide synthesis to prepare an extensive collection of glucagon analogues (Table 1). The peptides were synthesized starting with Pre-loaded Fmoc-Lys (Boc)-Wang or Fmoc-Thr(tBu)-Wang resins using traditional Fmoc/tBu chemistry with repetitive DIC/6-Cl-HOBt activation/coupling cycles using DIC/6-Cl-HOBt or DIC/Oxyma Pure (Ethyl cyano(hydroxyimino)acetate) activation (10 equivalents) and IR or induction heating at 60° C. for 10 min per cycle and 50° C. for Fmoc deprotection (20% piperidine/DMF, 2×5 min). Tribute or Chorus automated peptide synthesizers (Gyros Protein Technology, Tucson, AZ) were used. All amino acids, DIC and 6-Cl-HOBt and Oxyma Pure were purchased from Gyros Protein Technology (Tucson, AZ). Peptides were cleaved from resin and deprotected by treatment with trifluoroacetic acid (TFA) containing 2.5% triisopropylsilane (TIS), 2.5% water, 2.5% DODT (ethylenedioxy)-diethenethiol), and 2.5% of Anisole.

Sied-chain/Side-chain Lactam Bond Formation. In order to generate the Lactam side-chain cyclization, we used othoganal protectors such as Lys(Alloc) and Glu(Allyl) at positions of interest [K9-E13, K12-E16, K13-E17, K24-E28] and simulteneously deprotected Alloc and Allyl groups prior to lactam bond formation. Thus, the resin bound fully protected peptide (0.02 to 0.1 mmol) was washed with DCM (dichloromethane) in the presence of bubbling Argon (Ar) or nitrogen gas ($N_2$), which was maintained throughout the reaction. 24 equivalents of PhSi3 (phenylsilane) were added to the resin in 2 ml of DCM along with 0.25 equivalents of $Pd(PPh_3)_4$ (Palladium-triphenylphosphine), as a reaction catalyzer. This deprotection reaction was left for 30 min and then repeated once. Series of resin washes of DCM and DMF (dimethylformamide) where included between steps. The lactam-bond formation was induced by the addition of 12 equivalents of DIEA (N,N-Diisopropylethylamine), 6 equivalents of HBTU or PyBop or PyOxim [Ethyl cyano (hydroxyimino)acetato-O2]tri-1-pyrrolidinylphosphonium hexafluorophosphatel, and 6 of HOBt or Oxyma Pure (Ethyl cyano(hydroxyimino)acetate). This reaction was left going for 2 hours, and the completion was evaluated by the Nynhidrin test. Finally, Fmoc groups were removed by a 20 mM reaction with 20% Piperidine in DMF. The peptide resin was again washed with DCM (3×2 mM), DMF (3×1 min), and DCM (4×2 min) and dried prior to cleavage from the resin.

Side-chain Disulfide Bond Formation. The oxidation of the cysteine-containing glucagon analogues to induce disulfide-bridge formation was done by dimethylsulfoxide (DMSO) oxidation, consisting of 0.1 mM of the linear (reduced) peptides with 10% DMSO in MiliQ-grade water. The reaction was stirred at room temperature for 24 hours. After that, the reactions were analyzed by analytical HPLC and LC/MS and preparative HPLC on a C8 column was used for purification.

Side-chain Thioether Based Stapled i-i+7 Bridge Formation. Cysteine residues were positionally substituted in a distance of i to i+7 residues apart in glucagon in order to stabilize alpha helical conformation into glucagon peptides (Seq IDs 33-38 and 75-85). Cys residues were protected as Cys(tBu) for solid phase synthesis build-out. Linear peptides (either crude or purified) dissolved at 0.1 mM in buffer containing ammonium bicarbonate (0.1 M), uera (1 M), and organic modifier (acetonitrile or tetrahydrofuran, 5-25%) at pH 9.0 were dissolved with various bifuctional bromoacetyl crosslinkers (1.2 equivelents) and reacted at room temperature overnight. After that, the reactions were analyzed by analytical HPLC and LC/MS and preparative HPLC on a C8 column was used for purification. The bifuctional bromoacetyl crosslinkers were prepared from reaction of either lysine, ornithine, or diaminoproprionic acid and activated bromoacetic acid (3-5 equivalents) in dioxane:$NaHCO_3$ (Aq, 1 M) 1:1 at 0.25 M at 5° C. to room temperature overnight followed by extractive work-up, HPLC characterization and lyophilization.

Peptide and Fusion Protein Purification. Peptides were purified by preparative RP-HPLC on a CLIPEUS C8 (20×250 mm, 5 μm, Higgins Analytical) column with 0.1% TFA/$H_2O$ (A) and 0.1% TFA/$CH_3CN$ (B) as elution buffers. Identity of the peptides was confirmed by LC-MS (Finnigan LCQ Advantage, Thermo) on a TARGA C8 (4.6×250 mm, 5 μm, Higgins Analytical) with 0.1% TFA/H2O (A) and 0.1% TFA/CH3CN as eluents. Previous to fibrillation or activity assays, peptides were purified up to 2 times to achieve a purity>95%. The peptide concentration was assessed based on UV absorption at λ=280 nm measured on a NanoDrop 1000 spectrophotometer (Thermo Scientific, Wilmington, DE). Extinction coefficient at λ=280 nm were calculated using the Property Calculator (Innovagen, PepCalc.com).

Synthesis and purification of Sortase A. Bacterial Expression of Sortases A was done on *E. coli* BL21(DE3) transformed with pET29 sortase expression plasmids and were cultured at 37° C. in LB with 50 μg/mL kanamycin until OD600=0.5-0.8. IPTG was added to a final concentration of 0.4 mM and protein expression was induced for three hours at 30° C. The cells were harvested by centrifugation and resuspended in lysis buffer (50 mM Tris pH 8.0, 300 mM NaCl supplemented with 1 mM $MgCl_2$, 2 units/mL DNAseI (NEB), 1 mM PMSF and 5 mM of Imidazol). Cells were lysed by passing them through a microfluidizer. The clarified supernatant was purified on Ni-NTA agarose following the manufacturer's instructions. Washes were done at 20 mM imidazole in lysis buffer and elution was done at 700 mM imidazole. Elutions were dialyzed against Tris-buffered saline (25 mM Tris pH 7.5, 150 mM NaCl).

TABLE 1

Glucagon analogues synthesized by SPPS under in vitro and in vivo evaluation.

| | |
|---|---|
| Glucagon | HSQGTFTSDYSKYLDSRRAQDFVQWLMNT; SEQ ID NO: 1 |
| R30-Glucagon | HSQGTFTSDYSKYLDSRRAQDFVQWLMNTR; SEQ ID NO: 2 |
| K30-Glucagon | HSQGTFTSDYSKYLDSRRAQDFVQWLMNTK; SEQ ID NO: 3 |
| Dab30-Glucagon | HSQGTFTSDYSKYLDSRRAQDFVQWLMNT[Dab]; SEQ ID NO: 4 |
| O30-Glucagon | HSQGTFTSDYSKYLDSRRAQDFVQWLMNTO; SEQ ID NO: 5 |
| D30-Glucagon | HSQGTFTSDYSKYLDSRRAQDFVQWLMNTD; SEQ ID NO: 6 |
| E30-Glucagon | HSQGTFTSDYSKYLDSRRAQDFVQWLMNTE; SEQ ID NO: 7 |

TABLE 1-continued

Glucagon analogues synthesized by SPPS under in vitro and in vivo evaluation.

| | |
|---|---|
| O12, O17, O18, K30 Glucagon | HSQGTFTSDYSOYLDSOOAQDFVQWLMNTK; SEQ ID NO: 8 |
| K12-E16-Lactam-Glucagon | HSQGTFTSDYS**K**YLD**E**RRAQDFVQWLMNT; SEQ ID NO: 9 |
| K13,E17-Lactam-Glucagon | HSQGTFTSDYSK**K**LDS**E**RAQDFVQWLMNT; SEQ ID NO: 10 |
| K17,E21-Lactam-Glucagon | HSQGTFTSDYSKYLDS**K**RAQ**E**FVQWLMNT; SEQ ID NO: 11 |
| K24,E28-Lactam-Glucagon | HSQGTFTSDYSKYLDSRRAQDFV**K**WLM**E**T; SEQ ID NO: 12 |
| Orn12, K30 17-21-Lactam Glucagon | HSQGTFTSDYSOYLDS**K**RAQ**E**FVQWLMNTK; SEQ ID NO: 13 |
| D-Cys13-Cys16-Glucagon | HSQGTFTSDYSK[**D-Cys**]LDCRRAQDFVQWLMNT; SEQ ID NO: 14 |
| D-Cys16, Cys19-Glucagon | HSQGTFTSDYSKYLD[**D-Cys**]RRCQDFVQWLMNT; SEQ ID NO: 15 |
| D-Cys17-Cys20-Glucagon | HSQGTFTSDYSKYLDS[**D-Cys**]RACDFVQWLMNT; SEQ ID NO: 16 |
| D-Cys18-Cys21-Glucagon | HSQGTFTSDYSKYLDSR[**D-Cys**]AQCFVQWLMNT; SEQ ID NO: 17 |
| D-Cys20-Cys23-Glucagon | HSQGTFTSDYSKYLDSRRA[**D-Cys**]DFCQWLMNT; SEQ ID NO: 18 |
| D-Cys21-Cys24-Glucagon | HSQGTFTSDYSKYLDSRRAQ[**D-Cys**]FVCWLMNT; SEQ ID NO: 19 |
| D-Cys24-Cys27-Glucagon | HSQGTFTSDYSKYLDSRRAQDFV[**D-Cys**]WLCNT; SEQ ID NO: 20 |
| Glucagon-EEK | HSQGTFTSDYSOYLDSOOAQDFVQWLMNTEEK; SEQ ID NO: 21 |
| Aib16-Glucagon-EEK | HSQGTFTSDYSOYLD[Aib]OOAQDFVQWLMNTEEK; SEQ ID NO: 22 |
| O12, O18, K13, E17-Lactam-Glucagon-EEK | HSQGTFTSDYSO**K**LDS**E**OAQDFVQWLMNTEEK; SEQ ID NO: 23 |
| K9, E13-Lactam-Glucagon-EEK | HSQGTFTS**K**YSO**E**LDSOOAQDFVQWLMNTEEK; SEQ ID NO: 24 |
| K12-E16-Lactam-Glucagon-EEK | HSQGTFTSDYS**K**YLD**E**OOAQDFVQWLMNTEEK; SEQ ID NO: 25 |
| K17, E21-Lactam-Glucagon-EEK | HSQGTFTSDYSOYLDS**K**OAQ**E**FVQWLMNTEEK; SEQ ID NO: 26 |
| K24, E28-Lactam-Glucagon-EEK | HSQGTFTSDYSOYLDSOOAQDFV**K**WLM**E**TEEK; SEQ ID NO: 27 |
| K20, E24-Lactam-Glucagon-EEK | HSQGTFTSDYSOYLDSOOAKDFVEWLMNTEEK; SEQ ID NO: 62 |
| E24, K28-Lactam-Glucagon-EEK | HSQGTFTSDYSOYLDSOOAQDFVEWLMKTEEK; SEQ ID NO: 63 |
| D-Cys2-Cys5-Glucagon-EEK | H[**D-Cys**]QGCFTSDYSOYLDSOOAQDFVQWLMNTEEK; SEQ ID NO: 28 |
| D-Cys16, Cys19-Glucagon-EEK | HSQGTFTSDYSOYLD[**D-Cys**]OOCQDFVQWLMNTEEK; SEQ ID NO: 29 |
| D-Cys20-Cys23-Glucagon-EEK | HSQGTFTSDYSOYLDSOOA[**D-Cys**]DFCQWLMNTEEK; SEQ ID NO: 30 |
| D-Cys21-Cys24-Glucagon-EEK | HSQGTFTSDYSOYLDSOOAQ[**D-Cys**]FVCWLMNTEEK; SEQ ID NO: 31 |
| D-Cys24-Cys27- Glucagon-EEK | HSQGTFTSDYSOYLDSOOAQDFV[**D-Cys**]WLCNTEEK; SEQ ID NO: 32 |
| Cys17, Cys21-Glucagon | HSQGTFTSDYSKYLDSCRAQCFVQWLMNT; SEQ ID NO: 33 |
| Cys13, 20-Glucagon (Linear) | HSQGTFTSDYSKCLDSRRACDFVQWLMNT; SEQ ID NO: 34 |
| Cys14, 21-Glucagon (Linear) | HSQGTFTSDYSKYCDSRRAQCFVQWLMNT; SEQ ID NO: 35 |
| Cys17, 24-Glucagon (Linear) | HSQGTFTSDYSKYLDSCRAQDFVCWLMNT; SEQ ID NO: 36 |
| Cys20, 27-Glucagon (Linear) | HSQGTFTSDYSKYLDSRRACDFVQWLCNT; SEQ ID NO: 37 |

TABLE 1-continued

| Glucagon analogues synthesized by SPPS under in vitro and in vivo evaluation. | |
|---|---|
| Cys21, 28-Glucagon (Linear) | HSQGTFTSDYSKYLDSRRAQCFVQWLMCT; SEQ ID NO: 38 |
| K13, E17-Lactam-D-Cys20-Cys23-Glucagon-EEK | HSQGTFTSDYSOKLDSEOA[D-Cys]DFCQWLMNTEEK; SEQ ID NO: 64 |
| K13, E17-Lactam-D-Cys21-Cys24-Glucagon-EEK | HSQGTFTSDYSOKLDSEOAQ[D-Cys]FVCWLMNTEEK; SEQ ID NO: 65 |
| K13, E17-Lactam-D-Cys24-Cys27-Glucagon-EEK | HSQGTFTSDYSOKLDSEOAQDFV[D-Cys]WLCNTEEK; SEQ ID NO: 66 |
| K13, E17-Lactam-P27, G30, G31, G32-Glucagon | HSQGTFTSDYSKKLDSERAQDFVQWLPNTGGG; SEQ ID NO: 67 |
| K13, E17-Lactam-D-C18, C21-P27, G30, G31, G32-Glucagon | HSQGTFTSDYSKKLDSE[D-Cys]AQCFVQWLPNTGGG; SEQ ID NO: 68 |
| K13, E17-Lactam-D-C20, C23-P27, G30, G31, G32-Glucagon | HSQGTFTSDYSKKLDSERA[D-Cys]DFCQWLPNTGGG; SEQ ID NO: 69 |
| K13, E17-Lactam-D-C21, C24-P27, G30, G31, G32-Glucagon | HSQGTFTSDYSKKLDSERAQ[D-Cys]FVCWLPNTGGG; SEQ ID NO: 70 |

Fibrillation Assays. We employed an automated plate-based fluorescent device to monitor the time course of peptide fibrillation using a Thioflavin T (ThT) assay. This assay is based on the THT fluorescence emission at 480 nm upon binding to mature fibrils when excited at 440 nm. The assay was performed by preparing stock solutions of the fusion protein and the individual peptides in either NaCl 0.9% (pH 2.5) or PBS (pH 7.4). Our experience has identified 100-μM final concentration as optimal fibrillation conditions for glucagon analogues. Stock solutions were diluted with NaCl 0.9% or 1×PBS buffer, pH adjusted (with 1N HCl or 1N NaOH) mixed with Thioflavin-T (THT) at a final concentration of 16 μM, centrifuged, and 250 μl of the sample were placed on a 96-well plate with 4-10 technical replicates. Measurements were done every 15 minutes and the sample agitated at 1096 cpm at 37° C. on a Synergy H1 microplate reader (BioTek, Winooski, VT). The lag time, defined as the time-point at which fibrillation starts its exponential phase, was considered as the point at which fluorescence was 3 times the background signal.

Cell-based Activity Assays. We generated a cAMP assay on HepG2 cells transiently transfected with the glucagon receptor (GCGR). The GCGR gene with C-terminal Flag tag was synthesized and ligated to a pcDNA 3.1 vector by Genscript. A plate of HepG2 cells was grown to 70% confluence and then transfected with 15 μg plasmid. After 48 hours, the cells were transferred to a 384 plate (500 cells/well) and incubated with the analogues for 30 min. Then, cAMP was measured following the instructions of the LANCE™ Ultra cAMP Kit (PerkingElmer) using 3 technical replicates per point. This is a TR-FRET assay based on the competition between a europium-labeled cAMP and sample cAMP for binding to cAMP-specific labeled antibodies. In the LANCE cAMP assay, a higher sample cAMP (higher glucagon activity) translates to lower signal. The expression of GCGR by HepG2 cells was confirmed by Western Blot using a monoclonal Anti-Flag antibody and a polyclonal Anti-GCGR antibody. GCGR (62 kDa) formed oligomers upon cell lysis and sample preparation, exhibiting a>250 kDa molecular weight.

Glucagon Activity Assays. The glycemic activities of glucagon analogues were tested (Ismail-Beigi, Case Western Reserve University) in normal male rats (250-350 g) that were fasted for 4 h before the injection and not fed during the course of the experiment (4-5 rats per dose of glucagon in parallel). Glucagon or analogues were prepared (150 μg/ml in sterile 50 mM Tris-HCl buffer (pH 8.0)) and administered by subcutaneous injections (40.1 nmol/kg (~50 ug/333 g rat)) in an injection volume of 200 μl/333 g rat. Rats were grouped according to their 2$^{nd}$ measured starting blood-glucose concentrations to ensure similar starting values at time=0. For in vivo dose-response studies a series of doses (40.1, 8.0, 1.6, 0.32, 0.064, and 0.013 nmol/kg) was tested in groups of 4-5 rats at each dose. Diluent volume was 200 μl/333 g rat. Experiments were repeated at least twice, and the results were averaged. The rise in blood glucose values were corrected by any changes observed in diluent-injected rats.

To test for stability of glucagon and its analogues, samples (150 μg/ml in 50 mM Tris-HCl buffer (pH 8.0)) were incubated at 37° C. with mild agitation and rotation. Samples were tested as described above after varying periods of incubation.

Chemical Synthesis of SCIs. We prepared 49-residue (inactive DesDi) and 57-residue single-chain insulin (SCI) analogues lacking internal tryptic sites for use in trypsin-mediated semi-synthesis reactions (below). The 49-residue SCI-DesDi was synthesized to be an inactive control to test the trypsin ligation strategy and glucagon activity in a fusion protein. SCIs were chemically synthesized using Fmoc/OtBu solid-phase chemistry on a pre-loaded H-Asn(Trt)-HMBP-Chemmatrix resin, with repetitive coupling cycles using DIC/6-Cl-HOBt activation (10 Equivalents) and IR or induction heating at 60° C. for 10 min per cycle and 50° C. for Fmoc deprotection (20% piperidine/DMF, 2×5 min). Tribute or Chorus automated peptide synthesizers (Gyros Protein Technology, Tucson, AZ) were used. Pre-loaded Fmoc-Asn(Trt)-Chemmatrix resin was used. All amino acids, DIC and 6-Cl-HOBt were purchased from Gyros Protein Technology (Tucson, AZ). Peptides were cleaved and deprotected by treatment with trifluoroacetic acid (TFA) containing 2.5% triisopropylsilane (TIS), 2.5% water, 2.5% DODT (ethylenedioxy)-diethenethiol), and 2.5% of anisole. The cleaved crude SCI was in reduced form, so it was subsequently folded by oxidation at 0.1 mM in Gly (20 mM), Cys (2.0 mM) pH adjusted to 10.6 (10 N NaOH) and stirred at 5° C. for 12-24 hrs. The course of the folding reaction was monitored by RP-HPLC with an aliquot (75 μl) quenched with 5N HCl (5 μl). The crude folded SCI reaction was quench with HCl (5 N) and filtered (0.2 microns) prior to Preparative HPLC. Folded SCI was purified by preparative RP-HPLC on a PROTO 300 C4 (20×250 mm, 10 μm, Higgins Analytical) column with 0.1% TFA/$H_2O$ (A) and 0.1% TFA/$CH_3CN$ (B) as elution buffers. Identity of the SCI was confirmed by LC-MS (Finnigan LCQ Advantage, Thermo) on a TARGA C8 (4.6×250 mm, 5 μm, Higgins Analytical) with 0.1% TFA/$H_2O$ (A) and 0.1% TFA/$CH_3CN$ as eluents.

Preparation of Glucagon-Insulin Fusion Proteins. A peptide bond was introduced between the C-terminal Lysine of a 13-17 lactam-stapled glucagon analogue and the α-amino-group of $Phe^{B1}$ of an SCI as catalyzed in an organic co-solvent by trypsin. Neither the glucagon analogue nor the SCI had internal tryptic cleavage sites. Additionally, a glucagon analogue without the 13-17 lactam modifications was fused to an inactive 49-residue SCI-DesDi as a control molecule. The polypeptides and the fusion protein sequences are given in Table 2. An approximately 1:1 molecular ratio was used for trypsin-mediated ligation, typically 9 mg of SCI were dissolved along with 3 mg of glucagon-EEK in 200 μl of a mixed solvent system containing 1,4-butanediol and dimethylacetamide. The pH was adjusted to neutral with 2 μl of 4-methylmorpholine, and the reaction was carried out for 24-48 hours. Fusion protein was purified by preparative RP-HPLC on a C8 column with 0.1% TFA/$H_2O$ (A) and 0.1% TFA/CH3CN (B) as elution buffers. Identity was confirmed by LC-MS.

TABLE 2

List of glucagon and SCI analogues used to make fusion protein, along with the sequences of the fusion protein made by trypsin-mediated ligation.

| Name | Nickname | Sequence |
|---|---|---|
| K13, E17-Lactam-Glucagon-EEK | Active Glucagon | HSQGTFTSDYS**OK**LDS**EO**AQDFVQWLMNT**EEK**<br>(SEQ ID NO: 23) |
| K9, E13-Lactam-Glucagon-EEK | Inactive Glucagon | HSQGTFTS**K**YS**OE**LDS**OO**AQDFVQWLMNT**EEK**<br>(SEQ ID NO: 24) |
| OrnB22, GluB29, GlnA8, GluA14-EEGPOO SCI | Active SCI | FVNQHLCGSHLVEALYLVCGE**O**GFFYTP**E**T**EEGPOO**<br>GIVEQCC**Q**SICSL**E**QLENYCN<br>(SEQ ID NO: 71) |
| OrnB22, GluB29, LeuA3-GlnA8, GluA14-EEGPOO-SCI | Inactive SCI | FVNQHLCGSHLVEALYLVCGE**O**GFFYTP**E**T**EEGPOO**<br>GI**L**EQCC**Q**SICSL**E**QLENYCN<br>(SEQ ID NO: 72) |
| K13, E17-Lactam-Glucagon-EEK fused to OrnB22, GluB29, GlnA8, GluA14-EEGPOO-SCI | Active SCI/Active Glucagon | HSQGTFTSDYS**OK**LDS**EO**AQDFVQWLMNT**EEK**<br>FVNQHLCGSHLVEALYLVCGE**O**GFFYTP**E**T**EEGPOO**GI<br>VEQCC**Q**SICSL**E**QLENYCN<br>(SEQ ID NO: 73) |
| K13, E17-Lactam-Glucagon-EEK fused to OrnB22, GluB29, LeuA3-GlnA8, GluA14-EEGPOO-SCI | Inactive SCI/Active Glucagon | HSQGTFTSDYS**OK**LDS**EO**AQDFVQWLMNT**EEK**<br>FVNQHLCGSHLVEALYLVCGE**O**GFFYTP**E**T**EEGPOO**GI<br>LEQCC**Q**SICSL**E**QLENYCN<br>(SEQ ID NO: 74) |
| K9, E13-Lactam-Glucagon-EEK fused to OrnB22, GluB29, GlnA8, GluA14-EEGPOO-SCI | Active SCI/Inactive Glucagon | HSQGTFTS**K**YS**OE**LDS**OO**AQDFVQWLMNT**EEK**<br>FVNQHLCGSHLVEALYLVCGE**O**GFFYTP**E**T**EEGPOO**GI<br>VEQCC**Q**SICSL**E**QLENYCN<br>(SEQ ID NO: 75) |
| K9, E13-Lactam-Glucagon-EEK fused to OrnB22, GluB29, LeuA3-GlnA8, GluA14-EEGPOO-SCI | Inactive SCI/Inactive Glucagon | HSQGTFTS**K**YS**OE**LDS**OO**AQDFVQWLMNT**EEK**<br>FVNQHLCGSHLVEALYLVCGE**O**GFFYTP**E**T**EEGPOO**GI<br>**L**EQCC**Q**SICSL**E**QLENYCN<br>(SEQ ID NO: 76) |

(human glucagon)

SEQ ID NO: 1

HSQGTFTSDYSKYLDSRRAQDFVQWLMNT (human proinsulin)

SEQ ID NO: 77

Phe-Val-Asn-Gln-His-Leu-Cys-Gly-Ser-His-Leu-

Val-Glu-Ala-Leu-Tyr-Leu-Val-Cys-Gly-Glu-Arg-

-continued

```
Gly-Phe-Phe-Tyr-Thr-Pro-Lys-Thr-Arg-Arg-Glu-

Ala-Glu-Asp-Leu-Gln-Val-Gly-Gln-Val-Glu-Leu-

Gly-Gly-Gly-Pro-Gly-Ala-Gly-Ser-Leu-Gln-Pro-

Leu-Ala-Leu-Glu-Gly-Ser-Leu-Gln-Lys-Arg-Gly-

Ile-Val-Glu-Gln-Cys-Cys-Thr-Ser-Ile-Cys-Ser-

Leu-Tyr-Gln-Leu-Glu-Asn-Tyr-Cys-Asn
```

```
(human A chain)
                                    SEQ ID NO: 60
Gly-Ile-Val-Glu-Gln-Cys-Cys-Thr-Ser-Ile-Cys-

Ser-Leu-Tyr-Gln-Leu-Glu-Asn-Tyr-Cys-Asn
```

```
(human B chain)
                                    SEQ ID NO: 61
Phe-Val-Asn-Gln-His-Leu-Cys-Gly-Ser-His-Leu-

Val-Glu-Ala-Leu-Tyr-Leu-Val-Cys-Gly-Glu-Arg-

Gly-Phe-Phe-Tyr-Thr-Pro-Lys-Thr
```

```
(13-17 stabled glucagon)
                                    SEQ ID NO: 10
HSQGTFTSDYSKKLDSERAQDFVQWLMNT
```

Where a lactam bridge connects the side chains of variant residues K13 and E17.

```
(13-17 stabled glucagon)
                                    SEQ ID NO: 78
HSQGTFTSDYSKKLDSERAQDFVQWLMNT-Xaa1
```

Where a lactam bridge connects the side chains of variant residues K13 and E17 and where $Xaa_1$ represents a basic amino acid selected from the group Arg, Lys, Orn, Diamino-Butyric Acid or Diamino-Proprionic Acid.

```
(13-17 stabled glucagon)
                                    SEQ ID NO: 79
HSQGTFTSDYSKKLDSERAQDFVQWLMNT-Xaa1-Xaa2-Xaa3
```

Where a lactam bridge connects the side chains of variant residues K13 and E17; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

```
(13-17 stabled glucagon)
                                    SEQ ID NO: 80
HSQGTFTSDYSOKLDSEOAQDFVQWLMNT-Xaa1-Xaa2-Xaa3
(SEQ ID NO: 48)
```

Where a lactam bridge connects the side chains of variant residues K13 and E17; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

```
(13-17 stabled glucagon with C-terminal disulfide
bridge)
                                    SEQ ID NO: 81
HSQGTFTSDYSKKLDSE[D-Cys]AQCFVQWLMNT
```

Where a lactam bridge connects the side chains of variant residues K13 and E17; where a disulfide bridge connects the side chains of D-Cys at positions 18 and L-Cys at position 21.

```
(13-17 stabled glucagon with C-terminal disulfide
bridge)
                                    SEQ ID NO: 82
HSQGTFTSDYSKKLDSE[D-Cys]AQCFVQWLMNT-Xaa1-Xaa2-Xaa3
```

Where a lactam bridge connects the side chains of variant residues K13 and E17; where a disulfide bridge connects the side chains of D-Cys at positions 18 and L-Cys at position 21; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

```
(13-17 stabled glucagon with C-terminal disulfide
bridge)
                                    SEQ ID NO: 83
HSQGTFTSDYSOKLDSE[D-Cys]AQCFVQWLMNT-Xaa1-Xaa2-Xaa3
```

Where a lactam bridge connects the side chains of variant residues K13 and E17; where O represents Ornithine; where a disulfide bridge connects the side chains of D-Cys at positions 18 and L-Cys at position 21; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

```
(13-17 stabled glucagon with C-terminal disulfide
bridge)
                                    SEQ ID NO: 84
HSQGTFTSDYSKKLDSERA[D-Cys]DFCQWLMNT
```

Where a lactam bridge connects the side chains of variant residues K13 and E17; where a disulfide bridge connects the side chains of D-Cys at positions 20 and L-Cys at position 23.

```
(13-17 stabled glucagon with C-terminal disulfide
bridge)
                                    SEQ ID NO: 85
HSQGTFTSDYSKKLDSERA[D-Cys]DFCQWLMNT-Xaa1-Xaa2-Xaa3
```

Where a lactam bridge connects the side chains of variant residues K13 and E17; where a disulfide bridge connects the side chains of D-Cys at positions 20 and L-Cys at position 23; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal disulfide bridge)

SEQ ID NO: 86

HSQGTFTSDYSOKLDSEOA[D-Cys]DFCQWLMNT-$Xaa_1$-$Xaa_2$-$Xaa_3$

Where a lactam bridge connects the side chains of variant residues K13 and E17; where O represents Ornithine; where a disulfide bridge connects the side chains of D-Cys at positions 20 and L-Cys at position 23; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

(13-17 stabled glucagon with C-terminal disulfide bridge)

SEQ ID NO: 87

HSQGTFTSDYSKKLDSERAQDFV[D-Cys]WLCNT

Where a lactam bridge connects the side chains of variant residues K13 and E17; where a disulfide bridge connects the side chains of D-Cys at positions 24 and L-Cys at position 27.

(13-17 stabled glucagon with C-terminal disulfide bridge)

SEQ ID NO: 88

HSQGTFTSDYSKKLDSERAQDFV[D-Cys]WLCNT-$Xaa_1$-$Xaa_2$-$Xaa_3$

Where a lactam bridge connects the side chains of variant residues K13 and E17; where a disulfide bridge connects the side chains of D-Cys at positions 24 and L-Cys at position 27; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal disulfide bridge)

SEQ ID NO: 89

HSQGTFTSDYSOKLDSEOAQDFV[D-Cys]WLCNT-$Xaa_1$-$Xaa_2$-$Xaa_3$

Where a lactam bridge connects the side chains of variant residues K13 and E17; where O represents Ornithine; where a disulfide bridge connects the side chains of D-Cys at positions 24 and L-Cys at position 27; where $Xaa_1$ represents an amino acid selected from the group Ala, Gly, Glu, Orn, Diamino-Butyric Acid or Diamino-Proprionic Acid; where $Xaa_2$ is Gly, Ala, Ser, 25 Gln or Glu; and where Xaa 3 represents Lys or Arg.

(13-17 stabled glucagon with C-terminal disulfide bridge)

SEQ ID NO: 90

HSQGTFTSDYSKKLDSERAQDFVQWL[D-Cys]NTC

Where a lactam bridge connects the side chains of variant residues K13 and E17; where a disulfide bridge connects the side chains of D-Cys at positions 27 and L-Cys at position 30.

(13-17 stabled glucagon with C-terminal disulfide bridge)

SEQ ID NO: 91

HSQGTFTSDYSKKLDSERAQDFVQWL[D-Cys]NTC-$Xaa_1$-$Xaa_2$-$Xaa_3$

Where a lactam bridge connects the side chains of variant residues K13 and E17; where a disulfide bridge connects the side chains of D-Cys at positions 27 and L-Cys at position 30; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal disulfide bridge)

SEQ ID NO: 92

HSQGTFTSDYSOKLDSEOAQDFVQWL[D-Cys]NTC-$Xaa_1$-$Xaa_2$-$Xaa_3$

Where a lactam bridge connects the side chains of variant residues K13 and E17; where O represents Ornithine; where a disulfide bridge connects the side chains of D-Cys at positions 27 and L-Cys at position 30; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

(13-17 stabled glucagon with C-terminal disulfide bridge)

SEQ ID NO: 93

HSQGTFTSDYSKKLDSERAQDFVQWLM[D-Cys]T-$Xaa_1$-C

Where a lactam bridge connects the side chains of variant residues K13 and E17; where a disulfide bridge connects the side chains of D-Cys at positions 28 and L-Cys at position 31; where $Xaa_1$ represents an amino acid selected from the group Ala, Gly, Glu, Arg, Lys, Orn, Diamino-Butyric Acid or Diamino-Proprionic Acid (13-17 stabled glucagon with C-terminal disulfide bridge)

SEQ ID NO: 94

HSQGTFTSDYSKKLDSERAQDFVQWLM[D-Cys]T-$Xaa_1$-C-$Xaa_2$-$Xaa_3$

Where a lactam bridge connects the side chains of variant residues K13 and E17; where a disulfide bridge connects the side chains of D-Cys at positions 28 and L-Cys at position 31; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal disulfide bridge)

SEQ ID NO: 95

HSQGTFTSDYSOKLDSEOAQDFVQWLM[D-Cys]T-$Xaa_1$-C-$Xaa_2$-$Xaa_3$

Where a lactam bridge connects the side chains of variant residues K13 and E17; where O represents Ornithine; where a disulfide bridge connects the side chains of D-Cys at positions 28 and L-Cys at position 31; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

```
(13-17 and 20-24 dual-stabled glucagon)
                                  SEQ ID NO: 96
HSQGTFTSDYSKKLDSERAKDFVEWLMNT
```

Where a lactam bridge connects the side chains of variant residues K13 and E17 and where a second lactam bridge connects the side chains of K20 and E24.

```
(13-17 and 20-24 dual-stabled glucagon)
                                  SEQ ID NO: 97
HSQGTFTSDYSKKLDSERAKDFVEWLMNT-Xaa1
```

Where a lactam bridge connects the side chains of variant residues K13 and E17; where a second lactam bridge connects the side chains of K20 and E24; and where $Xaa_1$ represents a basic amino acid selected from the group Arg, Lys, Orn, Diamino-Butyric Acid or Diamino-Proprionic Acid.

```
(13-17 and 20-24 dual-stabled glucagon)
                                  SEQ ID NO: 98
HSQGTFTSDYSKKLDSERAKDFVEWLMNT-Xaa1-Xaa2-Xaa3
```

Where a lactam bridge connects the side chains of variant residues K13 and E17; where a second lactam bridge connects the side chains of K24 and E28; and $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

```
(13-17 and 20-24 dual-stabled glucagon)
                                  SEQ ID NO: 99
HSQGTFTSDYSOKLDSEOAKDFVEWLMNT-Xaa1-Xaa2-Xaa3
```

Where a lactam bridge connects the side chains of variant residues K13 and E17; where a second lactam bridge connects the side chains of K24 and E28; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

```
(13-17 and 24-28 dual-stabled glucagon)
                                  SEQ ID NO: 100
HSQGTFTSDYSKKLDSERAQDFVKWLMET
```

Where a lactam bridge connects the side chains of variant residues K13 and E17 and where a second lactam bridge connects the side chains of K24 and E28.

```
(13-17 and 24-28 dual-stabled glucagon)
                                  SEQ ID NO: 101
HSQGTFTSDYSKKLDSERAQDFVKWLMET-Xaa1
```

Where a lactam bridge connects the side chains of variant residues K13 and E17; where a second lactam bridge connects the side chains of K24 and E28; and where $Xaa_1$ represents a basic amino acid selected from the group Arg, Lys, Orn, Diamino-Butyric Acid or Diamino-Proprionic Acid.

```
(13-17 and 24-28 dual-stabled glucagon)
                                  SEQ ID NO: 102
HSQGTFTSDYSKKLDSERAQDFVKWLMET-Xaa1-Xaa2-Xaa3
```

Where a lactam bridge connects the side chains of variant residues K13 and E17; where a second lactam bridge connects the side chains of K24 and E28; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

```
(13-17 and 24-28 dual-stabled glucagon)
                                  SEQ ID NO: 103
HSQGTFTSDYSOKLDSEOAQDFVKWLMET-Xaa1-Xaa2-Xaa3
```

Where a lactam bridge connects the side chains of variant residues K13 and E17; where a second lactam bridge connects the side chains of K24 and E28; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

```
(13-17 and 27-31 dual-stabled glucagon)
                                  SEQ ID NO: 104
HSQGTFTSDYSKKLDSERAQDFVQWLKNT-Xaa1-E
```

Where a lactam bridge connects the side chains of variant residues K13 and E17 and where a second lactam bridge connects the side chains of K27 and E31; where $Xaa_1$ represents an amino acid selected from the group Ala, Gly, Glu, Arg, Lys, Orn, Diamino-Butyric Acid or Diamino-Proprionic Acid.

```
(13-17 and 27-31 dual-stabled glucagon)
                                  SEQ ID NO: 105
HSQGTFTSDYSKKLDSERAQDFVQWLKNT-Xaa1-E-Xaa2-Xaa3
```

Where a lactam bridge connects the side chains of variant residues K13 and E17; where a second lactam bridge connects the side chains of K24 and E28; where $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

```
(13-17 and 24-28 dual-stabled glucagon)
                                  SEQ ID NO: 106
HSQGTFTSDYSOKLDSEOAQDFVQWLKNT-Xaa1-E-Xaa2-Xaa3
```

Where a lactam bridge connects the side chains of variant residues K13 and E17; where a second lactam bridge connects the side chains of K24 and E28; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

(13-17 stabled glucagon with C-terminal stapled bridge)

SEQ ID NO: 107

HSQGTFTSDYSKKLDSERACDFVQWLCNT

Where a lactam bridge connects the side chains of variant residues K13 and E17 and where a bifunctional bromacetyl linker connects the side chains of C20 and C27.

(13-17 stabled glucagon with C-terminal stapled bridge)

SEQ ID NO: 108

HSQGTFTSDYSKKLDSERACDFVQWLCNT-$Xaa_1$

Where a lactam bridge connects the side chains of variant residues K13 and E17 and where a bifunctional bromacetyl linker connects the side chains of C20 and C27; and where $Xaa_1$ represents a basic amino acid selected from the group Arg, Lys, Orn, Diamino-Butyric Acid or Diamino-Proprionic Acid.

(13-17 stabled glucagon with C-terminal stapled bridge)

SEQ ID NO: 109

HSQGTFTSDYSKKLDSERACDFVQWLCNT-$Xaa_1$-$Xaa_2$-$Xaa_3$

Where a lactam bridge connects the side chains of variant residues K13 and E17 and where a bifunctional bromacetyl linker connects the side chains of C20 and C27; and $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal stapled bridge)

SEQ ID NO: 110

HSQGTFTSDYSOKLDSEOACDFVQWLCNT-$Xaa_1$-$Xaa_2$-$Xaa_3$

Where a lactam bridge connects the side chains of variant residues K13 and E17 and where a bifunctional bromacetyl linker connects the side chains of C20 and C27; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

(13-17 stabled glucagon with C-terminal stapled bridge)

SEQ ID NO: 111

HSQGTFTSDYSKKLDSERAQCFVQWLMCT

Where a lactam bridge connects the side chains of variant residues K13 and E17 and where a bifunctional bromacetyl linker connects the side chains of C21 and C28.

(13-17 stabled glucagon with C-terminal stapled bridge)

SEQ ID NO: 112

HSQGTFTSDYSKKLDSERAQCFVQWLMCT-$Xaa_1$

Where a lactam bridge connects the side chains of variant residues K13 and E17 and where a bifunctional bromacetyl linker connects the side chains of C21 and C28; and where $Xaa_1$ represents a basic amino acid selected from the group Arg, Lys, Orn, Diamino-Butyric Acid or Diamino-Proprionic Acid.

(13-17 stabled glucagon with C-terminal stapled bridge)

SEQ ID NO: 113

HSQGTFTSDYSKKLDSERAQCFVQWLMCT-$Xaa_1$-$Xaa_2$-$Xaa_3$

Where a lactam bridge connects the side chains of variant residues K13 and E17 and where a bifunctional bromacetyl linker connects the side chains of C21 and C28; and $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal stapled bridge)

SEQ ID NO: 114

HSQGTFTSDYSOKLDSEOAQCFVQWLMCT-$Xaa_1$-$Xaa_2$-$Xaa_3$

Where a lactam bridge connects the side chains of variant residues K13 and E17 and where a bifunctional bromacetyl linker connects the side chains of C21 and C28; where O represents Ornithine; where $Xaa_1$ represents an amino acid selected from the group Ala, Gly, Glu, Orn, Diamino-Butyric Acid or Diamino-Proprionic Acid; where $Xaa_2$ is Gly, Ala, Ser, Gln or Glu; and where $Xaa_3$ represents Lys or Arg.

(13-17 stabled glucagon with C-terminal stapled bridge)

SEQ ID NO: 115

HSQGTFTSDYSKKLDSERAQDFVCWLMNT-$Xaa_1$-C

Where a lactam bridge connects the side chains of variant residues K13 and E17 and where a bifunctional bromacetyl linker connects the side chains of C24 and C31; and $Xaa_1$ represents an amino acid selected from the group Ala, Gly, Glu, Arg, Lys, Orn, Diamino-Butyric Acid or Diamino-Proprionic Acid.

(13-17 stabled glucagon with C-terminal stapled bridge)

SEQ ID NO: 116

HSQGTFTSDYSKKLDSERAQDFVCWLMNT-$Xaa_1$-C-$Xaa_2$-$Xaa_3$

Where a lactam bridge connects the side chains of variant residues K13 and E17 and where a bifunctional bromacetyl linker connects the side chains of C24 and C31; and $Xaa_1$ represents an amino acid selected from the group Ala, Gly, Glu, Arg, Lys, Orn, Diamino-Butyric Acid or Diamino-Proprionic Acid; where $Xaa_2$ is Gly, Ala, Ser, Gln or Glu; and where $Xaa_3$ represents a basic amino acid selected from the group Arg, Lys, Orn, Diamino-Butyric Acid or Diamino-Proprionic Acid.

(13-17 stabled glucagon with C-terminal stapled bridge)

SEQ ID NO: 117

HSQGTFTSDYSOKLDSEOAQDFVCWLMNT-$Xaa_1$-C-$Xaa_2$-$Xaa_3$

Where a lactam bridge connects the side chains of variant residues K13 and E17 and where a bifunctional bromacetyl linker connects the side chains of C24 and C31; where O represents Ornithine; where Xaa1 represents an amino acid selected from the group Ala, Gly, Glu, Arg, Lys, Orn, Diamino-Butyric Acid or Diamino-Proprionic Acid; where Xaa2 is Gly, Ala, Ser, Gln or Glu; and where Xaa3 represents a basic amino acid selected from the group Arg, Lys, Orn, Diamino-Butyric Acid or Diamino-Proprionic Acid.

(13-17 stabled glucagon with C-terminal Sortase A recognition motif)

SEQ ID NO: 67

HSQGTFTSDYSKKLDSERAQDFVQWLPNTGGG

Where a lactam bridge connects the side chains of variant residues K13 and E17.

(13-17 stabled glucagon with C-terminal disulfide bridge and Sortase A recognition motif)

SEQ ID NO: 68

HSQGTFTSDYSKKLDSE[D-Cys]AQCFVQWLPNTGGG

Where a lactam bridge connects the side chains of variant residues K13 and E17. and where a disulfide bridge connects the side chains of D-Cys at positions 18 and L-Cys at position 21.

(13-17 stabled glucagon with C-terminal disulfide bridge and Sortase A recognition motif)

SEQ ID NO: 69

HSQGTFTSDYSKKLDSERA[D-Cys]DFCQWLPNTGGG

Where a lactam bridge connects the side chains of variant residues K13 and E17; and where a disulfide bridge connects the side chains of D-Cys at positions 20 and L-Cys at position 23.

(13-17 stabled glucagon with C-terminal disulfide bridge and Sortase A recognition motif)

SEQ ID NO: 70

HSQGTFTSDYSKKLDSERAQ[D-Cys]FVCWLPNTGGG

Where a lactam bridge connects the side chains of variant residues K13 and E17. and where a disulfide bridge connects the side chains of D-Cys at positions 21 and L-Cys at position 24.

The invention claimed is:

1. A fusion peptide comprising a stabilized glucagon analogue having a lower potency at the glucagon receptor than native glucagon and an insulin peptide, wherein the fusion peptide comprises the sequence HSQGTFTSDYSOKLDSEOAQDFVQWLMN-TEEKFVNQHLCGSHLVEALYLVCGEOGFFYTPE-TEEGPOOGIVEQCCQSI CSLEQLENYCN (SEQ ID NO: 73), wherein the side chains of K13 and E17 form a lactam bridge.

2. A fusion peptide comprising a stabilized glucagon analogue having lower potency than native glucagon, wherein said glucagon analogue comprises the amino acid sequence of HSQGTFTSDYSOKLDSEOAQDFVQWLMNTEEK (SEQ ID NO: 23), wherein the side chains of K13 and E17 form a lactam intrachain bridge; and a single-chain insulin analogue comprising an A chain, a B chain and a single-chain linking peptide, wherein the C-terminus of the B chain is covalently linked to the N-terminus of the A chain via the single-chain linking peptide, wherein said glucagon analogue is covalently linked to said single-chain insulin analogue.

3. The fusion peptide of claim 2 wherein the insulin analogue comprises the sequence of FVNQHLCGSHLVEALYLVCGEOGFFYTPETEEGPOO-GIVEQCCOSICSL EQLENYCN (SEQ ID NO: 122).

4. The fusion peptide of claim 2 wherein the C-terminal amino acid of the glucagon analogue is covalently linked to the insulin peptide, optionally via a fusion peptide linker, at the N-terminal alpha-amine of the B chain.

5. The fusion peptide of claim 2 wherein the C-terminal amino acid of the glucagon analogue is covalently linked to the insulin peptide, optionally via a fusion peptide linker, at the side chain of an amino acid at position B28 or B29, optionally wherein the amino acid at position B28 or B29 is Lys.

6. The fusion peptide of claim 2 wherein the C-terminal amino acid of the glucagon analogue is covalently linked to the insulin peptide at a side chain of an amino acid of said single-chain linking peptide.

7. A method of treating a patient afflicted with hypoglycemia or diabetes mellitus, comprising administering a physiologically effective amount of a composition comprising a fusion peptide comprising a stabilized glucagon analogue having a lower potency at the glucagon receptor than native glucagon and an insulin peptide, wherein the fusion peptide comprises the sequence HSQGTFTSDYSOKLD-SEOAQDFVQWLMNTEEKFVNOHLCGSHLVEALYL-VCGEOGFFYTPETEEGPOOGIVEQCCQSI CSLEQLE-NYCN (SEQ ID NO: 73), wherein the side chains of K13 and E17 form a lactam bridge.

8. A method of treating a patient afflicted with hypoglycemia or diabetes mellitus, comprising administering a physiologically effective amount of a composition comprising the fusion peptide of claim 2.

* * * * *

SEQUENCE LISTING

```
<160> NUMBER OF SEQ ID NOS: 132

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25


<210> SEQ ID NO 2
<211> LENGTH: 30
<212> TYPE: PRT
<213> ORGANISM: Artificial Sequence
<220> FEATURE:
<223> OTHER INFORMATION: glucagon peptide analog

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Arg
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: glucagon peptide analog

<400> SEQUENCE: 3

His Ser Gln Gly Thr Phe Thr Ser Asp Tyr Ser Lys Tyr Leu Asp Ser
1               5                   10                  15
```

```
Arg Arg Ala Gln Asp Phe Val Gln Trp Leu Met Asn Thr Lys
            20                  25                  30


<210> SEQ ID NO 4
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (30)..(30)
<223> OTHER INFORMATION: Xaa at position 30 is 2,4-Diaminobutyric acid
      (Dab)

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Xaa
            20                  25                  30


<210> SEQ ID NO 5
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (30)..(30)
<223> OTHER INFORMATION: Xaa at position 30 is ornithine

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Xaa
            20                  25                  30


<210> SEQ ID NO 6
<211> LENGTH: 30
<212> TYPE: PRT
<213> ORGANISM: Artificial Sequence
<220> FEATURE:
<223> OTHER INFORMATION: glucagon peptide analog

<400> SEQUENCE: 6

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Asp
            20                  25                  30


<210> SEQ ID NO 7
<211> LENGTH: 30
<212> TYPE: PRT
<213> ORGANISM: Artificial Sequence
<220> FEATURE:
<223> OTHER INFORMATION: glucagon peptide analog

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Glu
            20                  25                  30


<210> SEQ ID NO 8
<211> LENGTH: 30
```

<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is orinithin
<220> FEATURE:
<221> NAME/KEY: MISC_FEATURE
<222> LOCATION: (17)..(17)
<223> OTHER INFORMATION: Xaa at position 17 is orinithin
<220> FEATURE:
<221> NAME/KEY: MISC_FEATURE
<222> LOCATION: (18)..(18)
<223> OTHER INFORMATION: Xaa at position 18 is orinithin

<400> SEQUENCE: 8

```
His Ser Gln Gly Thr Phe Thr Ser Asp Tyr Ser Xaa Tyr Leu Asp Ser
1               5                   10                  15

Xaa Xaa Ala Gln Asp Phe Val Gln Trp Leu Met Asn Thr Lys
            20                  25                  30
```

<210> SEQ ID NO 9
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 9

```
His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr
            20                  25
```

<210> SEQ ID NO 10
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.

<400> SEQUENCE: 10

```
His Ser Gln Gly Thr Phe Thr Ser Asp Tyr Ser Lys Lys Leu Asp Ser
1               5                   10                  15

Glu Arg Ala Gln Asp Phe Val Gln Trp Leu Met Asn Thr
            20                  25
```

<210> SEQ ID NO 11
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 11

```
His Ser Gln Gly Thr Phe Thr Ser Asp Tyr Ser Lys Tyr Leu Asp Ser
1               5                   10                  15

Lys Arg Ala Gln Glu Phe Val Gln Trp Leu Met Asn Thr
            20                  25
```

<210> SEQ ID NO 12
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 12

```
His Ser Gln Gly Thr Phe Thr Ser Asp Tyr Ser Lys Tyr Leu Asp Ser
1               5                   10                  15

Arg Arg Ala Gln Asp Phe Val Lys Trp Leu Met Glu Thr
            20                  25
```

<210> SEQ ID NO 13
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine

<400> SEQUENCE: 13

```
His Ser Gln Gly Thr Phe Thr Ser Asp Tyr Ser Xaa Tyr Leu Asp Ser
1               5                   10                  15

Lys Arg Ala Gln Glu Phe Val Gln Trp Leu Met Asn Thr Lys
            20                  25                  30
```

<210> SEQ ID NO 14
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(13)
<223> OTHER INFORMATION: Xaa at position 13 is D-Cys

<400> SEQUENCE: 14

```
His Ser Gln Gly Thr Phe Thr Ser Asp Tyr Ser Lys Xaa Leu Asp Cys
1               5                   10                  15

Arg Arg Ala Gln Asp Phe Val Gln Trp Leu Met Asn Thr
            20                  25
```

<210> SEQ ID NO 15
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (16)..(16)
<223> OTHER INFORMATION: Xaa at position is D-Cys

<400> SEQUENCE: 15

```
His Ser Gln Gly Thr Phe Thr Ser Asp Tyr Ser Lys Tyr Leu Asp Xaa
1               5                   10                  15

Arg Arg Cys Gln Asp Phe Val Gln Trp Leu Met Asn Thr
            20                  25
```

<210> SEQ ID NO 16
<211> LENGTH: 29
<212> TYPE: PRT

<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (17)..(17)
<223> OTHER INFORMATION: Xaa at position 17 is D-Cys

<400> SEQUENCE: 16

His Ser Gln Gly Thr Phe Thr Ser Asp Tyr Ser Lys Tyr Leu Asp Ser
1               5                   10                  15

Xaa Arg Ala Cys Asp Phe Val Gln Trp Leu Met Asn Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 17

His Ser Gln Gly Thr Phe Thr Ser Asp Tyr Ser Lys Tyr Leu Asp Ser
1               5                   10                  15

Arg Xaa Ala Gln Cys Phe Val Gln Trp Leu Met Asn Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 18

His Ser Gln Gly Thr Phe Thr Ser Asp Tyr Ser Lys Tyr Leu Asp Ser
1               5                   10                  15

Arg Arg Ala Xaa Asp Phe Cys Gln Trp Leu Met Asn Thr
            20                  25

<210> SEQ ID NO 19
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (21)..(21)
<223> OTHER INFORMATION: Xaa at position 21 is D-Cys

<400> SEQUENCE: 19

His Ser Gln Gly Thr Phe Thr Ser Asp Tyr Ser Lys Tyr Leu Asp Ser
1               5                   10                  15

Arg Arg Ala Gln Xaa Phe Val Cys Trp Leu Met Asn Thr
            20                  25

<210> SEQ ID NO 20
<211> LENGTH: 29

<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 20

```
His Ser Gln Gly Thr Phe Thr Ser Asp Tyr Ser Lys Tyr Leu Asp Ser
1               5                   10                  15

Arg Arg Ala Gln Asp Phe Val Xaa Trp Leu Cys Asn Thr
            20                  25
```

<210> SEQ ID NO 21
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 17 is ornithine

<400> SEQUENCE: 21

```
His Ser Gln Gly Thr Phe Thr Ser Asp Tyr Ser Xaa Tyr Leu Asp Ser
1               5                   10                  15

Xaa Xaa Ala Gln Asp Phe Val Gln Trp Leu Met Asn Thr Glu Glu Lys
            20                  25                  30
```

<210> SEQ ID NO 22
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (16)..(16)
<223> OTHER INFORMATION: Xaa at position 16 is Aib
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 17 is ornithine

<400> SEQUENCE: 22

```
His Ser Gln Gly Thr Phe Thr Ser Asp Tyr Ser Xaa Tyr Leu Asp Xaa
1               5                   10                  15

Xaa Xaa Ala Gln Asp Phe Val Gln Trp Leu Met Asn Thr Glu Glu Lys
            20                  25                  30
```

<210> SEQ ID NO 23

<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 23

```
His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Met Asn Thr Glu Glu Lys
            20                  25                  30
```

<210> SEQ ID NO 24
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (9)..(13)
<223> OTHER INFORMATION: lactam ring formed between side chains of Xaa at position 9 and 13.
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 24

```
His Ser Gln Gly Thr Phe Thr Ser Lys Tyr Ser Xaa Glu Leu Asp Ser
1               5                   10                  15

Xaa Xaa Ala Gln Asp Phe Val Gln Trp Leu Met Asn Thr Glu Glu Lys
            20                  25                  30
```

<210> SEQ ID NO 25
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(16)
<223> OTHER INFORMATION: lactam ring formed between side chains of Xaa at position 12 and 16.
<220> FEATURE:
<221> NAME/KEY: MISC_FEATURE
<222> LOCATION: (17)..(17)
<220> FEATURE:
<221> NAME/KEY: MISC_FEATURE
<222> LOCATION: (17)..(17)
<223> OTHER INFORMATION: Xaa at position 17 is onithine
<220> FEATURE:
<221> NAME/KEY: MISC_FEATURE
<222> LOCATION: (18)..(18)
<223> OTHER INFORMATION: Xaa at position 18 is onithine

<400> SEQUENCE: 25

His Ser Gln Gly Thr Phe Thr Ser Asp Tyr Ser Lys Tyr Leu Asp Glu
1 5 10 15

Xaa Xaa Ala Gln Asp Phe Val Gln Trp Leu Met Asn Thr Glu Glu Lys
20 25 30

<210> SEQ ID NO 26
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(21)
<223> OTHER INFORMATION: lactam ring formed between side chains of Xaa at position 17 and 21.
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 26

His Ser Gln Gly Thr Phe Thr Ser Asp Tyr Ser Xaa Tyr Leu Asp Ser
1 5 10 15

Lys Xaa Ala Gln Glu Phe Val Gln Trp Leu Met Asn Thr Glu Glu Lys
20 25 30

<210> SEQ ID NO 27
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (24)..(28)
<223> OTHER INFORMATION: lactam ring formed between side chains of Xaa at position 24 and 28.

<400> SEQUENCE: 27

His Ser Gln Gly Thr Phe Thr Ser Asp Tyr Ser Xaa Tyr Leu Asp Ser
1 5 10 15

Xaa Xaa Ala Gln Asp Phe Val Lys Trp Leu Met Glu Thr Glu Glu Lys
20 25 30

<210> SEQ ID NO 28
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (2)..(2)
<223> OTHER INFORMATION: Xaa at position 2 is D-Cys
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 28

```
His Xaa Gln Gly Cys Phe Thr Ser Asp Tyr Ser Xaa Tyr Leu Asp Ser
1               5                   10                  15

Xaa Xaa Cys Gln Asp Phe Val Gln Trp Leu Met Asn Thr Glu Glu Lys
            20                  25                  30
```

<210> SEQ ID NO 29
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is orinithine
<220> FEATURE:
<221> NAME/KEY: MISC_FEATURE
<222> LOCATION: (16)..(16)
<223> OTHER INFORMATION: Xaa at position 16 is D-Cys
<220> FEATURE:
<221> NAME/KEY: MISC_FEATURE
<222> LOCATION: (17)..(17)
<223> OTHER INFORMATION: Xaa at position 17 is orinithine
<220> FEATURE:
<221> NAME/KEY: MISC_FEATURE
<222> LOCATION: (18)..(18)
<223> OTHER INFORMATION: Xaa at position 18 is orinithine

<400> SEQUENCE: 29

```
His Ser Gln Gly Thr Phe Thr Ser Asp Tyr Ser Xaa Tyr Leu Asp Xaa
1               5                   10                  15

Cys Gln Asp Phe Val Gln Trp Leu Met Asn Thr Glu Glu Lys
            20                  25                  30
```

<210> SEQ ID NO 30
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 30

His Ser Gln Gly Thr Phe Thr Ser Asp Tyr Ser Xaa Tyr Leu Asp Ser
1 5 10 15

Xaa Xaa Ala Xaa Asp Phe Cys Gln Trp Leu Met Asn Thr Glu Glu Lys
20 25 30

<210> SEQ ID NO 31
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (21)..(21)
<223> OTHER INFORMATION: Xaa at position 21 is D-Cys

<400> SEQUENCE: 31

His Ser Gln Gly Thr Phe Thr Ser Asp Tyr Ser Xaa Tyr Leu Asp Ser
1 5 10 15

Xaa Xaa Ala Gln Xaa Phe Val Cys Trp Leu Met Asn Thr Glu Glu Lys
20 25 30

<210> SEQ ID NO 32
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 32

His Ser Gln Gly Thr Phe Thr Ser Asp Tyr Ser Xaa Tyr Leu Asp Ser
1 5 10 15

Xaa Xaa Ala Gln Asp Phe Val Xaa Trp Leu Cys Asn Thr Glu Glu Lys
20 25 30

<210> SEQ ID NO 33
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 33

His Ser Gln Gly Thr Phe Thr Ser Asp Tyr Ser Lys Tyr Leu Asp Ser
1 5 10 15

Cys Arg Ala Gln Cys Phe Val Gln Trp Leu Met Asn Thr
20 25

<210> SEQ ID NO 34
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 34

His Ser Gln Gly Thr Phe Thr Ser Asp Tyr Ser Lys Cys Leu Asp Ser
1 5 10 15

Arg Arg Ala Cys Asp Phe Val Gln Trp Leu Met Asn Thr
20 25

<210> SEQ ID NO 35
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 35

His Ser Gln Gly Thr Phe Thr Ser Asp Tyr Ser Lys Tyr Cys Asp Ser
1 5 10 15

Arg Arg Ala Gln Cys Phe Val Gln Trp Leu Met Asn Thr
20 25

<210> SEQ ID NO 36
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 36

His Ser Gln Gly Thr Phe Thr Ser Asp Tyr Ser Lys Tyr Leu Asp Glu
1 5 10 15

Cys Arg Ala Gln Asp Phe Val Cys Trp Leu Met Asn Thr
20 25

<210> SEQ ID NO 37
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 37

His Ser Gln Gly Thr Phe Thr Ser Asp Tyr Ser Lys Tyr Leu Asp Ser
1 5 10 15

Arg Arg Ala Cys Asp Phe Val Gln Trp Leu Cys Asn Thr
20 25

<210> SEQ ID NO 38
<211> LENGTH: 29
<212> TYPE: PRT
<213> ORGANISM: Artificial Sequence
<220> FEATURE:

<223> OTHER INFORMATION: glucagon peptide analog

<400> SEQUENCE: 38

His Ser Gln Gly Thr Phe Thr Ser Asp Tyr Ser Lys Tyr Leu Asp Glu
1 5 10 15

Arg Arg Ala Gln Cys Phe Val Gln Trp Leu Met Cys Thr
20 25

<210> SEQ ID NO 39
<211> LENGTH: 49
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (22)..(22)
<223> OTHER INFORMATION: Xaa at position 22 is ornithine

<400> SEQUENCE: 39

Phe Val Asn Gln His Leu Cys Gly Ser His Leu Val Glu Ala Leu Tyr
1 5 10 15

Leu Val Cys Gly Glu Xaa Gly Phe Phe Tyr Thr Glu Gly Ile Leu Glu
20 25 30

Gln Cys Cys Glu Ser Ile Cys Ser Leu Glu Gln Leu Glu Asn Tyr Cys
35 40 45

Asn

<210> SEQ ID NO 40
<211> LENGTH: 57
<212> TYPE: PRT
<213> ORGANISM: Artificial Sequence
<220> FEATURE:
<223> OTHER INFORMATION: glucagon peptide analog

<400> SEQUENCE: 40

Phe Val Asn Gln His Leu Cys Gly Ser His Leu Val Glu Ala Leu Tyr
1 5 10 15

Leu Val Cys Gly Glu Glu Gly Phe Phe Tyr Thr Pro Glu Thr Glu Ala
20 25 30

Ala Ala Ala Ala Gly Ile Val Glu Gln Cys Cys Thr Ser Ile Cys Ser
35 40 45

Leu Glu Gln Leu Glu Asn Tyr Cys Asn
50 55

<210> SEQ ID NO 41
<211> LENGTH: 80
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (17)..(17)
<223> OTHER INFORMATION: Xaa at position 17 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (54)..(54)

<223> OTHER INFORMATION: Xaa at position 54 is ornithine

<400> SEQUENCE: 41

```
His Ser Gln Gly Thr Phe Thr Ser Asp Tyr Ser Xaa Tyr Leu Asp Ser
1               5                   10                  15

Xaa Xaa Ala Gln Asp Phe Val Gln Trp Leu Met Asn Thr Glu Glu Lys
            20                  25                  30

Phe Val Asn Gln His Leu Cys Gly Ser His Leu Val Glu Ala Leu Tyr
        35                  40                  45

Leu Val Cys Gly Glu Xaa Gly Phe Phe Tyr Thr Glu Gly Ile Leu Glu
    50                  55                  60

Gln Cys Cys Glu Ser Ile Cys Leu Glu Gln Leu Glu Asn Tyr Cys Asn
65                  70                  75                  80
```

<210> SEQ ID NO 42
<211> LENGTH: 87
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 42

```
His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Met Asn Thr Glu Glu Lys
            20                  25                  30

Phe Val Asn Gln His Leu Cys Gly Ser His Leu Val Glu Ala Leu Tyr
        35                  40                  45

Leu Val Cys Gly Glu Gly Phe Phe Tyr Thr Pro Glu Thr Glu Ala Ala
    50                  55                  60

Ala Ala Ala Gly Ile Val Glu Gln Cys Cys Thr Ser Ile Cys Leu Glu
65                  70                  75                  80

Gln Leu Glu Asn Tyr Cys Asn
                85
```

<210> SEQ ID NO 43
<211> LENGTH: 85
<212> TYPE: PRT
<213> ORGANISM: Artificial Sequence
<220> FEATURE:
<223> OTHER INFORMATION: glucagon peptide analog

<400> SEQUENCE: 43

```
Phe Val Asn Gln His Leu Cys Gly Ser His Leu Val Glu Ala Leu Tyr
1               5                   10                  15

Leu Val Cys Gly Glu Gly Phe Phe Tyr Thr Pro Lys Thr Arg Arg Glu
            20                  25                  30

Ala Glu Asp Leu Gln Val Gly Gln Val Glu Leu Gly Gly Gly Pro Gly
        35                  40                  45

Ala Gly Ser Leu Gln Pro Leu Ala Leu Glu Gly Ser Leu Gln Lys Arg
    50                  55                  60

Gly Ile Val Glu Gln Cys Cys Thr Ser Ile Cys Ser Leu Tyr Gln Leu
65                  70                  75                  80
```

Glu Asn Tyr Cys Asn
85

<210> SEQ ID NO 44
<211> LENGTH: 21
<212> TYPE: PRT
<213> ORGANISM: Artificial Sequence
<220> FEATURE:
<223> OTHER INFORMATION: glucagon peptide analog

<400> SEQUENCE: 44

Gly Ile Val Glu Gln Cys Cys Thr Ser Ile Cys Ser Leu Tyr Gln Leu
1 5 10 15

Glu Asn Tyr Cys Asn
20

<210> SEQ ID NO 45
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 45

Phe Val Asn Gln His Leu Cys Gly Ser His Leu Val Glu Ala Leu Tyr
1 5 10 15

Leu Val Cys Gly Glu Gly Phe Phe Tyr Thr Pro Lys Thr
20 25

<210> SEQ ID NO 46
<211> LENGTH: 29
<212> TYPE: PRT
<213> ORGANISM: Artificial Sequence
<220> FEATURE:
<223> OTHER INFORMATION: glucagon peptide analog

<400> SEQUENCE: 46

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

<210> SEQ ID NO 47
<211> LENGTH: 32
<212> TYPE: PRT
<213> ORGANISM: Artificial Sequence
<220> FEATURE:
<223> OTHER INFORMATION: glucagon peptide analog

<400> SEQUENCE: 47

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr Glu Glu Lys
20 25 30

<210> SEQ ID NO 48
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine

<400> SEQUENCE: 48

His Ser Gln Gly Thr Phe Thr Ser Asp Tyr Ser Xaa Lys Leu Asp Ser
1 5 10 15

Glu Xaa Ala Gln Asp Phe Val Gln Trp Leu Met Asn Thr Glu Glu Lys
20 25 30

<210> SEQ ID NO 49
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 49

His Ser Gln Gly Thr Phe Thr Ser Asp Tyr Ser Lys Lys Leu Asp Ser
1 5 10 15

Glu Xaa Ala Gln Cys Phe Val Gln Trp Leu Met Asn Thr
20 25

<210> SEQ ID NO 50
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 50

His Ser Gln Gly Thr Phe Thr Ser Asp Tyr Ser Lys Lys Leu Asp Ser
1 5 10 15

Glu Xaa Ala Gln Cys Phe Val Gln Trp Leu Met Asn Thr Glu Glu Lys
20 25 30

<210> SEQ ID NO 51
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 51

His Ser Gln Gly Thr Phe Thr Ser Asp Tyr Ser Xaa Lys Leu Asp Ser
1 5 10 15

Glu Xaa Ala Gln Cys Phe Val Gln Trp Leu Met Asn Thr Glu Glu Lys
20 25 30

<210> SEQ ID NO 52

<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 52

```
His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Met Asn Thr
            20                  25
```

<210> SEQ ID NO 53
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 53

```
His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Met Asn Thr Glu Glu Lys
            20                  25                  30
```

<210> SEQ ID NO 54
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 54

```
His Ser Gln Gly Thr Phe Thr Ser Asp Tyr Ser Xaa Lys Leu Asp Ser
1               5                   10                  15

Glu Arg Ala Xaa Asp Phe Cys Gln Trp Leu Met Asn Thr Glu Glu Lys
            20                  25                  30
```

<210> SEQ ID NO 55
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 55

```
His Ser Gln Gly Thr Phe Thr Ser Asp Tyr Ser Lys Lys Leu Asp Ser
1               5                   10                  15
```

Glu Arg Ala Gln Asp Phe Val Xaa Trp Leu Cys Asn Thr
20 25

<210> SEQ ID NO 56
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 56

His Ser Gln Gly Thr Phe Thr Ser Asp Tyr Ser Lys Lys Leu Asp Ser
1 5 10 15

Glu Arg Ala Gln Asp Phe Val Xaa Trp Leu Cys Asn Thr Glu Glu Lys
20 25 30

<210> SEQ ID NO 57
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 57

His Ser Gln Gly Thr Phe Thr Ser Asp Tyr Ser Xaa Lys Leu Asp Ser
1 5 10 15

Glu Arg Ala Gln Asp Phe Val Xaa Trp Leu Cys Asn Thr Glu Glu Lys
20 25 30

<210> SEQ ID NO 58
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (27)..(27)
<223> OTHER INFORMATION: Xaa at position 27 is D-Cys

<400> SEQUENCE: 58

His Ser Gln Gly Thr Phe Thr Ser Asp Tyr Ser Lys Lys Leu Asp Ser
1 5 10 15

Glu Arg Ala Gln Asp Phe Val Gln Trp Leu Xaa Asn Thr Cys
20 25 30

<210> SEQ ID NO 59
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (27)..(27)
<223> OTHER INFORMATION: Xaa at position 27 is D-Cys

<400> SEQUENCE: 59

His Ser Gln Gly Thr Phe Thr Ser Asp Tyr Ser Lys Lys Leu Asp Ser
1 5 10 15

Glu Arg Ala Gln Asp Phe Val Gln Trp Leu Xaa Asn Thr Cys Glu Glu
20 25 30

Lys

<210> SEQ ID NO 60
<211> LENGTH: 21
<212> TYPE: PRT
<213> ORGANISM: Homo sapiens

<400> SEQUENCE: 60

Gly Ile Val Glu Gln Cys Cys Thr Ser Ile Cys Ser Leu Tyr Gln Leu
1 5 10 15

Glu Asn Tyr Cys Asn
20

<210> SEQ ID NO 61
<211> LENGTH: 30
<212> TYPE: PRT
<213> ORGANISM: Homo sapiens

<400> SEQUENCE: 61

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 62
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (17)..(17)
<223> OTHER INFORMATION: Xaa at position 17 is Orn
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (20)..(24)
<223> OTHER INFORMATION: lactam ring formed between side chains of Xaa at position 20 and 24.

<400> SEQUENCE: 62

His Ser Gln Gly Thr Phe Thr Ser Asp Tyr Ser Xaa Tyr Leu Asp Ser
1 5 10 15

Xaa Xaa Ala Lys Asp Phe Val Glu Trp Leu Met Asn Thr Glu Glu Lys
20 25 30

<210> SEQ ID NO 63
<211> LENGTH: 32
<212> TYPE: PRT
<213> ORGANISM: Artificial Sequence
<220> FEATURE:
<223> OTHER INFORMATION: glucagon peptide analog
<220> FEATURE:

<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (17)..(17)
<223> OTHER INFORMATION: Xaa at position 17 is Orn
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (24)..(28)
<223> OTHER INFORMATION: lactam ring formed between side chains of Xaa at position 24 and 28.

<400> SEQUENCE: 63

```
His Ser Gln Gly Thr Phe Thr Ser Asp Tyr Ser Xaa Tyr Leu Asp Ser
1               5                   10                  15

Xaa Xaa Ala Gln Asp Phe Val Glu Trp Leu Met Lys Thr Glu Glu Lys
            20                  25                  30
```

<210> SEQ ID NO 64
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa at position 13 and 17
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (20)..(20)
<223> OTHER INFORMATION: Xaa at position 18 is D-Cys

<400> SEQUENCE: 64

```
His Ser Gln Gly Thr Phe Thr Ser Asp Tyr Ser Xaa Lys Leu Asp Ser
1               5                   10                  15

Glu Xaa Ala Xaa Asp Phe Cys Gln Trp Leu Met Asn Thr Glu Glu Lys
            20                  25                  30
```

<210> SEQ ID NO 65
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa at position 13 and 17
<220> FEATURE:

```
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (20)..(20)
<223> OTHER INFORMATION: Xaa at position 20 is D-Cys
<220> FEATURE:
<221> NAME/KEY: MISC_FEATURE
<222> LOCATION: (21)..(21)
<223> OTHER INFORMATION: Xaa at position 21 is D-Cys

<400> SEQUENCE: 65

His Ser Gln Gly Thr Phe Thr Ser Asp Tyr Ser Xaa Lys Leu Asp Ser
1               5                   10                  15

Glu Xaa Ala Gln Xaa Phe Val Cys Trp Leu Met Asn Thr Glu Glu Lys
            20                  25                  30


<210> SEQ ID NO 66
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa
      at position 24 and 28.
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 66

His Ser Gln Gly Thr Phe Thr Ser Asp Tyr Ser Xaa Lys Leu Asp Ser
1               5                   10                  15

Glu Xaa Ala Gln Asp Phe Val Xaa Trp Leu Cys Asn Thr Glu Glu Lys
            20                  25                  30


<210> SEQ ID NO 67
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.

<400> SEQUENCE: 67

His Ser Gln Gly Thr Phe Thr Ser Asp Tyr Ser Lys Lys Leu Asp Ser
1               5                   10                  15

Glu Arg Ala Gln Asp Phe Val Gln Trp Leu Pro Asn Thr Gly Gly Gly
            20                  25                  30


<210> SEQ ID NO 68
<211> LENGTH: 32
<212> TYPE: PRT
<213> ORGANISM: Artificial Sequence
```

<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 68

His Ser Gln Gly Thr Phe Thr Ser Asp Tyr Ser Lys Lys Leu Asp Ser
1               5                   10                  15

Glu Xaa Ala Gln Cys Phe Val Gln Trp Leu Pro Asn Thr Gly Gly Gly
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 69

His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Pro Asn Thr Gly Gly Gly
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (21)..(21)
<223> OTHER INFORMATION: Xaa at position 21 is D-Cys

<400> SEQUENCE: 70

His Ser Gln Gly Thr Phe Thr Ser Asp Tyr Ser Lys Lys Leu Asp Ser
1               5                   10                  15

Glu Arg Ala Gln Xaa Phe Val Cys Trp Leu Pro Asn Thr Gly Gly Gly
            20                  25                  30

<210> SEQ ID NO 71
<211> LENGTH: 57
<212> TYPE: PRT
<213> ORGANISM: Artificial Sequence
<220> FEATURE:
<223> OTHER INFORMATION: insulin peptide analog
<220> FEATURE:
<221> NAME/KEY: MISC_FEATURE
<222> LOCATION: (22)..(22)
<223> OTHER INFORMATION: Xaa at position 22 is Orn.
<220> FEATURE:
<221> NAME/KEY: MISC_FEATURE
<222> LOCATION: (35)..(35)
<223> OTHER INFORMATION: Xaa at position 35 is Orn.
<220> FEATURE:
<221> NAME/KEY: MISC_FEATURE
<222> LOCATION: (36)..(36)
<223> OTHER INFORMATION: Xaa at position 36 is Orn.

<400> SEQUENCE: 71

```
Phe Val Asn Gln His Leu Cys Gly Ser His Leu Val Glu Ala Leu Tyr
1               5                   10                  15

Leu Val Cys Gly Glu Xaa Gly Phe Phe Tyr Thr Pro Glu Thr Glu Glu
            20                  25                  30

Gly Pro Xaa Xaa Gly Ile Val Glu Gln Cys Cys Gln Ser Ile Cys Ser
        35                  40                  45

Leu Glu Gln Leu Glu Asn Tyr Cys Asn
    50                  55
```

<210> SEQ ID NO 72
<211> LENGTH: 57
<212> TYPE: PRT
<213> ORGANISM: Artificial Sequence
<220> FEATURE:
<223> OTHER INFORMATION: insulin peptide analog
<220> FEATURE:
<221> NAME/KEY: MISC_FEATURE
<222> LOCATION: (22)..(22)
<223> OTHER INFORMATION: Xaa at position 22 is Orn.
<220> FEATURE:
<221> NAME/KEY: MISC_FEATURE
<222> LOCATION: (35)..(35)
<223> OTHER INFORMATION: Xaa at position 35 is Orn.
<220> FEATURE:
<221> NAME/KEY: MISC_FEATURE
<222> LOCATION: (36)..(36)
<223> OTHER INFORMATION: Xaa at position 36 is Orn.

<400> SEQUENCE: 72

```
Phe Val Asn Gln His Leu Cys Gly Ser His Leu Val Glu Ala Leu Tyr
1               5                   10                  15

Leu Val Cys Gly Glu Xaa Gly Phe Phe Tyr Thr Pro Glu Thr Glu Glu
            20                  25                  30

Gly Pro Xaa Xaa Gly Ile Leu Glu Gln Cys Cys Gln Ser Ile Cys Ser
        35                  40                  45

Leu Glu Gln Leu Glu Asn Tyr Cys Asn
    50                  55
```

<210> SEQ ID NO 73
<211> LENGTH: 89
<212> TYPE: PRT
<213> ORGANISM: Artificial Sequence
<220> FEATURE:
<223> OTHER INFORMATION: glucagon/insulin fusion peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (54)..(54)
<223> OTHER INFORMATION: Xaa at position 54 is ornithine
<220> FEATURE:

```
<221> NAME/KEY: MISC_FEATURE
<222> LOCATION: (67)..(67)
<223> OTHER INFORMATION: Xaa at position 67 is ornithine
<220> FEATURE:
<221> NAME/KEY: MISC_FEATURE
<222> LOCATION: (68)..(68)
<223> OTHER INFORMATION: Xaa at position 68 is ornithine

<400> SEQUENCE: 73

His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Met Asn Thr Glu Glu Lys
            20                  25                  30

Phe Val Asn Gln His Leu Cys Gly Ser His Leu Val Glu Ala Leu Tyr
        35                  40                  45

Leu Val Cys Gly Glu Xaa Gly Phe Phe Tyr Thr Pro Glu Thr Glu Glu
    50                  55                  60

Gly Pro Xaa Xaa Gly Ile Val Glu Gln Cys Cys Gln Ser Ile Cys Ser
65                  70                  75                  80

Leu Glu Gln Leu Glu Asn Tyr Cys Asn
                85


<210> SEQ ID NO 74
<211> LENGTH: 89
<212> TYPE: PRT
<213> ORGANISM: Artificial Sequence
<220> FEATURE:
<223> OTHER INFORMATION: glucagon/insulin fusion peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (54)..(54)
<223> OTHER INFORMATION: Xaa at position 54 is ornithine
<220> FEATURE:
<221> NAME/KEY: MISC_FEATURE
<222> LOCATION: (67)..(67)
<223> OTHER INFORMATION: Xaa at position 67 is ornithine
<220> FEATURE:
<221> NAME/KEY: MISC_FEATURE
<222> LOCATION: (68)..(68)
<223> OTHER INFORMATION: Xaa at position 68 is ornithine

<400> SEQUENCE: 74

His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Met Asn Thr Glu Glu Lys
            20                  25                  30

Phe Val Asn Gln His Leu Cys Gly Ser His Leu Val Glu Ala Leu Tyr
        35                  40                  45

Leu Val Cys Gly Glu Xaa Gly Phe Phe Tyr Thr Pro Glu Thr Glu Glu
    50                  55                  60

Gly Pro Xaa Xaa Gly Ile Leu Glu Gln Cys Cys Gln Ser Ile Cys Ser
65                  70                  75                  80

Leu Glu Gln Leu Glu Asn Tyr Cys Asn
                85


<210> SEQ ID NO 75
<211> LENGTH: 89
```

<212> TYPE: PRT
<213> ORGANISM: Artificial Sequence
<220> FEATURE:
<223> OTHER INFORMATION: glucagon/insulin fusion peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (54)..(54)
<223> OTHER INFORMATION: Xaa at position 54 is ornithine
<220> FEATURE:
<221> NAME/KEY: MISC_FEATURE
<222> LOCATION: (67)..(67)
<223> OTHER INFORMATION: Xaa at position 67 is ornithine
<220> FEATURE:
<221> NAME/KEY: MISC_FEATURE
<222> LOCATION: (68)..(68)
<223> OTHER INFORMATION: Xaa at position 68 is ornithine

<400> SEQUENCE: 75

```
His Ser Gln Gly Thr Phe Thr Ser Lys Tyr Ser Xaa Lys Leu Asp Ser
1               5                   10                  15

Glu Xaa Ala Gln Asp Phe Val Gln Trp Leu Met Asn Thr Glu Glu Lys
            20                  25                  30

Phe Val Asn Gln His Leu Cys Gly Ser His Leu Val Glu Ala Leu Tyr
        35                  40                  45

Leu Val Cys Gly Glu Xaa Gly Phe Phe Tyr Thr Pro Glu Thr Glu Glu
    50                  55                  60

Gly Pro Xaa Xaa Gly Ile Val Glu Gln Cys Cys Gln Ser Ile Cys Ser
65                  70                  75                  80

Leu Glu Gln Leu Glu Asn Tyr Cys Asn
                85
```

<210> SEQ ID NO 76
<211> LENGTH: 89
<212> TYPE: PRT
<213> ORGANISM: Artificial Sequence
<220> FEATURE:
<223> OTHER INFORMATION: glucagon/insulin fusion peptide analog
<220> FEATURE:
<221> NAME/KEY: MISC_FEATURE
<222> LOCATION: (12)..(12)
<223> OTHER INFORMATION: Xaa at position 12 is ornithine
<220> FEATURE:
<221> NAME/KEY: MISC_FEATURE
<222> LOCATION: (18)..(18)
<223> OTHER INFORMATION: Xaa at position 18 is ornithine
<220> FEATURE:
<221> NAME/KEY: MISC_FEATURE
<222> LOCATION: (54)..(54)
<223> OTHER INFORMATION: Xaa at position 54 is ornithine
<220> FEATURE:
<221> NAME/KEY: MISC_FEATURE
<222> LOCATION: (67)..(67)
<223> OTHER INFORMATION: Xaa at position 67 is ornithine
<220> FEATURE:
<221> NAME/KEY: MISC_FEATURE
<222> LOCATION: (68)..(68)
<223> OTHER INFORMATION: Xaa at position 68 is ornithine

<400> SEQUENCE: 76

His Ser Gln Gly Thr Phe Thr Ser Lys Tyr Ser Xaa Lys Leu Asp Ser
1 5 10 15

Glu Xaa Ala Gln Asp Phe Val Gln Trp Leu Met Asn Thr Glu Glu Lys
20 25 30

Phe Val Asn Gln His Leu Cys Gly Ser His Leu Val Glu Ala Leu Tyr
35 40 45

Leu Val Cys Gly Glu Xaa Gly Phe Phe Tyr Thr Pro Glu Thr Glu Glu
50 55 60

Gly Pro Xaa Xaa Gly Ile Leu Glu Gln Cys Cys Gln Ser Ile Cys Ser
65 70 75 80

Leu Glu Gln Leu Glu Asn Tyr Cys Asn
85

<210> SEQ ID NO 77
<211> LENGTH: 86
<212> TYPE: PRT
<213> ORGANISM: Homo sapiens

<400> SEQUENCE: 77

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn
85

<210> SEQ ID NO 78
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.

<400> SEQUENCE: 78

His Ser Gln Gly Thr Phe Thr Ser Asp Tyr Ser Lys Lys Leu Asp Ser
1 5 10 15

Glu Arg Ala Gln Asp Phe Val Gln Trp Leu Met Asn Thr Xaa
20 25 30

<210> SEQ ID NO 79
<211> LENGTH: 32
<212> TYPE: PRT
<213> ORGANISM: Artificial Sequence
<220> FEATURE:

```
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys,
      Orn, Diamino-Butyric Acid or Diamino-Proprionic Acid
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-
      Butyric Acid or Diamino-Proprionic Acid

<400> SEQUENCE: 79

His Ser Gln Gly Thr Phe Thr Ser Asp Tyr Ser Lys Lys Leu Asp Ser
1               5                   10                  15

Glu Arg Ala Gln Asp Phe Val Gln Trp Leu Met Asn Thr Xaa Xaa Xaa
            20                  25                  30


<210> SEQ ID NO 80
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (30)..(30)
<223> OTHER INFORMATION: Xaa at position 30 is Ala, Gly, Glu, Orn,
      Diamino-Butyric Acid or Diamino-Proprionic Acid
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu
<220> FEATURE:
<221> NAME/KEY: MISC_FEATURE
<222> LOCATION: (32)..(32)
<223> OTHER INFORMATION: Xaa at position 32 is Lys or Arg

<400> SEQUENCE: 80

His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Met Asn Thr Xaa Xaa Xaa
            20                  25                  30


<210> SEQ ID NO 81
<211> LENGTH: 29
<212> TYPE: PRT
<213> ORGANISM: Artificial Sequence
<220> FEATURE:
<223> OTHER INFORMATION: glucagon peptide analog
<220> FEATURE:
```

<221> NAME/KEY: MISC_FEATURE
<222> LOCATION: (13)..(17)
<223> OTHER INFORMATION: lactam ring formed between side chains of Xaa
at position 13 and 17.
<220> FEATURE:
<221> NAME/KEY: MISC_FEATURE
<222> LOCATION: (18)..(18)
<223> OTHER INFORMATION: Xaa at position 18 is D-Cys

<400> SEQUENCE: 81

His Ser Gln Gly Thr Phe Thr Ser Asp Tyr Ser Lys Lys Leu Asp Ser
1 5 10 15

Glu Xaa Ala Gln Cys Phe Val Gln Trp Leu Met Asn Thr
20 25

<210> SEQ ID NO 82
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
at position 13 and 17.
<220> FEATURE:
<221> NAME/KEY: MISC_FEATURE
<222> LOCATION: (18)..(18)
<223> OTHER INFORMATION: Xaa at position 18 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys,
Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-
Butyric Acid or Diamino-Proprionic Acid.

<400> SEQUENCE: 82

His Ser Gln Gly Thr Phe Thr Ser Asp Tyr Ser Lys Lys Leu Asp Ser
1 5 10 15

Glu Xaa Ala Gln Cys Phe Val Gln Trp Leu Met Asn Thr Xaa Xaa Xaa
20 25 30

<210> SEQ ID NO 83
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa
at position 13 and 17.
<220> FEATURE:
<221> NAME/KEY: MISC_FEATURE
<222> LOCATION: (18)..(18)
<223> OTHER INFORMATION: Xaa at position 18 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys,
      Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
      Glu.
<220> FEATURE:
<221> NAME/KEY: MISC_FEATURE
<222> LOCATION: (32)..(32)
<223> OTHER INFORMATION: Xaa at position 32 is Lys or Arg.

<400> SEQUENCE: 83

His Ser Gln Gly Thr Phe Thr Ser Asp Tyr Ser Xaa Lys Leu Asp Ser
1               5                   10                  15

Glu Xaa Ala Gln Cys Phe Val Gln Trp Leu Met Asn Thr Xaa Xaa Xaa
            20                  25                  30

<210> SEQ ID NO 84
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (20)..(20)
<223> OTHER INFORMATION: Xaa at position 20 is D-Cys

<400> SEQUENCE: 84

His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Met Asn Thr
            20                  25

<210> SEQ ID NO 85
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (20)..(20)
<223> OTHER INFORMATION: Xaa at position 20 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys,
      Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
      Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-
      Butyric Acid or Diamino-Proprionic Acid.

```
<400> SEQUENCE: 85

His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Met Asn Thr Xaa Xaa Xaa
            20                  25                  30


<210> SEQ ID NO 86
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (20)..(20)
<223> OTHER INFORMATION: Xaa at position 20 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys,
      Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
      Glu.
<220> FEATURE:
<221> NAME/KEY: MISC_FEATURE
<222> LOCATION: (32)..(32)
<223> OTHER INFORMATION: Xaa at position 32 is Lys or Arg.

<400> SEQUENCE: 86

His Ser Gln Gly Thr Phe Thr Ser Asp Tyr Ser Xaa Lys Leu Asp Ser
1               5                   10                  15

Glu Xaa Ala Xaa Asp Phe Cys Gln Trp Leu Met Asn Thr Xaa Xaa Xaa
            20                  25                  30


<210> SEQ ID NO 87
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (24)..(24)
<223> OTHER INFORMATION: Xaa at position 24 is D-Cys

<400> SEQUENCE: 87

His Ser Gln Gly Thr Phe Thr Ser Asp Tyr Ser Lys Lys Leu Asp Ser
1               5                   10                  15
```

Glu Arg Ala Gln Asp Phe Val Xaa Trp Leu Cys Asn Thr
            20                  25

<210> SEQ ID NO 88
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(24)
<223> OTHER INFORMATION: Xaa at position 24 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-Butyric Acid or Diamino-Proprionic Acid.

<400> SEQUENCE: 88

His Ser Gln Gly Thr Phe Thr Ser Asp Tyr Ser Lys Lys Leu Asp Ser
1               5                   10                  15

Glu Arg Ala Gln Asp Phe Val Xaa Trp Leu Cys Asn Thr Xaa Xaa Xaa
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (24)..(24)
<223> OTHER INFORMATION: Xaa at position 24 is D-Cys
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:

<221> NAME/KEY: MISC_FEATURE
<222> LOCATION: (32)..(32)
<223> OTHER INFORMATION: Xaa at position 32 is Lys or Arg.

<400> SEQUENCE: 89

His Ser Gln Gly Thr Phe Thr Ser Asp Tyr Ser Xaa Lys Leu Asp Ser
1 5 10 15

Glu Xaa Ala Gln Asp Phe Val Xaa Trp Leu Cys Asn Thr Xaa Xaa Xaa
20 25 30

<210> SEQ ID NO 90
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (27)..(27)
<223> OTHER INFORMATION: Xaa at position 27 is D-Cys

<400> SEQUENCE: 90

His Ser Gln Gly Thr Phe Thr Ser Asp Tyr Ser Lys Lys Leu Asp Ser
1 5 10 15

Glu Arg Ala Gln Asp Phe Val Gln Trp Leu Xaa Asn Thr Cys
20 25 30

<210> SEQ ID NO 91
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (27)..(27)
<223> OTHER INFORMATION: Xaa at position 27 is D-Cys
<220> FEATURE:
<221> NAME/KEY: MISC_FEATURE
<222> LOCATION: (31)..(31)
<223> OTHER INFORMATION: Xaa at position 31 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 91

His Ser Gln Gly Thr Phe Thr Ser Asp Tyr Ser Lys Lys Leu Asp Ser
1 5 10 15

Glu Arg Ala Gln Asp Phe Val Gln Trp Leu Xaa Asn Thr Cys Xaa Xaa
20 25 30

Xaa

<210> SEQ ID NO 92
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn
<220> FEATURE:
<221> NAME/KEY: MISC_FEATURE
<222> LOCATION: (27)..(27)
<223> OTHER INFORMATION: Xaa at position 27 is D-Cys.
<220> FEATURE:
<221> NAME/KEY: MISC_FEATURE
<222> LOCATION: (31)..(31)
<223> OTHER INFORMATION: Xaa at position 31 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Lys or Arg.

<400> SEQUENCE: 92

```
His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Xaa Asn Thr Cys Xaa Xaa
            20                  25                  30

Xaa
```

<210> SEQ ID NO 93
<211> LENGTH: 31
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (28)..(28)
<223> OTHER INFORMATION: Xaa at position 28 is D-Cys.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.

<400> SEQUENCE: 93

```
His Ser Gln Gly Thr Phe Thr Ser Asp Tyr Ser Lys Lys Leu Asp Ser
1               5                   10                  15

Glu Arg Ala Gln Asp Phe Val Gln Trp Leu Met Xaa Thr Xaa Cys
            20                  25                  30
```

<210> SEQ ID NO 94
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (28)..(28)
<223> OTHER INFORMATION: Xaa at position 28 is D-Cys.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 94

His Ser Gln Gly Thr Phe Thr Ser Asp Tyr Ser Lys Lys Leu Asp Ser
1 5 10 15

Glu Arg Ala Gln Asp Phe Val Gln Trp Leu Met Xaa Thr Xaa Cys Xaa
20 25 30

Xaa

<210> SEQ ID NO 95
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (28)..(28)
<223> OTHER INFORMATION: Xaa at position 28 is D-Cys.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)

<223> OTHER INFORMATION: Xaa at position 33 is Lys or Arg.

<400> SEQUENCE: 95

His Ser Gln Gly Thr Phe Thr Ser Asp Tyr Ser Xaa Lys Leu Asp Ser
1 5 10 15

Glu Xaa Ala Gln Asp Phe Val Gln Trp Leu Met Xaa Thr Xaa Cys Xaa
20 25 30

Xaa

<210> SEQ ID NO 96
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (20)..(24)
<223> OTHER INFORMATION: lactam ring formed between side chains of Xaa at position 20 and 24.

<400> SEQUENCE: 96

His Ser Gln Gly Thr Phe Thr Ser Asp Tyr Ser Lys Lys Leu Asp Ser
1 5 10 15

Glu Arg Ala Lys Asp Phe Val Glu Trp Leu Met Asn Thr
20 25

<210> SEQ ID NO 97
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (20)..(24)
<223> OTHER INFORMATION: lactam ring formed between side chains of Xaa at position 20 and 24.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.

<400> SEQUENCE: 97

His Ser Gln Gly Thr Phe Thr Ser Asp Tyr Ser Lys Lys Leu Asp Ser
1 5 10 15

Glu Arg Ala Lys Asp Phe Val Glu Trp Leu Met Asn Thr Xaa
20 25 30

<210> SEQ ID NO 98
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)

<223> OTHER INFORMATION: lactam ring formed between side chains of Xaa at position 13 and 17.
<220> FEATURE:
<221> NAME/KEY: MISC_FEATURE
<222> LOCATION: (20)..(24)
<223> OTHER INFORMATION: lactam ring formed between side chains of Xaa at position 20 and 24.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-Butyric Acid or Diamino-Proprionic Acid.

<400> SEQUENCE: 98

```
His Ser Gln Gly Thr Phe Thr Ser Asp Tyr Ser Lys Lys Leu Asp Ser
1               5                   10                  15

Glu Arg Ala Lys Asp Phe Val Glu Trp Leu Met Asn Thr Xaa Xaa Xaa
            20                  25                  30
```

<210> SEQ ID NO 99
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (20)..(24)
<223> OTHER INFORMATION: lactam ring formed between side chains of Xaa at position 20 and 24.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-Butyric Acid or Diamino-Proprionic Acid.

<400> SEQUENCE: 99

```
His Ser Gln Gly Thr Phe Thr Ser Asp Tyr Ser Xaa Lys Leu Asp Ser
1               5                   10                  15

Glu Xaa Ala Lys Asp Phe Val Glu Trp Leu Met Asn Thr Xaa Xaa Xaa
            20                  25                  30
```

<210> SEQ ID NO 100
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(28)
<223> OTHER INFORMATION: lactam ring formed between side chains of Xaa at position 24 and 28.

<400> SEQUENCE: 100

```
His Ser Gln Gly Thr Phe Thr Ser Asp Tyr Ser Lys Lys Leu Asp Ser
1               5                   10                  15

Glu Arg Ala Gln Asp Phe Val Lys Trp Leu Met Glu Thr
            20                  25
```

<210> SEQ ID NO 101
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(28)
<223> OTHER INFORMATION: lactam ring formed between side chains of Xaa at position 24 and 28.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.

<400> SEQUENCE: 101

```
His Ser Gln Gly Thr Phe Thr Ser Asp Tyr Ser Lys Lys Leu Asp Ser
1               5                   10                  15

Glu Arg Ala Gln Asp Phe Val Lys Trp Leu Met Glu Thr Xaa
            20                  25                  30
```

<210> SEQ ID NO 102
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(28)
<223> OTHER INFORMATION: lactam ring formed between side chains of Xaa at position 24 and 28.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-
      Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
      Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-
      Butyric Acid or Diamino-Proprionic Acid.

<400> SEQUENCE: 102

His Ser Gln Gly Thr Phe Thr Ser Asp Tyr Ser Lys Lys Leu Asp Ser
1               5                   10                  15

Glu Arg Ala Gln Asp Phe Val Lys Trp Leu Met Asn Glu Xaa Xaa Xaa
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (24)..(28)
<223> OTHER INFORMATION: lactam ring formed between side chains of Xaa
      at position 20 and 24.
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-
      Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
      Glu.
<220> FEATURE:
<221> NAME/KEY: MISC_FEATURE
<222> LOCATION: (32)..(32)
<223> OTHER INFORMATION: Xaa at position 32 is Lys or Arg.

<400> SEQUENCE: 103

His Ser Gln Gly Thr Phe Thr Ser Asp Tyr Ser Xaa Lys Leu Asp Ser
1               5                   10                  15

Glu Xaa Ala Gln Asp Phe Val Lys Trp Leu Met Glu Thr Xaa Xaa Xaa
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (27)..(31)
<223> OTHER INFORMATION: lactam ring formed between side chains of Xaa at position 27 and 31.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.

<400> SEQUENCE: 104

```
His Ser Gln Gly Thr Phe Thr Ser Asp Tyr Ser Lys Lys Leu Asp Ser
1               5                   10                  15

Glu Arg Ala Gln Asp Phe Val Gln Trp Leu Lys Asn Thr Xaa Glu
            20                  25                  30
```

<210> SEQ ID NO 105
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (27)..(31)
<223> OTHER INFORMATION: lactam ring formed between side chains of Xaa at position 27 and 31.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 105

```
His Ser Gln Gly Thr Phe Thr Ser Asp Tyr Ser Lys Lys Leu Asp Ser
1               5                   10                  15

Glu Arg Ala Gln Asp Phe Val Gln Trp Leu Xaa Asn Thr Xaa Glu Xaa
            20                  25                  30

Xaa
```

<210> SEQ ID NO 106
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)

<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (27)..(31)
<223> OTHER INFORMATION: lactam ring formed between side chains of Xaa at position 27 and 31.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 106

```
His Ser Gln Gly Thr Phe Thr Ser Asp Tyr Ser Xaa Lys Leu Asp Ser
1               5                   10                  15

Glu Xaa Ala Gln Asp Phe Val Gln Trp Leu Xaa Asn Thr Xaa Glu Xaa
            20                  25                  30

Xaa
```

<210> SEQ ID NO 107
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (20)..(27)
<223> OTHER INFORMATION: bifunctional bromacetyl linker connects the side chains of C20 and C27

<400> SEQUENCE: 107

```
His Ser Gln Gly Thr Phe Thr Ser Asp Tyr Ser Lys Lys Leu Asp Ser
1               5                   10                  15

Glu Arg Ala Cys Asp Phe Val Gln Trp Leu Cys Asn Thr
            20                  25
```

<210> SEQ ID NO 108
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (20)..(27)
<223> OTHER INFORMATION: bifunctional bromacetyl linker connects the side chains of C20 and C27
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-
Butyric Acid or Diamino-Proprionic Acid

<400> SEQUENCE: 108

His Ser Gln Gly Thr Phe Thr Ser Asp Tyr Ser Lys Lys Leu Asp Ser
1 5 10 15

Glu Arg Ala Cys Asp Phe Val Gln Trp Leu Cys Asn Thr Xaa
20 25 30

<210> SEQ ID NO 109
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
at position 13 and 17.
<220> FEATURE:
<221> NAME/KEY: MISC_FEATURE
<222> LOCATION: (20)..(27)
<223> OTHER INFORMATION: bifunctional bromacetyl linker connects the
side chains of C20 and C27
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-
Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or
Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-
Butyric Acid or Diamino-Proprionic Acid.

<400> SEQUENCE: 109

His Ser Gln Gly Thr Phe Thr Ser Asp Tyr Ser Lys Lys Leu Asp Ser
1 5 10 15

Glu Arg Ala Cys Asp Phe Val Gln Trp Leu Cys Asn Thr Xaa Xaa Xaa
20 25 30

<210> SEQ ID NO 110
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa
at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (20)..(27)

<223> OTHER INFORMATION: bifunctional bromacetyl linker connects the side chains of C20 and C27
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:
<221> NAME/KEY: MISC_FEATURE
<222> LOCATION: (32)..(32)
<223> OTHER INFORMATION: Xaa at position 32 is Lys or Arg.

<400> SEQUENCE: 110

```
His Ser Gln Gly Thr Phe Thr Ser Asp Tyr Ser Xaa Lys Leu Asp Ser
1               5                   10                  15

Glu Xaa Ala Cys Asp Phe Val Gln Trp Leu Cys Asn Thr Xaa Xaa Xaa
            20                  25                  30
```

<210> SEQ ID NO 111
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (21)..(28)
<223> OTHER INFORMATION: bifunctional bromacetyl linker connects the side chains of C21 and C28

<400> SEQUENCE: 111

```
His Ser Gln Gly Thr Phe Thr Ser Asp Tyr Ser Lys Lys Leu Asp Ser
1               5                   10                  15

Glu Arg Ala Gln Cys Phe Val Gln Trp Leu Met Cys Thr
            20                  25
```

<210> SEQ ID NO 112
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (21)..(28)
<223> OTHER INFORMATION: bifunctional bromacetyl linker connects the side chains of C21 and C28
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid

<400> SEQUENCE: 112

```
His Ser Gln Gly Thr Phe Thr Ser Asp Tyr Ser Lys Lys Leu Asp Ser
1               5                   10                  15
```

Glu Arg Ala Gln Cys Phe Val Gln Trp Leu Met Cys Thr Xaa
20 25 30

<210> SEQ ID NO 113
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (21)..(28)
<223> OTHER INFORMATION: bifunctional bromacetyl linker connects the side chains of C21 and C28
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.
<220> FEATURE:
<221> NAME/KEY: MISC_FEATURE
<222> LOCATION: (32)..(32)
<223> OTHER INFORMATION: Xaa at position 32 is Arg, Lys, Orn, Diamino-Butyric Acid or Diamino-Proprionic Acid.

<400> SEQUENCE: 113

His Ser Gln Gly Thr Phe Thr Ser Asp Tyr Ser Lys Lys Leu Asp Ser
1 5 10 15

Glu Arg Ala Gln Cys Phe Val Gln Trp Leu Met Cys Thr Xaa Xaa Xaa
20 25 30

<210> SEQ ID NO 114
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (21)..(28)
<223> OTHER INFORMATION: bifunctional bromacetyl linker connects the side chains of C21 and C28
<220> FEATURE:
<221> NAME/KEY: MISC_FEATURE
<222> LOCATION: (30)..(30)
<223> OTHER INFORMATION: Xaa at position 30 is Arg, Lys, Orn, Diamino-Butyric Acid or Diamino-Proprionic Acid.
<220> FEATURE:
<221> NAME/KEY: MISC_FEATURE
<222> LOCATION: (31)..(31)
<223> OTHER INFORMATION: Xaa at position 31 is Gly, Ala, Ser, Gln or Glu.

<220> FEATURE:
<221> NAME/KEY: MISC_FEATURE
<222> LOCATION: (32)..(32)
<223> OTHER INFORMATION: Xaa at position 32 is Lys or Arg.

<400> SEQUENCE: 114

His Ser Gln Gly Thr Phe Thr Ser Asp Tyr Ser Xaa Lys Leu Asp Ser
1 5 10 15

Glu Xaa Ala Gln Cys Phe Val Gln Trp Leu Met Cys Thr Xaa Xaa Xaa
20 25 30

<210> SEQ ID NO 115
<211> LENGTH: 31
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(31)
<223> OTHER INFORMATION: bifunctional bromacetyl linker connects the side chains of C24 and C31
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.

<400> SEQUENCE: 115

His Ser Gln Gly Thr Phe Thr Ser Asp Tyr Ser Lys Lys Leu Asp Ser
1 5 10 15

Glu Arg Ala Gln Asp Phe Val Cys Trp Leu Met Asn Thr Xaa Cys
20 25 30

<210> SEQ ID NO 116
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (24)..(31)
<223> OTHER INFORMATION: bifunctional bromacetyl linker connects the side chains of C24 and 31.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 116

His Ser Gln Gly Thr Phe Thr Ser Asp Tyr Ser Lys Lys Leu Asp Ser
1 5 10 15

Glu Arg Ala Gln Asp Phe Val Cys Trp Leu Met Asn Thr Xaa Cys Xaa
20 25 30

Xaa

<210> SEQ ID NO 117
<211> LENGTH: 33
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Orn.
<220> FEATURE:
<221> NAME/KEY: MISC_FEATURE
<222> LOCATION: (13)..(17)
<223> OTHER INFORMATION: lactam ring formed between side chains of Xaa at position 13 and 17.
<220> FEATURE:
<221> NAME/KEY: MISC_FEATURE
<222> LOCATION: (18)..(18)
<223> OTHER INFORMATION: Xaa at position 18 is Orn.
<220> FEATURE:
<221> NAME/KEY: MISC_FEATURE
<222> LOCATION: (24)..(31)
<223> OTHER INFORMATION: bifunctional bromacetyl linker connects the side chains of C24 and C31.
<220> FEATURE:
<221> NAME/KEY: MISC_FEATURE
<222> LOCATION: (30)..(30)
<223> OTHER INFORMATION: Xaa at position 30 is Ala, Gly, Glu, Arg, Lys, Orn, Diamino-Butyric Acid or Diamino-Proprionic Acid.
<220> FEATURE:
<221> NAME/KEY: MISC_FEATURE
<222> LOCATION: (32)..(32)
<223> OTHER INFORMATION: Xaa at position 32 is Gly, Ala, Ser, Gln or Glu.
<220> FEATURE:
<221> NAME/KEY: MISC_FEATURE
<222> LOCATION: (33)..(33)
<223> OTHER INFORMATION: Xaa at position 33 is Arg, Lys, Orn, Diamino-Butyric Acid or Diamino-Proprionic Acid.

<400> SEQUENCE: 117

His Ser Gln Gly Thr Phe Thr Ser Asp Tyr Ser Xaa Lys Leu Asp Ser
1 5 10 15

Glu Xaa Ala Gln Asp Phe Val Cys Trp Leu Met Asn Thr Xaa Cys Xaa
20 25 30

Xaa

<210> SEQ ID NO 118
<211> LENGTH: 29
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (12)..(12)
<223> OTHER INFORMATION: Xaa at position 12 is Tyr or Orn
<220> FEATURE:
<221> NAME/KEY: MISC_FEATURE
<222> LOCATION: (13)..(17)
<223> OTHER INFORMATION: intrachain bridge formed between side chains of Xaa at position 13 and 17.
<220> FEATURE:

<221> NAME/KEY: MISC_FEATURE
<222> LOCATION: (18)..(18)
<223> OTHER INFORMATION: Xaa at position 18 is Arg or Orn
<220> FEATURE:
<221> NAME/KEY: MISC_FEATURE
<222> LOCATION: (27)..(27)
<223> OTHER INFORMATION: Xaa at position 27 is Met or Pro

<400> SEQUENCE: 118

His Ser Gln Gly Thr Phe Thr Ser Asp Tyr Ser Xaa Xaa Leu Asp Ser
1 5 10 15

Xaa Xaa Ala Gln Asp Phe Val Gln Trp Leu Xaa Asn Thr
20 25

<210> SEQ ID NO 119
<211> LENGTH: 30
<212> TYPE: PRT
<213> ORGANISM: Artificial Sequence
<220> FEATURE:
<223> OTHER INFORMATION: insulin B chain peptide analog

<400> SEQUENCE: 119

Phe Val Asn Gln His Leu Cys Gly Ser His Leu Val Glu Ala Leu Tyr
1 5 10 15

Leu Val Cys Gly Glu Arg Gly Phe Phe Tyr Thr Lys Pro Thr
20 25 30

<210> SEQ ID NO 120
<211> LENGTH: 30
<212> TYPE: PRT
<213> ORGANISM: Artificial Sequence
<220> FEATURE:
<223> OTHER INFORMATION: insulin B chain peptide analog

<400> SEQUENCE: 120

Phe Val Asn Gln His Leu Cys Gly Ser His Leu Val Glu Ala Leu Tyr
1 5 10 15

Leu Val Cys Gly Glu Arg Gly Phe Phe Tyr Thr Asp Lys Thr
20 25 30

<210> SEQ ID NO 121
<211> LENGTH: 30
<212> TYPE: PRT
<213> ORGANISM: Artificial Sequence
<220> FEATURE:
<223> OTHER INFORMATION: insulin B chain peptide analog

<400> SEQUENCE: 121

Phe Val Lys Gln His Leu Cys Gly Ser His Leu Val Glu Ala Leu Tyr
1 5 10 15

Leu Val Cys Gly Glu Arg Gly Phe Phe Tyr Thr Glu Lys Thr
20 25 30

<210> SEQ ID NO 122
<211> LENGTH: 30
<212> TYPE: PRT
<213> ORGANISM: Artificial Sequence
<220> FEATURE:
<223> OTHER INFORMATION: insulin B chain peptide analog

<400> SEQUENCE: 122

Phe Val Lys Gln His Leu Cys Gly Ser His Leu Val Glu Ala Leu Tyr
1 5 10 15

Leu Val Cys Gly Glu Arg Gly Phe Phe Tyr Thr Pro Glu Thr
20 25 30

<210> SEQ ID NO 123
<211> LENGTH: 32
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa at position 13 and 17.

<400> SEQUENCE: 123

His Ser Gln Gly Thr Phe Thr Ser Asp Tyr Ser Lys Lys Leu Asp Ser
1 5 10 15

Glu Arg Ala Gln Asp Phe Val Gln Trp Leu Met Asn Thr Glu Glu Lys
20 25 30

<210> SEQ ID NO 124
<211> LENGTH: 4
<212> TYPE: PRT
<213> ORGANISM: Artificial Sequence
<220> FEATURE:
<223> OTHER INFORMATION: peptide fragment

<400> SEQUENCE: 124

Leu Met Asn Thr
1

<210> SEQ ID NO 125
<211> LENGTH: 5
<212> TYPE: PRT
<213> ORGANISM: Artificial Sequence
<220> FEATURE:
<223> OTHER INFORMATION: peptide fragment
<220> FEATURE:
<221> NAME/KEY: MISC_FEATURE
<222> LOCATION: (2)..(2)
<223> OTHER INFORMATION: Xaa at position 2 is Ala or Pro
<220> FEATURE:
<221> NAME/KEY: misc_feature
<222> LOCATION: (3)..(3)
<223> OTHER INFORMATION: Xaa can be any naturally occurring amino acid

<400> SEQUENCE: 125

Leu Xaa Xaa Thr Gly
1 5

<210> SEQ ID NO 126
<211> LENGTH: 5
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (3)..(3)
<223> OTHER INFORMATION: Xaa can be any naturally occurring amino acid

<400> SEQUENCE: 126

Leu Ala Xaa Thr Gly
1 5

<210> SEQ ID NO 127
<211> LENGTH: 5
<212> TYPE: PRT
<213> ORGANISM: Artificial Sequence
<220> FEATURE:

```
<223> OTHER INFORMATION: peptide fragment
<220> FEATURE:
<221> NAME/KEY: misc_feature
<222> LOCATION: (3)..(3)
<223> OTHER INFORMATION: Xaa can be any naturally occurring amino acid

<400> SEQUENCE: 127

Leu Pro Xaa Thr Gly
1               5


<210> SEQ ID NO 128
<211> LENGTH: 5
<212> TYPE: PRT
<213> ORGANISM: Artificial Sequence
<220> FEATURE:
<223> OTHER INFORMATION: peptide fragment
<220> FEATURE:
<221> NAME/KEY: misc_feature
<222> LOCATION: (3)..(3)
<223> OTHER INFORMATION: Xaa can be any naturally occurring amino acid

<400> SEQUENCE: 128

Leu Pro Xaa Ala Gly
1               5


<210> SEQ ID NO 129
<211> LENGTH: 32
<212> TYPE: PRT
<213> ORGANISM: Homo sapiens
<220> FEATURE:
<221> NAME/KEY: misc_feature
<222> LOCATION: (27)..(28)
<223> OTHER INFORMATION: Xaa can be any naturally occurring amino acid

<400> SEQUENCE: 129

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Thr Gly Gly Gly
            20                  25                  30


<210> SEQ ID NO 130
<211> LENGTH: 30
<212> TYPE: PRT
<213> ORGANISM: Homo sapiens
<220> FEATURE:
<221> NAME/KEY: misc_feature
<222> LOCATION: (27)..(28)
<223> OTHER INFORMATION: Xaa can be any naturally occurring amino acid

<400> SEQUENCE: 130

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Thr Gly
            20                  25                  30


<210> SEQ ID NO 131
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: misc_feature
<222> LOCATION: (27)..(28)
```

-continued

```
<223> OTHER INFORMATION: Xaa can be any naturally occurring amino acid

<400> SEQUENCE: 131

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Xaa Xaa Thr Gly
            20                  25                  30


<210> SEQ ID NO 132
<211> LENGTH: 30
<212> TYPE: PRT
<213> ORGANISM: Artificial Sequence
<220> FEATURE:
<223> OTHER INFORMATION: glucagon peptide analog
<220> FEATURE:
<221> NAME/KEY: MISC_FEATURE
<222> LOCATION: (13)..(17)
<223> OTHER INFORMATION: lactam ring formed between side chains of Xaa
      at position 13 and 17.
<220> FEATURE:
<221> NAME/KEY: MISC_FEATURE
<222> LOCATION: (20)..(20)
<223> OTHER INFORMATION: Xaa at position 20 is D-Cys
<220> FEATURE:
<221> NAME/KEY: misc_feature
<222> LOCATION: (27)..(28)
<223> OTHER INFORMATION: Xaa can be any naturally occurring amino acid

<400> SEQUENCE: 132

His Ser Gln Gly Thr Phe Thr Ser Asp Tyr Ser Lys Lys Leu Asp Ser
1               5                   10                  15

Glu Arg Ala Xaa Asp Phe Cys Gln Trp Leu Xaa Xaa Thr Gly
            20                  25                  30
```